US007851150B2

(12) United States Patent
Dahlberg et al.

(10) Patent No.: US 7,851,150 B2
(45) Date of Patent: Dec. 14, 2010

(54) DETECTION OF SMALL NUCLEIC ACIDS

(75) Inventors: James E. Dahlberg, Madison, WI (US);
Hatim T. Allawi, Madison, WI (US);
Victor Lyamichev, Madison, WI (US);
Bruce P. Neri, Madison, WI (US);
Marilyn C. Olson-Munoz, Madison, WI (US); LuAnne Chehak, Janesville, WI (US); Sarah M. Olson, Cross Plains, WI (US)

(73) Assignee: Third Wave Technologies, Inc., Madison, WI (US)

( * ) Notice: Subject to any disclaimer, the term of this patent is extended or adjusted under 35 U.S.C. 154(b) by 0 days.

(21) Appl. No.: 10/740,256

(22) Filed: Dec. 18, 2003

(65) Prior Publication Data

US 2005/0074788 A1 Apr. 7, 2005

Related U.S. Application Data

(60) Provisional application No. 60/434,518, filed on Dec. 18, 2002, provisional application No. 60/443,814, filed on Jan. 30, 2003.

(51) Int. Cl.
*C12Q 1/68* (2006.01)
(52) U.S. Cl. .............................. 435/6; 435/325; 435/375
(58) Field of Classification Search ........................ None
See application file for complete search history.

(56) References Cited

U.S. PATENT DOCUMENTS

| | | | |
|---|---|---|---|
| 4,683,195 A | 7/1987 | Mullis et al. ..................... 435/6 |
| 4,683,202 A | 7/1987 | Mullis .......................... 435/91 |
| 5,118,801 A * | 6/1992 | Lizardi et al. .............. 536/24.1 |
| 5,210,015 A | 5/1993 | Gelfand et al. ................. 435/6 |
| 5,215,899 A * | 6/1993 | Dattagupta ..................... 435/6 |
| 5,270,163 A | 12/1993 | Gold et al. ...................... 435/6 |
| 5,494,810 A | 2/1996 | Barany et al. ............ 435/91.52 |
| 5,593,835 A * | 1/1997 | Rando et al. .................... 435/6 |
| 5,607,834 A * | 3/1997 | Bagwell ........................ 435/6 |
| 5,770,365 A * | 6/1998 | Lane et al. ..................... 435/6 |
| 5,792,614 A | 8/1998 | Western et al. ................. 435/6 |
| 5,858,367 A * | 1/1999 | Rather ..................... 424/190.1 |
| 5,866,336 A * | 2/1999 | Nazarenko et al. ............. 435/6 |
| 5,882,867 A | 3/1999 | Ullman et al. ................. 435/6 |
| 5,914,230 A | 6/1999 | Liu et al. ........................ 435/6 |
| 5,968,740 A * | 10/1999 | Fodor et al. .................... 435/6 |
| 5,985,557 A * | 11/1999 | Prudent et al. ................. 435/6 |
| 5,985,563 A * | 11/1999 | Hyldig-Nielsen et al. ...... 435/6 |
| 6,025,133 A * | 2/2000 | Stull et al. ..................... 435/6 |
| 6,027,889 A * | 2/2000 | Barany et al. ................. 435/6 |
| 6,090,543 A | 7/2000 | Prudent et al. ................. 435/6 |
| 6,183,960 B1 | 2/2001 | Lizardi ......................... 435/6 |
| 6,235,502 B1 | 5/2001 | Weissman et al. .......... 435/91.1 |
| 6,291,187 B1 | 9/2001 | Kingsmore et al. ............ 435/6 |
| 6,410,278 B1 | 6/2002 | Notomi et al. .............. 435/91.2 |
| 6,709,815 B1 | 3/2004 | Dong et al. ..................... 435/6 |

FOREIGN PATENT DOCUMENTS

| | | | |
|---|---|---|---|
| EP | 427073 A2 * | 5/1991 |
| WO | WO0157256 A2 | 8/2001 |
| WO | WO0157256 A3 | 8/2001 |
| WO | WO0190337 A2 | 11/2001 |
| WO | WO0190337 A3 | 11/2001 |

OTHER PUBLICATIONS

Lau et al. (An Abundant Class of Tiny RNAs with Probable Regulatory Roles in Caenorhabditis elegans. Science. Oct. 26, 2001. vol. 294: pp. 858-862).*
Marras et al. "Multiplex detection of single-nucleotide variations using molecular beacons" Genet Anal. Feb. 1999;14(5-6):151-6).*
Morris et al. (Rapid reverse transcription-PCR detection of hepatitis C virus RNA in serum by using the TaqMan fluorogenic detection system J Clin Microbiol. Dec. 1996;34(12):2933-6).*
Ledford et al. ("A multi-site study for detection of the factor V (Leiden) mutation from genomic DNA using a homogeneous invader microtiter plate fluorescence resonance energy transfer (FRET) assay" J Mol Diagn. May 2000;2(2):97-104).*
Barany, *Proc. Natl. Acad. Sci. USA* 88:189 (1991).
Hall, J., et al., *Proc. Natl. Acad. Sci. USA* 97:8272 (2000).
Hardenbol, P, et al., *Nature Biotechnology* 21:673 (2003).
Kaiser et al., *J. Biol. Chem.* 274:21387 (1999).
Lyamichev, V, et al., *Science* 260:778 (1993).
Lyamichev, V, et al., *Nature Biotechnology* 17, 292-296 (1999).
Patel R et al., *Proc. Natl. Acad. Sci. USA* 93:2969 (1996).
SantaLucia, J., *Proc. Natl. Acad. Sci. USA* 95:1460 (1998).
Thomas, DC, et al., Archives of Pathology and Laboratory Medicine 123(12):1170 (1999).
Wu and Wallace, *Genomics* 4:560 (1989).
Francois et al., "Recognition and cleavage of hairpin structures in nucleic acids by oligodeoxynucleotides," NAR 22:3943-3950 (1994).
Azhayeva et at, "Looped oligonucleotides form stable hybrid complexes with a snigle-strained DNA," NAR 23:1170-1176 (1995).
Eis, et al. "An Invasive Cleavage Assay for Direct Quantitation of Specific RNAs" Nature Biotechnology, 2001, pp. 673-676, vol. 19.
Ambros, et al. "microRNAs: Tiny Regulators with Great Potential"Cell, 2001, pp. 823-823, vol. 107.
Dearruda, et al. "Invader technology for DNA and RNA analysis: principles and applications" Expert Review of Molecular Diagnostics, Sep. 2002, pp. 487-496, vol. 2(5).
Moss "RNA interference: It's a small RNA world" Current Biology, 2001, pp. R772-R775, vol. 11.

* cited by examiner

*Primary Examiner*—James D. Schultz
(74) *Attorney, Agent, or Firm*—Casimir Jones, S.C.

(57) ABSTRACT

The present invention relates to compositions and methods for the detection and characterization of interfering RNAs such as micro RNAs (miRNAs) and small interfering RNAs (siRNAs) and other short nucleic acid molecules. More particularly, the present invention relates to methods for the detection and quantitation of interfering RNA expression. The present invention further provides for the detection of variants and types of miRNAs and siRNAs.

48 Claims, 27 Drawing Sheets

Figure 4

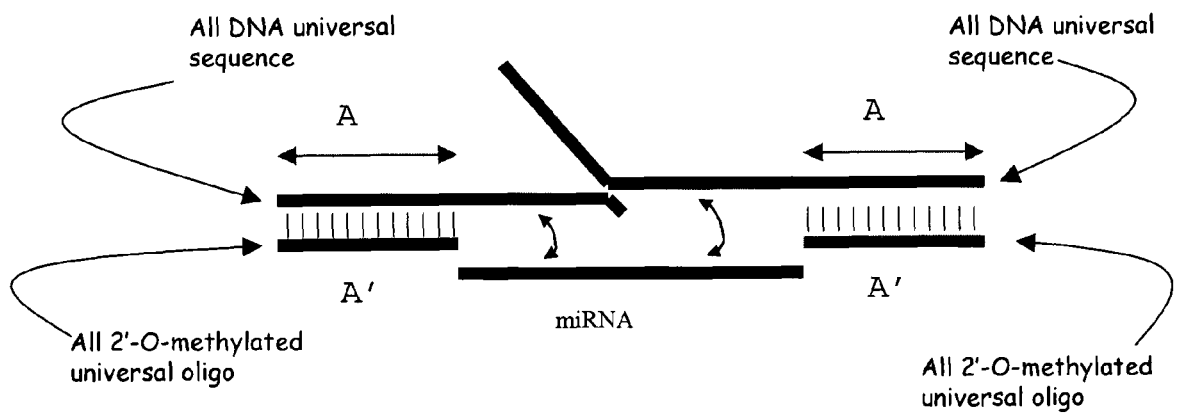

A = Universal sequence that is added to the 3' and 5' of probes and INVADER oligonucleotides, respectively.
From 5' to 3', the probe is composed of the 5'-flap, the miRNA complementary region, and the DNA universal sequence "A".
The INVADER oligonucleotide from 5' to 3', is composed of the DNA universal sequence "A" and an miRNA complementary region.

A' = 2'-O-methyl universal oligonucleotide that compliments the sequence "A" and is added to kits as a standard oligonucleotide.

FIG. 5A

| SEQ ID NO | Target | Oligo type | Sequence (5'-3') |
|---|---|---|---|
| SEQ ID NO:1 | human let-7 miRNA | Invader oligo | ggcacuuugugccAACTATACAACCG |
| SEQ ID NO:2 | human let-7 miRNA | probe oligo | CCGTCGCTGCGTTACTACCTCAcgacguuuucgucg |
| SEQ ID NO:3 | human let-7 miRNA | arrestor oligo | cgacgaaaacgucgugaggguaguaacgcag |
| SEQ ID NO:4 | human let-7 miRNA | miRNA | ugagguaguaguuguuauguu |
| SEQ ID NO:5 | human let-7 miRNA | Invader oligo | ggcacuuugugccAACTATACAACT |
| SEQ ID NO:6 | human let-7 miRNA | probe oligo | CCGTCGCTGCGTCTACTACCTCAcgacguuuucgucg |
| SEQ ID NO:7 | human let-7 miRNA | arrestor oligo | cgacgaaaacgucgagguaguagcgcag |
| SEQ ID NO:8 | human let-7 miRNA | Invader oligo | ggcacuuugugccAACTATACAAT |
| SEQ ID NO:9 | human let-7 miRNA | probe oligo | AACGAGGGCGCACCCTACTACCTCAcgacguuuugcucg |
| SEQ ID NO:10 | human let-7 miRNA | arrestor oligo | cgacguuuugcucgccCTCCATACTTCTC |
| SEQ ID NO:11 | human miR-1 | Invader oligo | ggcagcuuuugcugccCTCCATACTTCTC |
| SEQ ID NO:12 | human miR-1 | probe oligo | AACGAGGCGCACTTACATTCCAcgagccuuuuggcucg |
| SEQ ID NO:13 | human miR-1 | arrestor oligo | cgagccaaaaggcucguggaauguaaaguagcgc |
| SEQ ID NO:14 | human miR-1 | miRNA | uggaauguaaagaaguauggag |
| SEQ ID NO:15 | human miR-1 | Invader oligo | ggcagcuuuugcugccCTCCATACTTCC |
| SEQ ID NO:16 | human miR-1 | probe oligo | AACGAGGCGCACTTTACATTCCAcgagccuuuuggcucg |
| SEQ ID NO:17 | human miR-1 | arrestor oligo | cgagccaaaaggcucguggaauguaaagugcgc |
| SEQ ID NO:18 | human miR-1 | Invader oligo | ggcagcuuuugcugccCTCCATACTTT |
| SEQ ID NO:19 | human miR-1 | probe oligo | AACGAGGCGCACCTTTACATTCCAcgagccuuuuggcucg |
| SEQ ID NO:20 | human miR-1 | arrestor oligo | cgagccaaaaggcucguggaauguaaaagugcgc |
| SEQ ID NO:21 | FAM FRET | FRET probe | Yca-cXt-gct-tcg-tgg |
| SEQ ID NO:22 | SRT | Secondary Reaction template | CCA GGA AGC AAG TGA CGC AGC GAC ggu |
| SEQ ID NO:23 | human let-7 miRNA | Invader oligo | ggcacuuugugccaaCTATACAAT |
| SEQ ID NO:24 | human let-7c miRNA | miRNA | uugguacguuugcgauguggagu |
| SEQ ID NO:25 | human let-7e miRNA | miRNA | ugaguaguaguuugcgauguggagcu |
| SEQ ID NO:26 | human let-7f miRNA | miRNA | uugauauguuagauguggagu |
| SEQ ID NO:27 | human miR-135 | Invader oligo | ccgagcgaaagcucggTTCACATAGGAATC |
| SEQ ID NO:28 | human miR-135 | probe oligo | AACGAGGCGCACAAAAGCCATAcgagccgaaaggcucg |
| SEQ ID NO:29 | human miR-135 | arrestor oligo | cgagccuuucggcucguauggcuuuugcgc |
| SEQ ID NO:30 | human miR-135 | Invader oligo | ccgagcgaaagcucggTTCACATAGGAAC |
| SEQ ID NO:31 | human miR-135 | probe oligo | AACGAGGCGCACTAAAAGCCATAcgagccgaaaggcucg |
| SEQ ID NO:32 | human miR-135 | arrestor oligo | cgagccuuucggcucguauggcuuuuuaugcgc |
| SEQ ID NO:33 | human miR-135 | Invader oligo | ccgagcgaaagcucggTTCACATAGGAC |
| SEQ ID NO:34 | human miR-135 | probe oligo | AACGAGGCGCACATAAAAGCCATAcgagccgaaaggcucg |
| SEQ ID NO:35 | human miR-135 | arrestor oligo | cgagccuuucggcucguauggcuuuuuaugcgc |
| SEQ ID NO:36 | human miR-135 | Invader oligo | ccgagcgaaagcucggTTCACATAGGC |
| SEQ ID NO:37 | human miR-135 | probe oligo | AACGAGGCGCACAATAAAAGCCATAcgagccgaaaggcucg |
| SEQ ID NO:38 | human miR-135 | arrestor oligo | cgagccuuucggcucguauggcuuuuuaugcgc |

FIG. 5B

| SEQ ID NO | Target | Oligo type | Sequence (5'-3') |
|---|---|---|---|
| SEQ ID NO:39 | human miR-16 | miRNA | uagcagcacgtaaauauugcg |
| SEQ ID NO:40 | SRT | Secondary Reaction template | CCAGGAAGCAAGTGGAGGCGTGACggu |
| SEQ ID NO:41 | human GAPDH | Invader oligo | ggaaucauuGGAACATGTAAACCATC |
| SEQ ID NO:42 | human GAPDH | probe oligo | CCGCCGAGATCACGTAGTTGAGGTC-NH2 |
| SEQ ID NO:43 | human GAPDH | arrestor oligo | gaccucaacuacgugauc |
| SEQ ID NO:44 | human miR-125b | miRNA | ucccugagacccuaacuuguga |
| SEQ ID NO:45 | U6 RNA | Invader oligo | GGCCATGCTAATCTTCA |
| SEQ ID NO:46 | U6 RNA | probe oligo | CCCGCGAGATCACTCTGTATCGTTC-NH2 |
| SEQ ID NO:47 | U6 RNA | arrestor oligo | gaagauacagagugauc |
| SEQ ID NO:48 | RED FRET | | Yct-cXt-tct-cag-tgc-g |
| SEQ ID NO:49 | SRT | Secondary Reaction template | CCAGCAAGCAAGTGGTGATCTCGGCggu |
| SEQ ID NO:50 | human let-7a miRNA | probe oligo | CCGTCGCTGCGTCTACTACCTCA-NH2 |
| SEQ ID NO:51 | human let-7a miRNA | Invader oligo | AACTATACAACT |
| SEQ ID NO:52 | human let-7a miRNA | probe oligo | CCGTCGCTGCGTTACTACCTCA-NH2 |
| SEQ ID NO:53 | human let-7a miRNA | Invader oligo | AACTATACAACCG |
| SEQ ID NO:54 | human let-7a miRNA | arrestor oligo | ugagguaguagacgag |
| SEQ ID NO:55 | human miR-15 | probe oligo | AACGAGGCGCACATGTGCTGCTAcgagccuuuuggcucg |
| SEQ ID NO:56 | human miR-15 | Invader oligo | ggcagcuuuugcugcCACAAACCATTC |
| SEQ ID NO:57 | human miR-15 | arrestor oligo | cgagcaaaaggcucguagcagcacaugugcgc |
| SEQ ID NO:58 | human miR-15 | probe oligo | AACGAGGCGCACATGTGCTAGCTCGCCACGCCG-NH2 |
| SEQ ID NO:59 | human miR-15 | arrestor oligo | GCTCGCCACGCCGCACAAACCATTC |
| SEQ ID NO:60 | human miR-15 | stacker oligo | cggcguggcgagc |
| SEQ ID NO:61 | human miR-15 | arrestor oligo | cggcguggcgagcuagcagcacaugugcgc |
| SEQ ID NO:62 | human miR-15 | miRNA | uagcagcacauaaugguuugug |
| SEQ ID NO:63 | human miR-135 | probe oligo | GAGGGCGCACAATAAAAAGCCATATAGCTCGCCACGCCG-NH2 |
| SEQ ID NO:64 | human miR-135 | Invader oligo | GCTCGCCACGCCGTTCACATAGGC |
| SEQ ID NO:65 | human miR-135 | arrestor oligo | cggcguggcgagcuauggcuuuuauugugcgc |
| SEQ ID NO:66 | human miR-15 | arrestor oligo | uagcagcacaugugcgc |
| SEQ ID NO:67 | human miR-15 | probe oligo | AACGAGGCGCACATGTGCTGCTAGGGCGAAGCC |
| SEQ ID NO:68 | human miR-15 | Invader oligo | GGCGAAGCCCACAAACCATTC |
| SEQ ID NO:69 | human miR-15 | probe oligo | AACGAGGCGCACATGTGCTGCTAGGGCGAAgc |
| SEQ ID NO:70 | human miR-15 | Invader oligo | ggcGAAGCCCACAAACCATTC |
| SEQ ID NO:71 | human miR-15 | probe oligo | AACGAGGCGCACATGTGCTGCTAggcuucggcc |
| SEQ ID NO:72 | human miR-15 | Invader oligo | ggcuucggccCACAAACCATTC |
| SEQ ID NO:73 | human let-7a miRNA | Invader oligo | GGCACTTTTGTGCCAACTATACAACT |
| SEQ ID NO:74 | human let-7a miRNA | probe oligo | CCGTCGCTGCTCTACTACCTCACGACGTTTTCGTCG |
| SEQ ID NO:75 | human let-7a miRNA | Invader oligo | ggcacTTTTGTGCCAACTATACAACT |
| SEQ ID NO:76 | human let-7a miRNA | probe oligo | CCGTCGCTGCTCTACTACCTCACGACGTTTTcgucg |

FIG. 5C

| SEQ ID NO | Target | Oligo type | Sequence (5'-3') |
|---|---|---|---|
| SEQ ID NO:77 | human miR-16 miRNA | Invader oligo | ggcagcuuuugcugccCGCCAATATTG |
| SEQ ID NO:78 | human miR-16 miRNA | probe oligo | AACGAGGCGCACTACGTGCTAcgagccuuuuggcucg |
| SEQ ID NO:79 | human miR-16 miRNA | arrestor oligo | cgagccaaaaggcucguagcagcacguaggugcgc |
| SEQ ID NO:80 | human miR-125b miRNA | Invader oligo | ggcgcuuuugcTCACAAGTTAGA |
| SEQ ID NO:81 | human miR-125b miRNA | probe oligo | AACGAGGCGCACGGTCTCAGGGAcgagccuuuggcucg |
| SEQ ID NO:82 | human miR-125b miRNA | arrestor oligo | cgagccaaaggcucguccugagaccgugcgc |
| SEQ ID NO:83 | human let-7a miRNA | probe oligo | CCGTCGTCGTCTACTACCTCAcgacguuuucgucgu |
| SEQ ID NO:84 | human let-7a miRNA | Invader oligo | ugcacuuuugccAACTATACAACT |
| SEQ ID NO:85 | human let-7a miRNA | probe oligo | CCGTCGTCGTCTACTACCTCAcgacguuuucguc |
| SEQ ID NO:86 | human let-7a miRNA | Invader oligo | gcacuuuugccAACTATACAACT |
| SEQ ID NO:87 | precursor human let-7a | miRNA | gggcuuggggugaguuggaguuguauguuuggaauauuuaccaccgugaaacuau gcaauuuucuaccuuuccugaagcca |
| SEQ ID NO:88 | miR-124a 21nt | miRNA | uaaggcacgcggugaaugcca |
| SEQ ID NO:89 | miR-124a 22nt | miRNA | uuaaggcacgcggugaaugcca |
| SEQ ID NO:90 | miR-124a miRNA | probe oligo | CCGTCGCTGCGTCGCGTGCCTTAcgagccuuuuggcucg |
| SEQ ID NO:91 | miR-124a miRNA | arrestor oligo | uaaggcacgcgacgcag |
| SEQ ID NO:92 | miR-124a miRNA | Invader oligo | ggcagcuuuugcugcTGGCATTCACA |
| SEQ ID NO:93 | U6 RNA | probe oligo | CCGCCGAGATCACCTAATCTCTCTGTAT-NH2 |
| SEQ ID NO:94 | U6 RNA | Invader oligo | CATCCTTGCGCAGGGGCCATGA |
| SEQ ID NO:95 | U6 RNA | arrestor oligo | auacagagaagauuaggugauc |
| SEQ ID NO:96 | human miR-135 | miRNA | uauggcuuuuuauuccuaugugaa |
| SEQ ID NO:97 | human miR-1d | miRNA | uggaauguaaagaaguauguau |
| SEQ ID NO:98 | human miR-1d | probe oligo | AACGAGGCGCACTTACATTCCAcgagccuuuuggcucg |
| SEQ ID NO:99 | human miR-1d | Invader oligo | ggcagcuuuugccATACATACTTCC |
| SEQ ID NO:100 | human miR-1d | arrestor oligo | cgagccaaaaggcucguggaaauguaaagugcgc |
| SEQ ID NO:101 | human beta actin siRNA | probe oligo-antisense | AACGAGGCGCACAAGATCATTGCggcuucggcc |
| SEQ ID NO:102 | human beta actin siRNA | Invader oligo-antisense | ggcuucggccAATGAAGATCC |
| SEQ ID NO:103 | human beta actin siRNA | arrestor oligo-antisense | gcaaugaucuugugc |
| SEQ ID NO:104 | human beta actin siRNA | probe oligo-sense | AACGAGGCGCACCTTGATCTTCAggcuucggcc |
| SEQ ID NO:105 | human beta actin siRNA | Invader oligo-sense | ggcuucggccAAGCAATGATA |
| SEQ ID NO:106 | human beta actin siRNA | arrestor oligo-sense | ugaagucaaggugcgc |

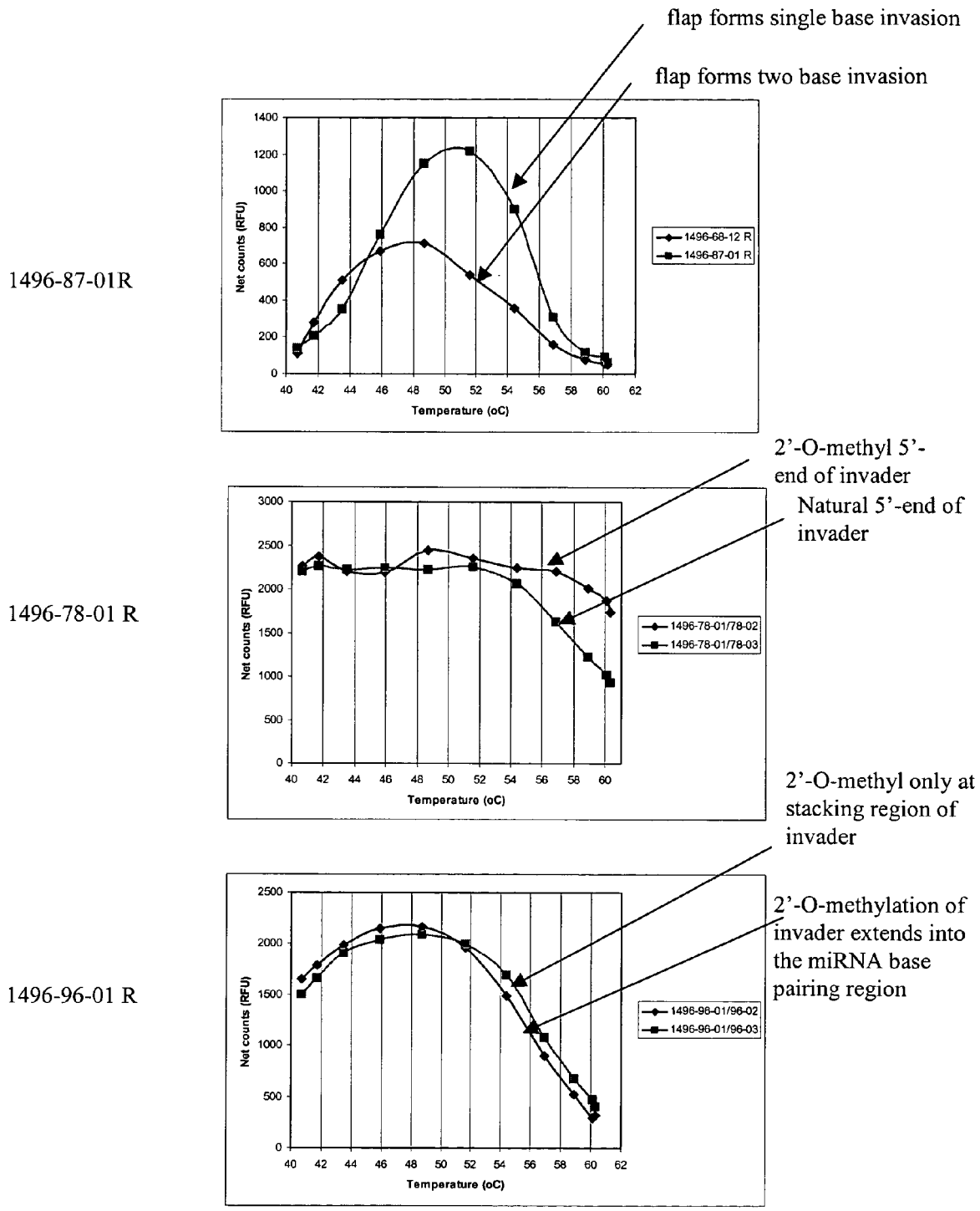

Design Optimization

Figure 8
LOD let-7 (1496-78-01R)
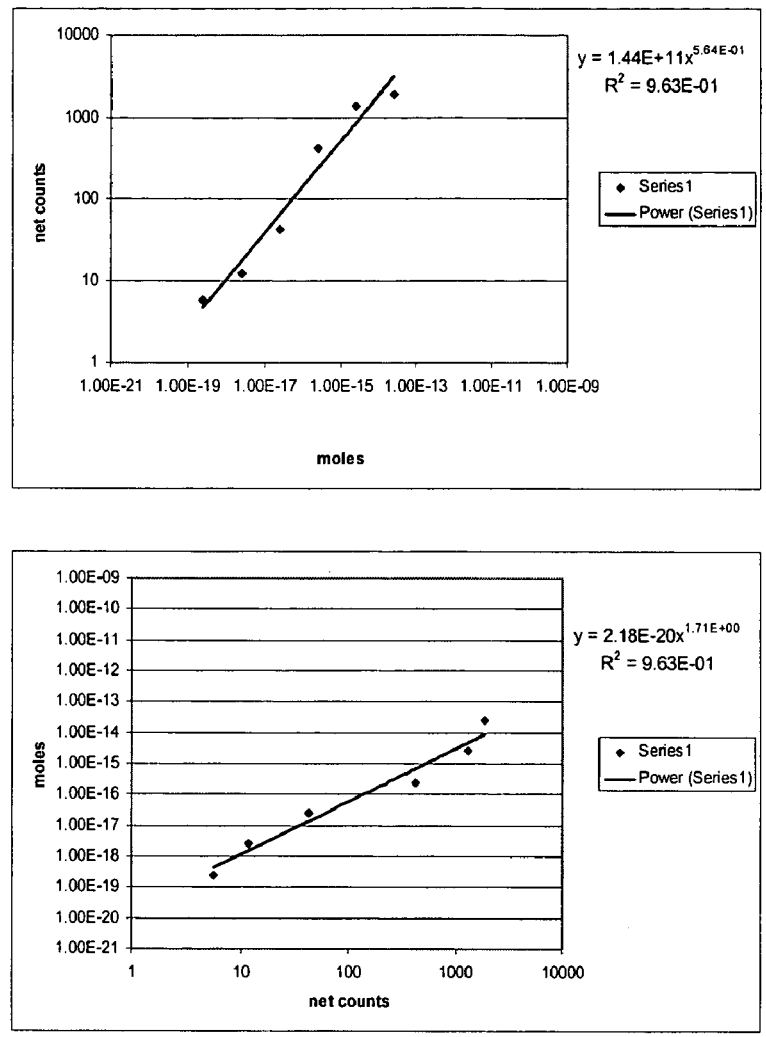
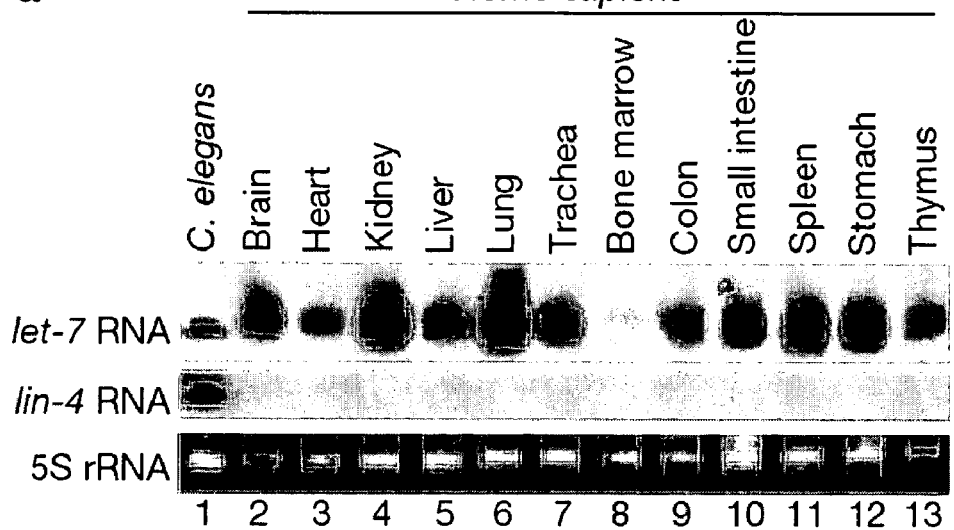

cross reactivity let-7

LOD mir-1

Figure 11
LOD let-7 (1496-78-01R) using CLEAVASE XII enzyme
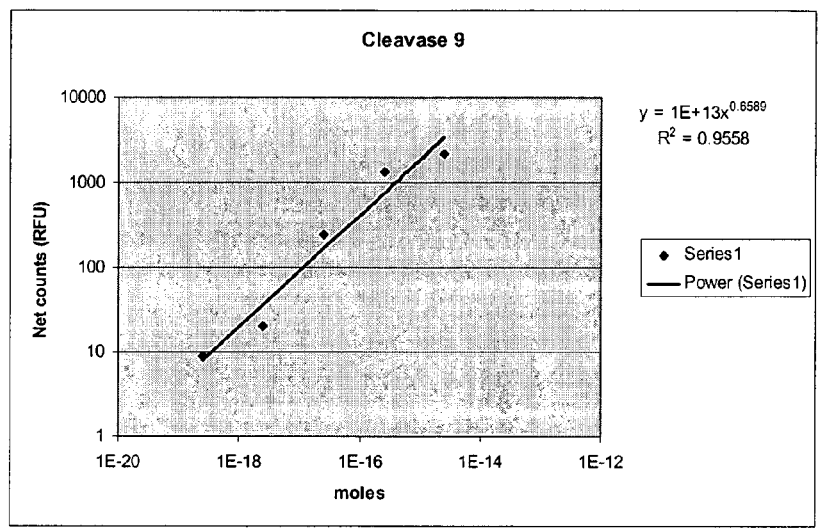
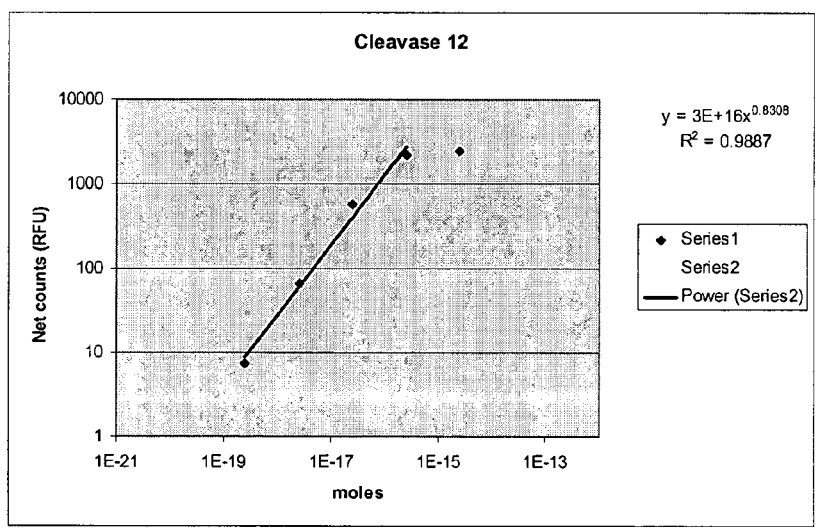

FIGURE 12

|  |  | SEQ ID NO: |
|---|---|---|
| C.elegans | ----GTTCTTCCG-AGAACATATACTAAAATTGAACAATACAGAGAAGATTAGCATGCCCCTGCCAAGGATGACACGCA-AATTCGTGAAGCGTTCCAAATTTT | 107 |
| C.briggsae | ----GTTCTTCCG-AGAACATATACTAAAATTGAACAATACAGAGAAGATTAGCATGCCCCTGCCAAGGATGACACGCA-AATTCGTGAAGCGTTCCAAATTTT | 108 |
| human | -GTGCTCGCTTCGGCAGCACATATACTAAAATTGAACGATACAGAGAAGATTAGCATGCCCCTGCCAAGGATGACACGCA-AATTCGTGAAGCGTTCCATATTTT | 109 |
| mouse | -GTGCTCGCTTCGGCAGCACATATACTAAAATTGAACGATACAGAGAAGATTAGCATGCCCCTGCCAAGGATGACACGCA-AATTCGTGAAGCGTTCCATATTTT- | 110 |
| Xenopus | -GTGCTTGCTTCGGCAGCACATATACTAAAATTGAACGATACAGAGAAGATTAGCATGCCCCTGCCAAGGATGACACGCA-AATTCGTGAAGCGTTCATATTTT | 111 |
| Rat | NGTGCCTGCTTCGGCAGCACATATACTAAAATTGAACGATACAGAGAAGATTAGCATGCCCCTGCCAAGGATGACACGCA-AATTCGTGAAGCGTTCATATTT- | 112 |
| Drosophila | NGTTCTTGCTTCGGCAGCACATATACTAAAATTGAACGATACAGAGAAGATTAGCATGCCCCAGCCAAGGATGACACGCA-AAATCGTGAAGCGTTCCACATTTT | 113 |
| Arabidopsis | ----GTCCCTTCGG--GGACATCCGATAAAATTGGAACGATACAGAGAAGATTAGCATGCCCCTGCCAAGGATGACACGCATAAATCGAGAAATGGTCCAAATTT- | 114 |
|  | **** * * **** ***** * ***** ******************* ** **** *** * ***** ***** |  |

FIGURE 18
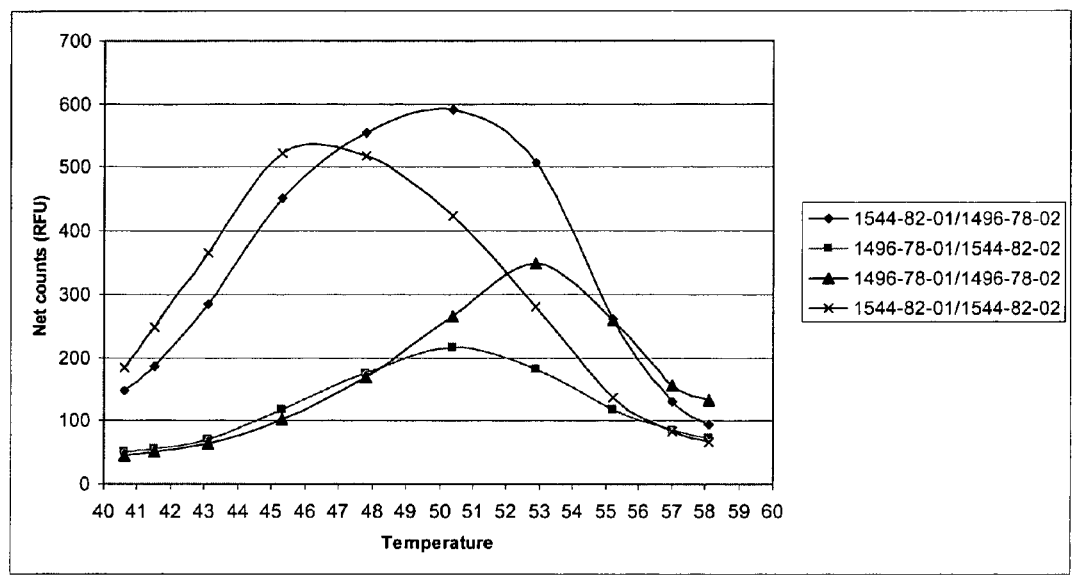
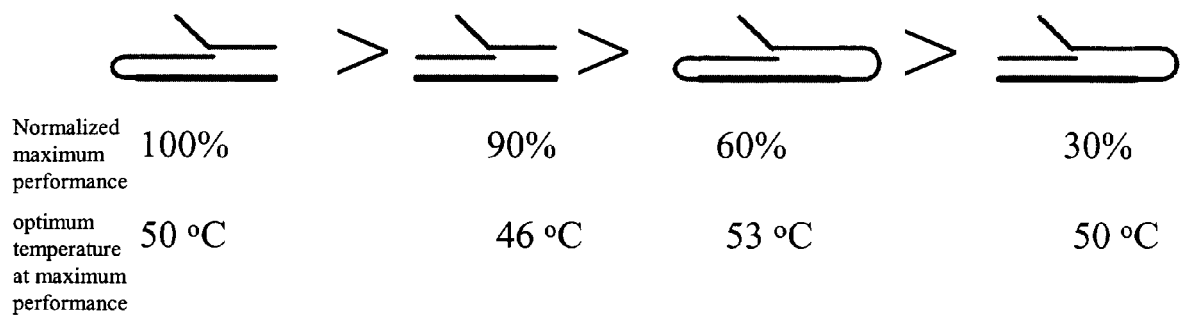
| | | | |
|---|---|---|---|
| Normalized maximum performance | 100% | 90% | 60% | 30% |
| optimum temperature at maximum performance | 50 °C | 46 °C | 53 °C | 50 °C |

Fig. 19
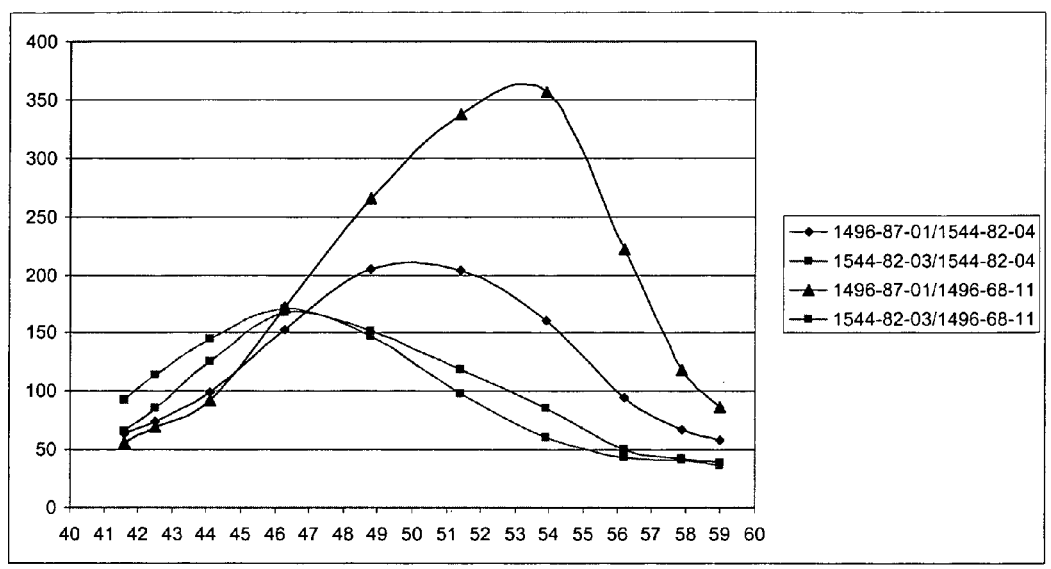
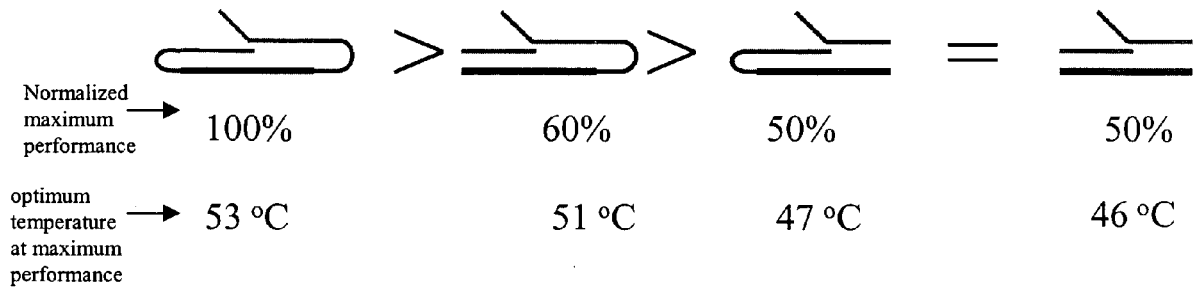
| | | | |
|---|---|---|---|
| Normalized maximum performance | 100% | 60% | 50% | 50% |
| optimum temperature at maximum performance | 53 °C | 51 °C | 47 °C | 46 °C |

Fig. 24

```
                5'-CCGTCGCTGCGT
                                 CTACTACCTCAcgac g              SEQ ID NO:115
SEQ ID NO:73         ttgtgccAACTATACAACT-3'       t            t
                    t   | | | | | |                | | | | |
                     t tcacgg                       gctgc t  t
                       UUGAUAUGUUGGAUGAUGGAGU
                               SEQ ID NO:4

5'-CCGTCGCTGCGT
                                 CTACTACCTCAcgac g              SEQ ID NO:116
SEQ ID NO:124        tt gtgccAACTATACAACT-3'      t            t
                    t   | | | | | |                | | | | | |
                     t t cacggt                      Tgctgc t t
                       UUGAUAUGUUGGAUGAUGGAGU
                               SEQ ID NO:4

5'-CCGTCGCTGCGT
                                 CTACTACCTCAcgac g              SEQ ID NO:117
SEQ ID NO:125        tt gtgccAACTATACAACT-3'      t            t
                    t   | | | | |                  | | | |
                     t t cacg-                      -ctgc t t
                       UUGAUAUGUUGGAUGAUGGAGU
                               SEQ ID NO:4
```

SEQUENCE LISTING

<160> NUMBER OF SEQ ID NOS: 125

<210> SEQ ID NO 1
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl

<400> SEQUENCE: 1
ggcacuuuug ugccaactat acaaccg         27

<210> SEQ ID NO 2
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(36)
<223> OTHER INFORMATION: 2'-O-methyl

<400> SEQUENCE: 2
ccgtcgctgc gttactacct cacgacguuu ucgucg         36

<210> SEQ ID NO 3
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(30)
<223> OTHER INFORMATION: 2'-O-methyl

<400> SEQUENCE: 3
cgacgaaaac gucgugaggu aguaacgcag         30

<210> SEQ ID NO 4
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(20)

<400> SEQUENCE: 4
ugagguagua gguuguauag uu         22

<210> SEQ ID NO 5
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl

<400> SEQUENCE: 5
ggcacuuuug ugccaactat acaact					26

<210> SEQ ID NO 6
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(37)
<223> OTHER INFORMATION: 2'-O-methyl

<400> SEQUENCE: 6
ccgtcgctgc gtctactacc tcacgacguu uucgucg					37

<210> SEQ ID NO 7
<211> LENGTH: 31
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(31)
<223> OTHER INFORMATION: 2'-O-methyl

<400> SEQUENCE: 7
cgacgaaaac gucgugaggu aguagacgca g					31

<210> SEQ ID NO 8
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl

<400> SEQUENCE: 8
ggcacuuuug ugccaactat acaat					25

<210> SEQ ID NO 9
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(38)
<223> OTHER INFORMATION: 2'-O-methyl

<400> SEQUENCE: 9
aacgaggcgc accctactac ctcacgacgu uuucgucg					38

<210> SEQ ID NO 10
<211> LENGTH: 32
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(32)
<223> OTHER INFORMATION: 2'-O-methyl

```
<400> SEQUENCE: 10
cgacgaaaac gucgugaggu aguagggugc gc                                32

<210> SEQ ID NO 11
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 11
ggcagcuuuu gcugccctcc atacttctc                                    29

<210> SEQ ID NO 12
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (23)..(38)
<223> OTHER INFORMATION: 2'-O-methyl

<400> SEQUENCE: 12
aacgaggcgc acttacattc cacgagccuu uuggcucg                          38

<210> SEQ ID NO 13
<211> LENGTH: 32
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(32)
<223> OTHER INFORMATION: 2'-O-methyl

<400> SEQUENCE: 13
cgagccaaaa ggcucgugga auguaagugc gc                                32

<210> SEQ ID NO 14
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 14
uggaauguaa agaaguaugg ag                                           22

<210> SEQ ID NO 15
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
```

```
<223> OTHER INFORMATION: 2'-O-methyl

<400> SEQUENCE: 15
ggcagcuuuu gcugccctcc atacttcc                                              28

<210> SEQ ID NO 16
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 16
aacgaggcgc actttacatt ccacgagccu uuuggcucg                                  39

<210> SEQ ID NO 17
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 17
cgagccaaaa ggcucgugga auguaaagug cgc                                        33

<210> SEQ ID NO 18
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 18
ggcagcuuuu gcugccctcc atacttt                                               27

<210> SEQ ID NO 19
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(40)
<223> OTHER INFORMATION: 2'-O-methyl

<400> SEQUENCE: 19
aacgaggcgc acctttacat tccacgagcc uuuuggcucg                                 40

<210> SEQ ID NO 20
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: modified_base
```

<222> LOCATION: (1)..(34)

<400> SEQUENCE: 20
cgagccaaaa ggcucgugga auguaaaggu gcgc                              34

<210> SEQ ID NO 21
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(13)
<223> OTHER INFORMATION: 2'-O-methyl
<220> FEATURE:
<221> NAME/KEY: misc_feature
<222> LOCATION: (3)..(3)
<223> OTHER INFORMATION: The residue at this position is linked to a
      quencher.

<400> SEQUENCE: 21
cactgcttcg tgg                                                     13

<210> SEQ ID NO 22
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-O-methyl

<400> SEQUENCE: 22
ccaggaagca agtgacgcag cgacggu                                      27

<210> SEQ ID NO 23
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 23
ggcacuuuug ugccaactat acaat                                        25

<210> SEQ ID NO 24
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 24
uugguauguu ggaugaugga gu                                           22

<210> SEQ ID NO 25
<211> LENGTH: 21
<212> TYPE: RNA

```
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(21)
<223> OTHER INFORMATION: 2'-O-methyl

<400> SEQUENCE: 25
ugguacguug gaugauggag u                                                   21

<210> SEQ ID NO 26
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 26
uugauauguu agaugaugga gu                                                  22

<210> SEQ ID NO 27
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 27
ccgagcgaaa gcucggttca cataggaatc                                          30

<210> SEQ ID NO 28
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 28
aacgaggcgc acaaaaagcc atacgagccg aaaggcucg                                39

<210> SEQ ID NO 29
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 29
cgagccuuuc ggcucguaug gcuuuuugug cgc                                      33

<210> SEQ ID NO 30
<211> LENGTH: 29
```

```
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 30
ccgagcgaaa gcucggttca cataggaac                                      29

<210> SEQ ID NO 31
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(40)
<223> OTHER INFORMATION: 2'-O-methyl

<400> SEQUENCE: 31
aacgaggcgc actaaaaagc catacgagcc gaaaggcucg                          40

<210> SEQ ID NO 32
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(34)
<223> OTHER INFORMATION: 2'-O-methyl

<400> SEQUENCE: 32
cgagccuuuc ggcucguaug gcuuuuuagu gcgc                                34

<210> SEQ ID NO 33
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 33
ccgagcgaaa gcucggttca cataggac                                       28

<210> SEQ ID NO 34
<211> LENGTH: 41
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (26)..(41)
<223> OTHER INFORMATION: 2'-O-methyl

<400> SEQUENCE: 34
aacgaggcgc acataaaaag ccatacgagc cgaaaggcuc g                        41

<210> SEQ ID NO 35
```

```
<211> LENGTH: 35
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(35)
<223> OTHER INFORMATION: 2'-O-methyl

<400> SEQUENCE: 35
cgagccuuuc ggcucguaug gcuuuuuaug ugcgc                              35

<210> SEQ ID NO 36
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 36
ccgagcgaaa gcucggttca cataggc                                       27

<210> SEQ ID NO 37
<211> LENGTH: 42
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (27)..(42)
<223> OTHER INFORMATION: 2'-O-methyl

<400> SEQUENCE: 37
aacgaggcgc acaataaaaa gccatacgag ccgaaaggcu cg                      42

<210> SEQ ID NO 38
<211> LENGTH: 36
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(36)
<223> OTHER INFORMATION: 2'-O-methyl

<400> SEQUENCE: 38
cgagccuuuc ggcucguaug gcuuuuuauu gugcgc                             36

<210> SEQ ID NO 39
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 39
uagcagcacg taaauauugg cg                                            22
```

<210> SEQ ID NO 40
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(27)
<223> OTHER INFORMATION: 2'-O-methyl

<400> SEQUENCE: 40
ccaggaagca agtggaggcg tgacggu       27

<210> SEQ ID NO 41
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(11)
<223> OTHER INFORMATION: 2'-O-methyl

<400> SEQUENCE: 41
ggaaucauau uggaacatgt aaaccatc       28

<210> SEQ ID NO 42
<211> LENGTH: 25
<212> TYPE: DNA
<213> ORGANISM: Artificial Sequence
<220> FEATURE:
<223> OTHER INFORMATION: Synthetic

<400> SEQUENCE: 42
ccgccgagat cacgtagttg aggtc       25

<210> SEQ ID NO 43
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-O-methyl

<400> SEQUENCE: 43
gaccucaacu acgugauc       18

<210> SEQ ID NO 44
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 44
ucccugagac ccuaacuugu ga       22

<210> SEQ ID NO 45
<211> LENGTH: 17
<212> TYPE: DNA

<213> ORGANISM: Artificial Sequence
<220> FEATURE:
<223> OTHER INFORMATION: Synthetic

<400> SEQUENCE: 45
ggccatgcta atcttca                                                    17

<210> SEQ ID NO 46
<211> LENGTH: 25
<212> TYPE: DNA
<213> ORGANISM: Artificial Sequence
<220> FEATURE:
<223> OTHER INFORMATION: Synthetic

<400> SEQUENCE: 46
ccgccgagat cactctgtat cgttc                                           25

<210> SEQ ID NO 47
<211> LENGTH: 18
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(18)
<223> OTHER INFORMATION: 2'-O-methyl

<400> SEQUENCE: 47
gaacgauaca gagugauc                                                   18

<210> SEQ ID NO 48
<211> LENGTH: 14
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(14)
<223> OTHER INFORMATION: 2'-O-methyl
<220> FEATURE:
<221> NAME/KEY: misc_feature
<222> LOCATION: (3)..(3)
<223> OTHER INFORMATION: The residue at this position is linked to a
      quencher.

<400> SEQUENCE: 48
ctcttctcag tgcg                                                       14

<210> SEQ ID NO 49
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (26)..(28)
<223> OTHER INFORMATION: 2'-O-methyl

<400> SEQUENCE: 49
ccagcaagca agtggtgatc tcggcggu                                        28

<210> SEQ ID NO 50
<211> LENGTH: 23
<212> TYPE: DNA
<213> ORGANISM: Artificial Sequence
<220> FEATURE:

```
<223> OTHER INFORMATION: Synthetic

<400> SEQUENCE: 50
ccgtcgctgc gtctactacc tca                                              23

<210> SEQ ID NO 51
<211> LENGTH: 12
<212> TYPE: DNA
<213> ORGANISM: Artificial Sequence
<220> FEATURE:
<223> OTHER INFORMATION: Synthetic

<400> SEQUENCE: 51
aactatacaa ct                                                          12

<210> SEQ ID NO 52
<211> LENGTH: 22
<212> TYPE: DNA
<213> ORGANISM: Artificial Sequence
<220> FEATURE:
<223> OTHER INFORMATION: Synthetic

<400> SEQUENCE: 52
ccgtcgctgc gttactacct ca                                               22

<210> SEQ ID NO 53
<211> LENGTH: 13
<212> TYPE: DNA
<213> ORGANISM: Artificial Sequence
<220> FEATURE:
<223> OTHER INFORMATION: Synthetic

<400> SEQUENCE: 53
aactatacaa ccg                                                         13

<210> SEQ ID NO 54
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 54
ugagguagua gacgcag                                                     17

<210> SEQ ID NO 55
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 55
aacgaggcgc acatgtgctg ctacgagccu uuuggcucg                             39

<210> SEQ ID NO 56
<211> LENGTH: 28
<212> TYPE: DNA
<213> ORGANISM: Artificial Sequence
```

```
<220> FEATURE:
<223> OTHER INFORMATION: Synthetic
<220> FEATURE:
<221> NAME/KEY: modified_base
<222> LOCATION: (17)..(28)
<223> OTHER INFORMATION: 2'-O-methyl

<400> SEQUENCE: 56
ggcagcuuuu gcugcccaca aaccattc                                              28

<210> SEQ ID NO 57
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 57
cgagccaaaa ggcucguagc agcacaugug cgc                                        33

<210> SEQ ID NO 58
<211> LENGTH: 36
<212> TYPE: DNA
<213> ORGANISM: Artificial Sequence
<220> FEATURE:
<223> OTHER INFORMATION: Synthetic

<400> SEQUENCE: 58
aacgaggcgc acatgtgctg ctagctcgcc acgccg                                     36

<210> SEQ ID NO 59
<211> LENGTH: 25
<212> TYPE: DNA
<213> ORGANISM: Artificial Sequence
<220> FEATURE:
<223> OTHER INFORMATION: Synthetic

<400> SEQUENCE: 59
gctcgccacg ccgcacaaac cattc                                                 25

<210> SEQ ID NO 60
<211> LENGTH: 13
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(13)

<400> SEQUENCE: 60
cggcguggcg agc                                                              13

<210> SEQ ID NO 61
<211> LENGTH: 30
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(30)
<223> OTHER INFORMATION: 2'-O-methyl

<400> SEQUENCE: 61
```

```
cggcguggcg agcuagcagc acaugugcgc                                    30

<210> SEQ ID NO 62
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 62
uagcagcaca uaaugguuug ug                                            22

<210> SEQ ID NO 63
<211> LENGTH: 39
<212> TYPE: DNA
<213> ORGANISM: Artificial Sequence
<220> FEATURE:
<223> OTHER INFORMATION: Synthetic

<400> SEQUENCE: 63
aacgaggcgc acaataaaaa gccatagctc gccacgccg                          39

<210> SEQ ID NO 64
<211> LENGTH: 24
<212> TYPE: DNA
<213> ORGANISM: Artificial Sequence
<220> FEATURE:
<223> OTHER INFORMATION: Synthetic

<400> SEQUENCE: 64
gctcgccacg ccgttcacat aggc                                          24

<210> SEQ ID NO 65
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 65
cggcguggcg agcuauggcu uuuuauugug cgc                                33

<210> SEQ ID NO 66
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 66
uagcagcaca ugugcgc                                                  17

<210> SEQ ID NO 67
<211> LENGTH: 32
<212> TYPE: DNA
```

```
<213> ORGANISM: Artificial Sequence
<220> FEATURE:
<223> OTHER INFORMATION: Synthetic

<400> SEQUENCE: 67
aacgaggcgc acatgtgctg ctaggcgaag cc                                    32

<210> SEQ ID NO 68
<211> LENGTH: 21
<212> TYPE: DNA
<213> ORGANISM: Artificial Sequence
<220> FEATURE:
<223> OTHER INFORMATION: Synthetic

<400> SEQUENCE: 68
ggcgaagccc acaaaccatt c                                                21

<210> SEQ ID NO 69
<211> LENGTH: 32
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (30)..(32)
<223> OTHER INFORMATION: 2'-O-methyl

<400> SEQUENCE: 69
aacgaggcgc acatgtgctg ctaggcgaag cc                                    32

<210> SEQ ID NO 70
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(3)
<223> OTHER INFORMATION: 2'-O-methyl

<400> SEQUENCE: 70
ggcgaagccc acaaaccatt c                                                21

<210> SEQ ID NO 71
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-O-methyl

<400> SEQUENCE: 71
aacgaggcgc acatgtgctg ctaggcuucg gcc                                   33

<210> SEQ ID NO 72
<211> LENGTH: 22
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-O-methyl
```

<400> SEQUENCE: 72
ggcuucggcc cacaaaccat tc                                          22

<210> SEQ ID NO 73
<211> LENGTH: 26
<212> TYPE: DNA
<213> ORGANISM: Artificial Sequence
<220> FEATURE:
<223> OTHER INFORMATION: Synthetic

<400> SEQUENCE: 73
ggcacttttg tgccaactat acaact                                      26

<210> SEQ ID NO 74
<211> LENGTH: 37
<212> TYPE: DNA
<213> ORGANISM: Artificial Sequence
<220> FEATURE:
<223> OTHER INFORMATION: Synthetic

<400> SEQUENCE: 74
ccgtcgctgc gtctactacc tcacgacgtt ttcgtcg                          37

<210> SEQ ID NO 75
<211> LENGTH: 26
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(5)
<223> OTHER INFORMATION: 2'-O-methyl

<400> SEQUENCE: 75
ggcacttttg tgccaactat acaact                                      26

<210> SEQ ID NO 76
<211> LENGTH: 37
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (33)..(37)
<223> OTHER INFORMATION: 2'-O-methyl

<400> SEQUENCE: 76
ccgtcgctgc gtctactacc tcacgacgtt ttcgucg                          37

<210> SEQ ID NO 77
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 77
ggcagcuuuu gcugcccgcc aatattg                                     27

<210> SEQ ID NO 78

```
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (25)..(40)
<223> OTHER INFORMATION: 2'-O-methyl

<400> SEQUENCE: 78
aacgaggcgc actacgtgct gctacgagcc uuuuggcucg                              40

<210> SEQ ID NO 79
<211> LENGTH: 34
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(34)
<223> OTHER INFORMATION: 2'-O-methyl

<400> SEQUENCE: 79
cgagccaaaa ggcucguagc agcacguagu gcgc                                    34

<210> SEQ ID NO 80
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 80
ggcagcuuuu gctgcctcac aagttaga                                           28

<210> SEQ ID NO 81
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 81
aacgaggcgc acggtctcag ggacgagccu uuuggcucg                               39

<210> SEQ ID NO 82
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 82
cgagccaaaa ggcucguccc ugagaccgug cgc                                     33
```

```
<210> SEQ ID NO 83
<211> LENGTH: 38
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(38)
<223> OTHER INFORMATION: 2'-O-methyl

<400> SEQUENCE: 83
ccgtcgctgc gtctactacc tcacgacguu uucgucgu                                    38

<210> SEQ ID NO 84
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(15)
<223> OTHER INFORMATION: 2'-O-methyl

<400> SEQUENCE: 84
uggcacuuuu gugccaacta tacaact                                                27

<210> SEQ ID NO 85
<211> LENGTH: 36
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(36)
<223> OTHER INFORMATION: 2'-O-methyl

<400> SEQUENCE: 85
ccgtcgctgc gtctactacc tcacgacguu uucguc                                      36

<210> SEQ ID NO 86
<211> LENGTH: 25
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(13)
<223> OTHER INFORMATION: 2'-O-methyl

<400> SEQUENCE: 86
gcacuuuugu gccaactata caact                                                  25

<210> SEQ ID NO 87
<211> LENGTH: 85
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(85)
<223> OTHER INFORMATION: 2'-O-methyl

<400> SEQUENCE: 87
gggcuuuggg gugagguagu agguuguaua guuuggaaua uuaccaccgg ugaacuaugc            60
```
aauuuucuac cuuuccugaa guccc                                                 85

<210> SEQ ID NO 88
<211> LENGTH: 21
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(21)
<223> OTHER INFORMATION: 2'-O-methyl

<400> SEQUENCE: 88
uaaggcacgc ggugaaugcc a                                                     21

<210> SEQ ID NO 89
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 89
uuaaggcacg cggugaaugc ca                                                    22

<210> SEQ ID NO 90
<211> LENGTH: 39
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 90
ccgtcgctgc gtcgcgtgcc ttacgagccu uuuggcucg                                  39

<210> SEQ ID NO 91
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 91
uaaggcacgc gacgcag                                                          17

<210> SEQ ID NO 92
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 92
ggcagcuuuu gcugccuggc attcaca                                    27

<210> SEQ ID NO 93
<211> LENGTH: 29
<212> TYPE: DNA
<213> ORGANISM: Artificial Sequence
<220> FEATURE:
<223> OTHER INFORMATION: Synthetic

<400> SEQUENCE: 93
ccgccgagat cacctaatct tctctgtat                                  29

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94
catccttgcg cagggggccat ga                                         22

<210> SEQ ID NO 95
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 95
auacagagaa gauuagguga uc                                          22

<210> SEQ ID NO 96
<211> LENGTH: 24
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(24)
<223> OTHER INFORMATION: 2'-O-methyl

<400> SEQUENCE: 96
uauggcuuuu uauuccuaug ugaa                                        24

<210> SEQ ID NO 97
<211> LENGTH: 22
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(22)
<223> OTHER INFORMATION: 2'-O-methyl

<400> SEQUENCE: 97
uggaauguaa agaaguaugu au                                          22

<210> SEQ ID NO 98
<211> LENGTH: 39
<212> TYPE: DNA

```
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(39)
<223> OTHER INFORMATION: 2'-O-methyl

<400> SEQUENCE: 98
aacgaggcgc actttacatt ccacgagccu uuuggcucg                          39

<210> SEQ ID NO 99
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(16)
<223> OTHER INFORMATION: 2'-O-methyl

<400> SEQUENCE: 99
ggcagcuuuu gcugccatac atacttcc                                      28

<210> SEQ ID NO 100
<211> LENGTH: 33
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(33)
<223> OTHER INFORMATION: 2'-O-methyl

<400> SEQUENCE: 100
cgagccaaaa ggcucgugga auguaaagug cgc                                33

<210> SEQ ID NO 101
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-O-methyl

<400> SEQUENCE: 101
aacgaggcgc acaagatcat tgcggcuucg gcc                                33

<210> SEQ ID NO 102
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-O-methyl

<400> SEQUENCE: 102
ggcuucggcc aatgaagatc c                                             21

<210> SEQ ID NO 103
<211> LENGTH: 17
```

```
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 103
gcaaugaucu ugugcgc                                                    17

<210> SEQ ID NO 104
<211> LENGTH: 33
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (24)..(33)
<223> OTHER INFORMATION: 2'-O-methyl

<400> SEQUENCE: 104
aacgaggcgc accttgatct tcaggcuucg gcc                                  33

<210> SEQ ID NO 105
<211> LENGTH: 21
<212> TYPE: DNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(10)
<223> OTHER INFORMATION: 2'-O-methyl

<400> SEQUENCE: 105
ggcuucggcc aagcaatgat a                                               21

<210> SEQ ID NO 106
<211> LENGTH: 17
<212> TYPE: RNA
<213> ORGANISM: Artificial Sequence
<220> FEATURE:
<223> OTHER INFORMATION: Synthetic
<220> FEATURE:
<221> NAME/KEY: modified_base
<222> LOCATION: (1)..(17)
<223> OTHER INFORMATION: 2'-O-methyl

<400> SEQUENCE: 106
ugaagaucaa ggugcgc                                                    17

<210> SEQ ID NO 107
<211> LENGTH: 102
<212> TYPE: DNA
<213> ORGANISM: Caenorhabditis elegans

<400> SEQUENCE: 107
gttcttccga gaacatatac taaaattgga acaatacaga gaagattagc atggcccctg     60
cgcaaggatg acacgcaaat tcgtgaagcg ttccaaattt tt                       102

<210> SEQ ID NO 108
<211> LENGTH: 102
<212> TYPE: DNA
<213> ORGANISM: Caenorhabditis briggsae
```

<400> SEQUENCE: 108
gttcttccga gaacatatac taaaattgga acaatacaga gaagattagc atggcccctg     60
cgcaaggatg acacgcaaat tcgtgaagcg ttccaaattt tt     102

<210> SEQ ID NO 109
<211> LENGTH: 107
<212> TYPE: DNA
<213> ORGANISM: Homo sapiens

<400> SEQUENCE: 109
gtgctcgctt cggcagcaca tatactaaaa ttggaacgat acagagaaga ttagcatggc     60
ccctgcgcaa ggatgacacg caaattcgtg aagcgttcca tattttt     107

<210> SEQ ID NO 110
<211> LENGTH: 106
<212> TYPE: DNA
<213> ORGANISM: Mus musculus

<400> SEQUENCE: 110
gtgctcgctt cggcagcaca tatactaaaa ttggaacgat acagagaaga ttagcatggc     60
ccctgcgcaa ggatgacacg caaattcgtg aagcgttcca tatttt     106

<210> SEQ ID NO 111
<211> LENGTH: 107
<212> TYPE: DNA
<213> ORGANISM: Xenopus sp.

<400> SEQUENCE: 111
gtgcttgctt cggcagcaca tatactaaaa ttggaacgat acagagaaga ttagcatggc     60
ccctgcgcaa ggatgacacg caaattcgtg aagcgttcca tattttt     107

<210> SEQ ID NO 112
<211> LENGTH: 107
<212> TYPE: DNA
<213> ORGANISM: Rattus norvegicus
<220> FEATURE:
<221> NAME/KEY: misc_feature
<222> LOCATION: (1)..(1)
<223> OTHER INFORMATION: n is a, c, g, or t

<400> SEQUENCE: 112
ngtgcctgct tcggcagcac atatactaaa attggaacga tacagagaag attagcatgg     60
cccctgcgca aggatgacac gcaaattcgt gaagcgttcc atatttt     107

<210> SEQ ID NO 113
<211> LENGTH: 108
<212> TYPE: DNA
<213> ORGANISM: Drosophila melanogaster
<220> FEATURE:
<221> NAME/KEY: misc_feature
<222> LOCATION: (1)..(1)
<223> OTHER INFORMATION: n is a, c, g, or t

<400> SEQUENCE: 113
ngttcttgct tcggcagaac atatactaaa attggaacga tacagagaag attagcatgg     60
ccccagcgca aggatgacac gcaaaatcgt gaagcgttcc acattttt     108

<210> SEQ ID NO 114
<211> LENGTH: 102
<212> TYPE: DNA
<213> ORGANISM: Arabidopsis thaliana -continued

<400> SEQUENCE: 114
gtcccttcgg ggacatccga taaaattgga acgatacaga gaagattagc atggcccctg    60
cgcaaggatg acacgcataa atcgagaaat ggtccaaatt tt    102

<210> SEQ ID NO 115
<211> LENGTH: 37
<212> TYPE: DNA
<213> ORGANISM: Artificial Sequence
<220> FEATURE:
<223> OTHER INFORMATION: Synthetic

<400> SEQUENCE: 115
ccgtcgctgc gtctactacc tcacgacgtt ttcgtcg    37

<210> SEQ ID NO 116
<211> LENGTH: 38
<212> TYPE: DNA
<213> ORGANISM: Artificial Sequence
<220> FEATURE:
<223> OTHER INFORMATION: Synthetic

<400> SEQUENCE: 116
ccgtcgctgc gtctactacc tcacgacgtt ttcgtcgt    38

<210> SEQ ID NO 117
<211> LENGTH: 36
<212> TYPE: DNA
<213> ORGANISM: Artificial Sequence
<220> FEATURE:
<223> OTHER INFORMATION: Synthetic

<400> SEQUENCE: 117
ccgtcgctgc gtctactacc tcacgacgtt ttcgtc    36

<210> SEQ ID NO 118
<211> LENGTH: 21
<212> TYPE: DNA
<213> ORGANISM: Artificial Sequence
<220> FEATURE:
<223> OTHER INFORMATION: Synthetic

<400> SEQUENCE: 118
ugaagaucaa gaucauugct t    21

<210> SEQ ID NO 119
<211> LENGTH: 21
<212> TYPE: DNA
<213> ORGANISM: Artificial Sequence
<220> FEATURE:
<223> OTHER INFORMATION: Synthetic

<400> SEQUENCE: 119
gcaaugaucu ugaucuucat t    21

<210> SEQ ID NO 120

<400> SEQUENCE: 120

000

<210> SEQ ID NO 121

<400> SEQUENCE: 121

-continued

```
000

<210> SEQ ID NO 122
<211> LENGTH: 17
<212> TYPE: DNA
<213> ORGANISM: Artificial Sequence
<220> FEATURE:
<223> OTHER INFORMATION: Synthetic

<400> SEQUENCE: 122
gcaaugaucu ugugcgc                                                  17

<210> SEQ ID NO 123
<211> LENGTH: 17
<212> TYPE: DNA
<213> ORGANISM: Artificial Sequence
<220> FEATURE:
<223> OTHER INFORMATION: Synthetic

<400> SEQUENCE: 123
ugaagaucaa ggugcgc                                                  17

<210> SEQ ID NO 124
<211> LENGTH: 27
<212> TYPE: DNA
<213> ORGANISM: Artificial Sequence
<220> FEATURE:
<223> OTHER INFORMATION: Synthetic

<400> SEQUENCE: 124
tggcactttt gtgccaacta tacaact                                       27

<210> SEQ ID NO 125
<211> LENGTH: 25
<212> TYPE: DNA
<213> ORGANISM: Artificial Sequence
<220> FEATURE:
<223> OTHER INFORMATION: Synthetic

<400> SEQUENCE: 125 gcactttgt gccaactata caact                                          25
```

US 7,851,150 B2

DETECTION OF SMALL NUCLEIC ACIDS

The present Application claims priority to U.S. Provisional Application Ser. No. 60/434,518, filed Dec. 18, 2002, and U.S. Application Ser. No. 60/443,814, filed Jan. 30, 2003.

FIELD OF THE INVENTION

The present invention relates to compositions and methods for the detection and characterization of interfering RNAs such as micro RNAs (miRNAs) and small interfering RNAs (siRNAs) and other short nucleic acid molecules. More particularly, the present invention relates to improved methods for the detection and quantitation of interfering RNA expression. The present invention further provides for the detection of variants and types of miRNAs and siRNAs.

BACKGROUND OF THE INVENTION

MicroRNAs (miRNAs) are a new class of noncoding RNAs, which are encoded as short inverted repeats in the genomes of invertebrates and vertebrates (Ambros, (2001) Cell 107, 823-826; Moss (2002) Curr. Biol. 12, R138-R140). miRNAs are modulators of target miRNA translation and stability, although most target mRNAs remain to be identified. miRNAs sequence-specifically control translation of target mRNAs by binding to sites of antisense complementarity in 3' untranslated regions (UTRs) (Ambros, supra; Moss, supra; Lagos-Quintana et al., (2001) Science 294, 853-858; Lau et al., (2001) Science 294, 858-862; Lee et al., (2001) Science 294, 862-864).

Several miRNAs, such as let-7 RNA, miR-1, miR-34, miR-60, and miR-87, are highly conserved between invertebrates and vertebrates, implicating that they may recognize multiple sites and/or multiple targets of presumably conserved function (Lagos-Quintana et al., supra; Lau et al., supra; Lee et al., supra; Pasquinelli et al., (2000) Nature 408:86). The small temporal RNAs (stRNAs) lin-4 and let-7 represent a subclass of miRNAs identified by genetic analysis in *Caenorhabditis elegans*, which are developmentally regulated and themselves control developmental programs, such as timing of neuronal rewiring, Dauer larva formation, vulva formation, and the terminal differentiation of hypodermal cells.

miRNAs are typically excised from 60- to 70-nucleotide foldback RNA precursor structures, which are sometimes detected at the onset of miRNA precursor expression (Grishok et al., (2001) Cell 106, 23-34; Hutvagner et al. (2001) Science 93, 834-838; Ketting et al., (2001) Genes Dev. 15, 2654-2659) or during expression of very abundant miRNAs (Lagos-Quintana et al., supra; Lau et al., supra; Lee et al., supra). Generally, only one of the strands of the hairpin precursor molecule is excised and accumulates, presumably because it is protected by associated proteins from RNA degradation. These putative proteins may mediate the translational suppression. The miRNA precursor processing reaction requires Dicer RNase III and Argonaute family members (Grishok et al., supra; Hutvagner et al., supra; Ketting et al., supra).

In addition to their impact on gene expression, these small RNAs, often in the range of 21-22 nucleotides, may find utility in areas of therapeutics and drug discovery, e.g. as drug targets or as pharmaceutical agents. Thus, in some circumstances, it may be important to know approximately how much of each miRNA exists in cells. In some cases, it may further be important to compare levels of miRNA in different tissue types or before and after application of a stimulus, e.g. a chemical or physical intervention. Because related siRNAs and miRNAs may be present in low amounts in cells, it is desirable that methods of detection be both sensitive and specific. Moreover, for certain applications, it may be beneficial to identify methods suitable for high throughput screening, e.g. homogeneous methods, multiplexed methods, or those suitable to highly parallel automated manipulation and limited temperature changes.

Although miRNAs play important roles in the regulation of gene expression, effective techniques for the detection and quantitation of miRNA expression are lacking. To date, the principal methods used for quantitation of miRNAs are based on gel electrophoresis. The miRNAs are detected either by Northern blotting or by the presence of radioactive RNase-resistant duplexes. Northern blotting and chip hybridization methods have relatively low analytical sensitivity (Krichevsky et al. 2003), so microgram quantities of RNA are needed for analyses; moreover, transfer of small RNAs to filters can introduce problems with reproducibility of quantitation and is not typically amendable to high-throughput. Moreover, detection methods based on RNase resistance require highly radioactive probes. Further, assays based solely on probe hybridization may not provide adequate discrimination between isotypes closely related in sequence. Alternative approaches involve cloning the miRNAs and then sequencing the inserts. While this approach may be suitable for discriminating single-base differences between closely related miRNA species, it is time consuming and laborious.

Like miRNAs, small interfering RNAs (siRNAs) are small RNA molecules involved in cell defense, e.g. against viral RNA, via a response termed RNA interference (RNAi) (Cullen, B. R., Nature Immunology, 3: 597-599 (2002)). One class of siRNAs is produced through the action of the Dicer enzyme and RNA-induced silencing complex (RISC) protein complex as part of the RNAi response to the presence of double stranded RNA in cells (Khvorova, A. et al., Cell 115: 209-216 (2003)). Another class of siRNAs is synthetic and encompasses short duplexes, usually 21-23 nt with characteristic dinucleotide overhangs (Elbashir, S. M. et al., EMBO J. 20: 6877-6888 (2001)) introduced directly into cells via transfection or expression from an introduced vector (Paul, C. P. et al., Nature Biotechnology 20: 505-508 (2002), US Patent Application Publication No. 2003/0148519A1, herein incorporated by reference in its entirety for all purposes). In some cases, siRNAs appear to persist as defined sequences, making them analogous in function and composition to miRNAs (Elbashir, S. M. et al., supra). What is needed are efficient and accurate methods of detecting and quantitating miRNA and siRNA levels.

SUMMARY OF THE INVENTION

The present invention relates to compositions and methods for the detection and characterization of small nucleic acids, such as interfering RNAs and other short nucleic acid molecules. More particularly, the present invention relates to improved methods for the detection and quantitation of interfering RNA expression.

For example, the present invention provides a method, comprising: hybridizing at least one nucleic acid (e.g., that contains sequence that is not complementary to the interfering RNA) to a interfering RNA target to generate a detection structure and detecting the detection structure. In some embodiments, the interfering RNA target is an miRNA. In other embodiments, the interfering RNA target is an siRNA. In some embodiments, the siRNA is double stranded.

In some embodiments, the detection structure comprises an invasive cleavage structure. For example, in some embodiments, the nucleic acid comprises first and second oligonucleotides configured to form an invasive cleavage structure in combination with the miRNA. In some embodiments, the nucleic acid comprises a first oligonucleotide configured to form an invasive cleavage structure in combination with said miRNA. In some embodiments, the first oligonucleotide comprises a 5' portion and a 3' portion, wherein said 3' portion is configured to hybridize to said target sequence, and wherein said 5' portion is configured to not hybridize to said target sequence. In some embodiments employing a second oligonucleotide, the second oligonucleotide comprises a 5' portion and a 3' portion, wherein said 5' portion is configured to hybridize to said target sequence, and wherein said 3' portion is configured to not hybridize to said target sequence. In some embodiments, the detecting step comprises use of an INVADER assay.

In some embodiments, the detection structure comprises a circular oligonucleotide hybridized to said small RNA to generate a circular detection structure. In some embodiments, the detecting step comprises use of a rolling circle replication assay.

In some embodiments, the detecting step(s) comprises use of a detection assay including, but not limited to, sequencing assays, polymerase chain reaction assays, hybridization assays, hybridization assays employing a probe complementary to a mutation, microarray assays, bead array assays, primer extension assays, enzyme mismatch cleavage assays, branched hybridization assays, NASBA assays, molecular beacon assays, cycling probe assays, ligase chain reaction assays, invasive cleavage structure assays, ARMS assays, and sandwich hybridization assays. In some preferred embodiments, the detecting step is carried out in cell lysate.

In some embodiments, the methods of the present invention comprise detecting a second nucleic acid target. In some preferred embodiments, the second nucleic acid target is RNA. In some particularly preferred embodiments, the second nucleic acid target is U6 RNA or GAPDH mRNA.

In some embodiments, the nucleic acid used to form the detection structure comprises a template with one or more sites sufficiently complementary to the small RNA so as to allow the RNA to hybridize to the template and be extended in an extension reaction. In some embodiments, the extension reaction is a polymerase chain reaction wherein one or more RNAs are used as primers in the polymerase chain reaction. In some such embodiments, a single type of RNA binds to two locations on the template to provide the polymerase chain reaction primers. In other embodiments, two or more RNAs are used as primers. In such embodiments, the detection of an amplification product signifies the presence of the two or more RNAs in the sample (i.e., an miRNA multiplex assay). Similar methods may be employed in a ligase chain reaction where the miRNAs are used as the ligated oligonucleotide(s).

In some embodiments, the method comprises detection of a plurality of miRNAs. In some such embodiments, the plurality of miRNAs comprises polymorphisms of the same miRNA. In other embodiments, the plurality of miRNAs comprises different miRNAs (e.g., Let-7, miR-1, miR-1d, miR-135, miR-15, miR-16, miR-124a, or miR125b).

The present invention also provides kits for conducting any of the above methods. For example, in some embodiments, the present invention provides kits comprising a nucleic acid configured for forming a detection structure when hybridized to an RNA target sequence. In some embodiments, the kits are configured to detect an miRNA. In some preferred embodiments, kits are configured to detect a Let-7, miR-1, miR-135, miR-15, miR-16, miR-lb, miR-124a, or miR125b miRNA. In some preferred embodiments, kits are configured to co-detect a second RNA target with an miRNA target.

DESCRIPTION OF THE DRAWINGS

FIG. 4 shows a third exemplary detection structure used in some embodiments of the present invention.

FIG. 5 (SEQ ID NOS:1-106) shows exemplary oligonucleotides for use with the present invention. Bases of the target miRNA are underlined in lower case. DNA residues in probe or INVADER oligonucleotides are in regular type. Lower case type indicates 2'-O-methyl residues.

FIG. 6 shows the results of temperature optimization experiments for let-7.

FIG. 8 shows the results of limit of detection (LOD) experiments for let-7.

FIG. 11 shows the results of CLEAVASE enzymes 1× and XII comparisons using let-7 miRNA.

FIG. 12 (SEC) ID NOS:107-114) shows a partial sequence alignment of U6 RNA sequences from various organisms.

FIG. 18 shows the results of temperature optimization experiments using the assay designs described in FIG. 16.

FIG. 19 shows the results of temperature optimization experiments using the 10-mer probe and 12-mer INVADER oligonucleotide designs.

FIG. 22 shows the results of invasive cleavage assays to detect miR-124a.

FIG. 24 (SEQ ID NOS:115-117, SEQ ID NO:4, SEQ ID NO:73, and SEQ ID NOS:124-125) shows results of experiments testing the effect on miRNA detection of altering probe and oligonucleotide length.

DEFINITIONS

Figure 1:
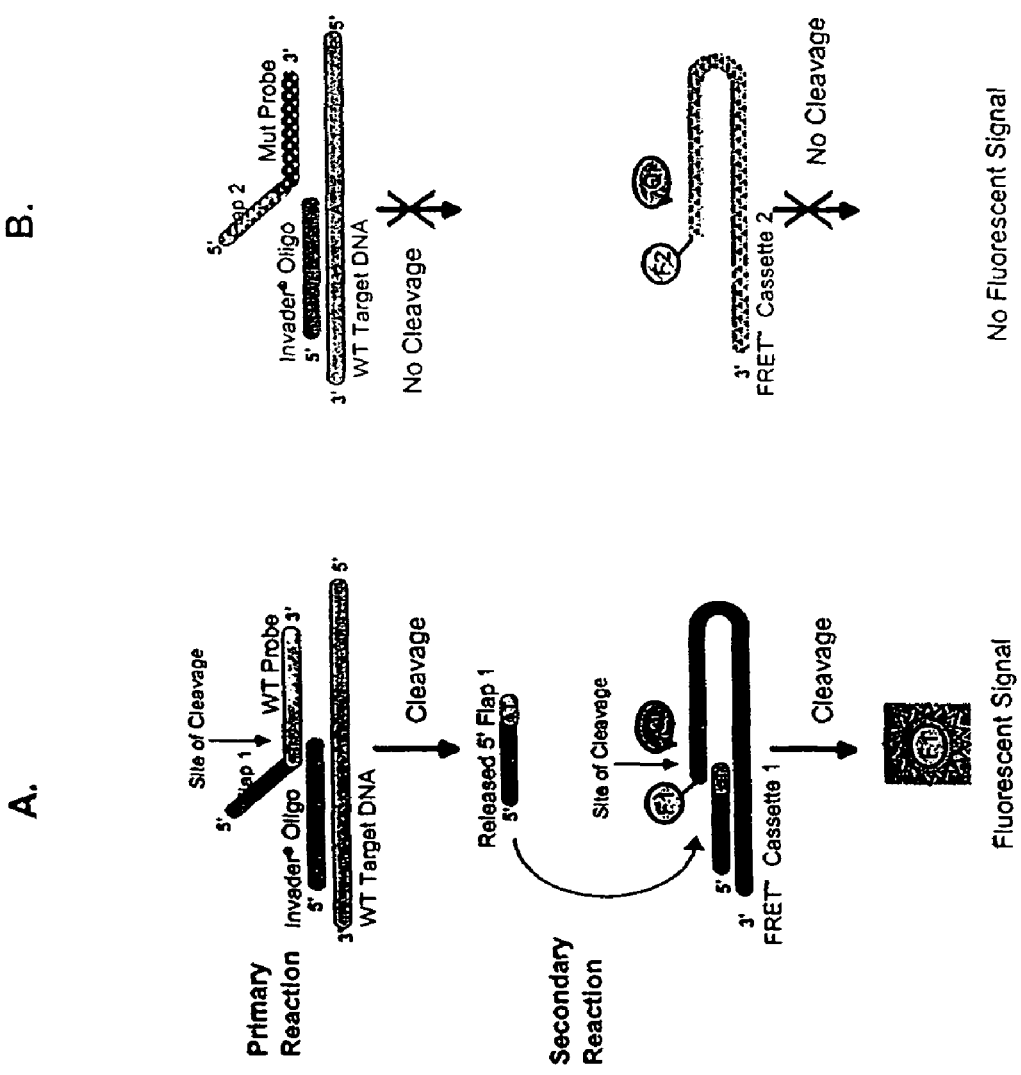
FIG. 1 shows a schematic diagram of INVADER oligonucleotides, probe oligonucleotides and FRET cassettes for detecting two different alleles (e.g., differing by a single nucleotide) in a single reaction.

To facilitate an understanding of the present invention, a number of terms and phrases are defined below:

As used herein, the term "miRNA" refers to micro RNA. As used herein, the term "miRNA target sequence" refers to a miRNA that is to be detected (e.g., in the presence of other nucleic acids). In some embodiments, a miRNA target sequence is a variant of a miRNA.

As used herein, the term "RNA detection structure" refers to a structure formed by hybridizing a nucleic acid (e.g., an oligonucleotide) to an RNA target, e.g., an miRNA or siRNA. In some embodiments, the nucleic acid is a single nucleic acid (e.g., a larger nucleic acid with a small region (or regions) of homology to the miRNA). In other embodiments, the nucleic acid comprises two nucleic acids (e.g., that hybridize to the miRNA to form a hairpin (e.g., single or double hairpin) structure). In preferred embodiments, miRNA detection structures are capable of detection using known nucleic acid detection methods, including, but not limited to, those disclosed herein.

In some embodiments, RNA detection structures are further modified following the hybridization step. For example, in some embodiments, the nucleic acid that is hybridized to the RNA provides a template for extension of the RNA by a nucleic acid polymerase. The RNA is hybridized to the nucleic acid and is then extended using the polymerase. In other embodiments, the nucleic acid serves as a template for the hybridization and ligation of additional nucleic acids to the RNA.

The term "siRNAs" refers to short interfering RNAs. In some embodiments, siRNAs comprise a duplex, or double-stranded region, where each strand of the double-stranded region is about 18 to 25 nucleotides long; the double-stranded region can be as short as 16, and as long as 29, base pairs long, where the length is determined by the antisense strand. Often siRNAs contain from about two to four unpaired nucleotides at the 3' end of each strand. SiRNAs appear to function as key intermediates in triggering RNA interference in invertebrates and in vertebrates, and in triggering sequence-specific RNA degradation during posttranscriptional gene silencing in plants. At least one strand of the duplex or double-stranded region of a siRNA is substantially homologous to or substantially complementary to a target RNA molecule. The strand complementary to a target RNA molecule is the "antisense" strand; the strand homologous to the target RNA molecule is the "sense" strand and is also complementary to the siRNA antisense strand. One strand of the double stranded region need not be the exact length of the opposite strand' thus, one strand may have at least one fewer nucleotides than the opposite complementary strand, resulting in a "bubble" or at least one unmatched base in the opposite strand. One strand of the double-stranded region need not be exactly complementary to the opposite strand; thus, the strand, preferably the sense strand, may have at least one mismatched base pair.

SiRNAs may also contain additional sequences; non-limiting examples of such sequences include linking sequences, or loops, which connect the two strands of the duplex region. This form of siRNAs may be referred to "si-like RNA", "short hairpin siRNA" where the short refers to the duplex region of the siRNA, or "hairpin siRNA". Additional non-limiting examples of additional sequences present in siRNAs include stem and other folded structures. The additional sequences may or may not have known functions; non-limiting examples of such functions include increasing stability of an siRNA molecule, or providing a cellular destination signal.

As used herein, the terms "subject" and "patient" refer to any organisms including plants, microorganisms and animals (e.g., mammals such as dogs, cats, livestock, and humans).

As used herein, the term "INVADER assay reagents" or "invasive cleavage assay reagents" refers to one or more reagents for detecting target sequences, said reagents comprising oligonucleotides capable of forming an invasive cleavage structure in the presence of the target sequence. In some embodiments, the INVADER assay reagents further comprise an agent for detecting the presence of an invasive cleavage structure (e.g., a cleavage agent). In some embodiments, the oligonucleotides comprise first and second oligonucleotides, said first oligonucleotide comprising a 5' portion complementary to a first region of the target nucleic acid and said second oligonucleotide comprising a 3' portion and a 5' portion, said 5' portion complementary to a second region of the target nucleic acid downstream of and contiguous to the first portion. In some embodiments, the 3' portion of the second oligonucleotide comprises a 3' terminal nucleotide not complementary to the target nucleic acid. In preferred embodiments, the 3' portion of the second oligonucleotide consists of a single nucleotide not complementary to the target nucleic acid. In some embodiments, the first and second oligonucleotides are covalently coupled to one another (e.g., through a linker).

In some embodiments, the INVADER assay reagents further comprise a solid support. For example, in some embodiments, the one or more oligonucleotides of the assay reagents (e.g., first and/or second oligonucleotide, whether bridging or non-bridging) is attached to the solid support. In some embodiments, the INVADER assay reagents further comprise a buffer solution. In some preferred embodiments, the buffer solution comprises a source of divalent cations (e.g., $Mn^{2+}$ and/or $Mg^{2+}$ ions). Individual ingredients (e.g., oligonucleotides, enzymes, buffers, target nucleic acids) that collectively make up INVADER assay reagents are termed "INVADER assay reagent components."

In some embodiments, the INVADER assay reagents further comprise a third oligonucleotide complementary to a third portion of the target nucleic acid upstream of the first portion of the first target nucleic acid. In yet other embodiments, the INVADER assay reagents further comprise a target nucleic acid. In some embodiments, the INVADER assay reagents further comprise a second target nucleic acid. In yet other embodiments, the INVADER assay reagents further comprise a third oligonucleotide comprising a 5' portion complementary to a first region of the second target nucleic acid. In some specific embodiments, the 3' portion of the third oligonucleotide is covalently linked to the second target nucleic acid. In other specific embodiments, the second target nucleic acid further comprises a 5' portion, wherein the 5' portion of the second target nucleic acid is the third oligonucleotide. In still other embodiments, the INVADER assay reagents further comprise an ARRESTOR molecule (e.g., ARRESTOR oligonucleotide).

The inclusion of 2' O-methylated ARRESTOR oligonucleotides, which are base-paired fully to each probe's target-specific region and partially to its 5'-flap region, sequesters uncleaved probes and prevents X-structure formation in the secondary reaction, as described in Eis et al., Nature Biotechnology, 19:673-676 (2001), herein incorporated by reference in its entirety for all purposes.

In some preferred embodiments, the INVADER assay reagents further comprise reagents for detecting a nucleic acid cleavage product. In some embodiments, one or more oligonucleotides in the INVADER assay reagents comprise a label. In some preferred embodiments, said first oligonucleotide comprises a label. In other preferred embodiments, said third oligonucleotide comprises a label. In particularly preferred embodiments, the reagents comprise a first and/or a third oligonucleotide labeled with moieties that produce a fluorescence resonance energy transfer (FRET) effect.

In some embodiments one or more the INVADER assay reagents may be provided in a predispensed format (i.e., premeasured for use in a step of the procedure without re-measurement or re-dispensing). In some embodiments, selected INVADER assay reagent components are mixed and predispensed together. In preferred embodiments, predispensed assay reagent components are predispensed and are provided in a reaction vessel (including but not limited to a reaction tube or a well, as in, e.g., a microtiter plate). In particularly preferred embodiments, predispensed INVADER assay reagent components are dried down (e.g., desiccated or lyophilized) in a reaction vessel.

In some embodiments, the INVADER assay reagents are provided as a kit. As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

In some embodiments, the present invention provides INVADER assay reagent kits comprising one or more of the components necessary for practicing the present invention. For example, the present invention provides kits for storing or delivering the enzymes and/or the reaction components necessary to practice an INVADER assay. The kit may include any and all components necessary or desired for assays including, but not limited to, the reagents themselves, buffers, control reagents (e.g., tissue samples, positive and negative control target oligonucleotides, etc.), solid supports, labels, written and/or pictorial instructions and product information, inhibitors, labeling and/or detection reagents, package environmental controls (e.g., ice, desiccants, etc.), and the like. In some embodiments, the kits provide a sub-set of the required components, wherein it is expected that the user will supply the remaining components. In some embodiments, the kits comprise two or more separate containers wherein each container houses a subset of the components to be delivered. For example, a first container (e.g., box) may contain an enzyme (e.g., structure specific cleavage enzyme in a suitable storage buffer and container), while a second box may contain oligonucleotides (e.g., INVADER oligonucleotides, probe oligonucleotides, control target oligonucleotides, etc.).

The term "label" as used herein refers to any atom or molecule that can be used to provide a detectable (preferably quantifiable) effect, and that can be attached to a nucleic acid or protein. Labels include, but are not limited to, dyes; radiolabels such as $^{32}P$; binding moieties such as biotin; haptens such as digoxgenin; luminogenic, phosphorescent or fluorogenic moieties; mass tags; and fluorescent dyes alone or in combination with moieties that can suppress or shift emission spectra by fluorescence resonance energy transfer (FRET). Labels may provide signals detectable by fluorescence, radioactivity, colorimetry, gravimetry, X-ray diffraction or absorption, magnetism, enzymatic activity, characteristics of mass or behavior affected by mass (e.g., MALDI time-of-flight mass spectrometry; fluorescence polarization), and the like. A label may be a charged moiety (positive or negative charge) or alternatively, may be charge neutral. Labels can include or consist of nucleic acid or protein sequence, so long as the sequence comprising the label is detectable.

As used herein, the term "distinct" in reference to signals refers to signals that can be differentiated one from another, e.g., by spectral properties such as fluorescence emission wavelength, color, absorbance, mass, size, fluorescence polarization properties, charge, etc., or by capability of interaction with another moiety, such as with a chemical reagent, an enzyme, an antibody, etc.

As used herein, the terms "complementary" or "complementarity" are used in reference to polynucleotides (i.e., a sequence of nucleotides such as an oligonucleotide or a target nucleic acid) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids. Either term may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the $T_m$ of the formed hybrid. "Hybridization" methods involve the annealing of one nucleic acid to another, complementary nucleic acid, i.e., a nucleic acid having a complementary nucleotide sequence. The ability of two polymers of nucleic acid containing complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960) have been followed by the refinement of this process into an essential tool of modern biology.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs.

As used herein, the term "$T_m$" is used in reference to the "melting temperature." The melting temperature is the temperature at which a population of double-stranded nucleic acid molecules becomes half dissociated into single strands. Several equations for calculating the $T_m$ of nucleic acids are well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (see e.g., Anderson and Young, Quantitative Filter Hybridization, in Nucleic Acid Hybridization (1985). Other references (e.g., Allawi and SantaLucia, Biochemistry 36: 10581-94 (1997) include more sophisticated computations which take structural and environmental, as well as sequence characteristics into account for the calculation of $T_m$.

The term "gene" refers to a DNA sequence that comprises control and coding sequences necessary for the production of an RNA having a non-coding function (e.g., a ribosomal or transfer RNA), a polypeptide or a precursor. The RNA or polypeptide can be encoded by a full length coding sequence or by any portion of the coding sequence so long as the desired activity or function is retained.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant DNA vector" as used herein refers to DNA sequences containing a desired heterologous sequence. For example, although the term is not limited to the use of expressed sequences or sequences that encode an expression product, in some embodiments, the heterologous sequence is a coding sequence and appropriate DNA sequences necessary for either the replication of the coding sequence in a host organism, or the expression of the operably linked coding sequence in a particular host organism. DNA sequences necessary for expression in prokaryotes include a promoter, optionally an operator sequence, a ribosome binding site and possibly other sequences. Eukaryotic cells are known to utilize promoters, polyadenlyation signals and enhancers.

The term "oligonucleotide" as used herein is defined as a molecule comprising two or more deoxyribonucleotides or ribonucleotides, preferably at least 5 nucleotides, more preferably at least about 10-15 nucleotides and more preferably at least about 15 to 30 nucleotides. The exact size will depend on many factors, which in turn depend on the ultimate function or use of the oligonucleotide. The oligonucleotide may be generated in any manner, including chemical synthesis, DNA replication, reverse transcription, PCR, or a combination thereof.

Because mononucleotides are reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends. A first region along a nucleic acid strand is said to be upstream of another region if the 3' end of the first region is before the 5' end of the second region when moving along a strand of nucleic acid in a 5' to 3' direction.

When two different, non-overlapping oligonucleotides anneal to different regions of the same linear complementary nucleic acid sequence, and the 3' end of one oligonucleotide points towards the 5' end of the other, the former may be called the "upstream" oligonucleotide and the latter the "downstream" oligonucleotide. Similarly, when two overlapping oligonucleotides are hybridized to the same linear complementary nucleic acid sequence, with the first oligonucleotide positioned such that its 5' end is upstream of the 5' end of the second oligonucleotide, and the 3' end of the first oligonucleotide is upstream of the 3' end of the second oligonucleotide, the first oligonucleotide may be called the "upstream" oligonucleotide and the second oligonucleotide may be called the "downstream" oligonucleotide.

The term "primer" refers to an oligonucleotide that is capable of acting as a point of initiation of synthesis when placed under conditions in which primer extension is initiated. An oligonucleotide "primer" may occur naturally, as in a purified restriction digest or may be produced synthetically.

A primer is selected to be "substantially" complementary to a strand of specific sequence of the template. A primer must be sufficiently complementary to hybridize with a template strand for primer elongation to occur. A primer sequence need not reflect the exact sequence of the template. For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence has sufficient complementarity with the sequence of the template to hybridize and thereby form a template primer complex for synthesis of the extension product of the primer.

The term "cleavage structure" as used herein, refers to a structure that is formed by the interaction of at least one probe oligonucleotide and a target nucleic acid, forming a structure comprising a duplex, the resulting structure being cleavable by a cleavage means, including but not limited to an enzyme. The cleavage structure is a substrate for specific cleavage by the cleavage means in contrast to a nucleic acid molecule that is a substrate for non-specific cleavage by agents such as phosphodiesterases, which cleave nucleic acid molecules without regard to secondary structure (i.e., no formation of a duplexed structure is required).

The term "cleavage means" or "cleavage agent" as used herein refers to any means that is capable of cleaving a cleavage structure, including but not limited to enzymes. "Structure-specific nucleases" or "structure-specific enzymes" are enzymes that recognize specific secondary structures in a nucleic molecule and cleave these structures. The cleavage means of the invention cleave a nucleic acid molecule in response to the formation of cleavage structures; it is not necessary that the cleavage means cleave the cleavage structure at any particular location within the cleavage structure.

The cleavage means may include nuclease activity provided from a variety of sources including the CLEAVASE enzymes (Third Wave Technologies, Madison, Wis.), the FEN-1 endonucleases (including RAD2 and XPG proteins), Taq DNA polymerase and E. coli DNA polymerase I. The cleavage means may include enzymes having 5' nuclease activity (e.g., Taq DNA polymerase (DNAP), E. coli DNA polymerase I). The cleavage means may also include modified DNA polymerases having 5' nuclease activity but lacking synthetic activity. Examples of cleavage means suitable for use in the methods and kits of the present invention are provided in U.S. Pat. Nos. 5,614,402; 5,795,763; 5,843,669; PCT Appln. Nos WO 98/23774; WO 02/070755A2; and WO0190337A2, each of which is herein incorporated by reference it their entireties.

The term "thermostable" when used in reference to an enzyme, such as a 5' nuclease, indicates that the enzyme is functional or active (i.e., can perform catalysis) at an elevated temperature, i.e., at about 55° C. or higher (e.g., including, but not limited to, 60° C., 65° C., 70° C., 75° C., 80° C., 85° C. or 90° C.).

The term "cleavage products" as used herein, refers to products generated by the reaction of a cleavage means with a cleavage structure (i.e., the treatment of a cleavage structure with a cleavage means).

The term "non-target cleavage product" refers to a product of a cleavage reaction that is not derived from the target nucleic acid. As discussed above, in some of the methods of the present invention, cleavage of the cleavage structure generally occurs within the probe oligonucleotide. The fragments of the probe oligonucleotide generated by this target nucleic acid-dependent cleavage are "non-target cleavage products."

The term "probe oligonucleotide", in the context of an INVADER assay reaction, refers to an oligonucleotide that interacts with a target nucleic acid to form a cleavage structure in the presence or absence of an INVADER oligonucleotide. When annealed to the target nucleic acid, the probe oligonucleotide and target form a cleavage structure and cleavage occurs within the probe oligonucleotide.

The term "INVADER oligonucleotide" refers to an oligonucleotide that hybridizes to a target nucleic acid at a location near the region of hybridization between a probe and the target nucleic acid, wherein the INVADER oligonucleotide comprises a portion (e.g., a chemical moiety, or nucleotide-whether complementary to that target or not) that overlaps with the region of hybridization between the probe and target. In some embodiments, the INVADER oligonucleotide contains sequences at its 3' end that are substantially the same as sequences located at the 5' end of a probe oligonucleotide.

The term "ARRESTOR molecule" refers to an agent added to or included in an invasive cleavage reaction in order to stop one or more reaction components from participating in a subsequent action or reaction. This may be done by sequestering or inactivating some reaction component (e.g., by binding or base-pairing a nucleic acid component, or by binding to a protein component). The term "ARRESTOR oligonucleotide" refers to an oligonucleotide included in an invasive cleavage reaction in order to stop or arrest one or more aspects of any reaction (e.g., the first reaction and/or any subsequent reactions or actions; it is not intended that the ARRESTOR oligonucleotide be limited to any particular reaction or reaction step). This may be done by sequestering some reaction component (e.g., base-pairing to another nucleic acid, or binding to a protein component). However, it is not intended that the term be so limited as to just situations in which a reaction component is sequestered.

The term "cassette" as used herein refers to an oligonucleotide or combination of oligonucleotides configured to generate a detectable signal in response to cleavage of a probe oligonucleotide in an INVADER assay. In preferred embodiments, the cassette hybridizes to a non-target cleavage product from cleavage of the probe oligonucleotide to form a second invasive cleavage structure, such that the cassette can then be cleaved.

Secondary cleavage reactions in some preferred embodiments of the present invention include the use of FRET cassettes. Such molecules provide both a secondary target (Secondary Reaction Target or SRT) and a FRET labeled cleavable sequence, allowing homogeneous detection (i.e., without product separation or other manipulation after the reaction) of the sequential invasive cleavage reaction. Other preferred embodiments use a secondary reaction system in which the FRET probe and synthetic target are provided as separate oligonucleotides. The cleaved 5'-flaps from a primary reaction act as invasive oligonucleotides in a secondary reaction, in which they bind to the appropriate secondary-reaction target (SRT).

In some embodiments, the cassette is a single oligonucleotide comprising a hairpin portion (i.e., a region wherein one portion of the cassette oligonucleotide hybridizes to a second portion of the same oligonucleotide under reaction conditions, to form a duplex). In other embodiments, a cassette comprises at least two oligonucleotides comprising complementary portions that can form a duplex under reaction conditions. In preferred embodiments, the cassette comprises a label. In particularly preferred embodiments, cassette comprises labeled moieties that produce a fluorescence resonance energy transfer (FRET) effect.

The term "substantially single-stranded" when used in reference to a nucleic acid substrate means that the substrate molecule exists primarily as a single strand of nucleic acid in contrast to a double-stranded substrate which exists as two strands of nucleic acid which are held together by inter-strand base pairing interactions.

As used herein, the phrase "non-amplified oligonucleotide detection assay" refers to a detection assay configured to detect the presence or absence of a particular target sequence (e.g., miRNA, SNP, repeat sequence, etc.) that has not been amplified (e.g., by PCR), without creating copies of the target sequence. A "non-amplified oligonucleotide detection assay" may, for example, amplify a signal used to indicate the presence or absence of a particular target sequence or polymorphism within a target sequence, so long as the target sequence is not copied.

As used herein, the phrase "non-amplifying oligonucleotide detection assay" refers to a detection assay configured to detect the presence or absence of a target sequence (e.g., miRNA, SNP, repeat sequence, etc.), without creating copies of the target sequence. A "non-amplifying oligonucleotide detection assay" may, for example, amplify a signal used to indicate the presence or absence of a particular target sequence or polymorphism in a target sequence, so long as the target sequence is not copied.

The term "sequence variation" as used herein refers to differences in nucleic acid sequence between two nucleic acids. For example, a wild-type structural gene and a mutant form of this wild-type structural gene may vary in sequence by the presence of single base substitutions and/or deletions or insertions of one or more nucleotides. These two forms of the structural gene are said to vary in sequence from one another. A second mutant form of the structural gene may exist. This second mutant form is said to vary in sequence from both the wild-type gene and the first mutant form of the gene.

The term "liberating" as used herein refers to the release of a nucleic acid fragment from a larger nucleic acid fragment, such as an oligonucleotide, by the action of, for example, a 5' nuclease such that the released fragment is no longer covalently attached to the remainder of the oligonucleotide.

The term "$K_m$" as used herein refers to the Michaelis-Menten constant for an enzyme and is defined as the concentration of the specific substrate at which a given enzyme yields one-half its maximum velocity in an enzyme catalyzed reaction.

The term "nucleotide analog" as used herein refers to modified or non-naturally occurring nucleotides including but not limited to analogs that have altered stacking interactions such as 7-deaza purines (i.e., 7-deaza-dATP and 7-deaza-dGTP); base analogs with alternative hydrogen bonding configurations (e.g., such as Iso-C and Iso-G and other non-standard base pairs described in U.S. Pat. No. 6,001,983 to S. Benner and herein incorporated by reference); non-hydrogen bonding analogs (e.g., non-polar, aromatic nucleoside analogs such as 2,4-difluorotoluene, described by B. A. Schweitzer and E. T. Kool, J. Org. Chem., 1994, 59, 7238-7242, B. A. Schweitzer and E. T. Kool, J. Am. Chem. Soc., 1995, 117, 1863-1872; each of which is herein incorporated by reference); "universal" bases such as 5-nitroindole and 3-nitropyrrole; and universal purines and pyrimidines (such as "K" and "P" nucleotides, respectively; P. Kong, et al., Nucleic Acids Res., 1989, 17, 10373-10383, P. Kong et al., Nucleic Acids Res., 1992, 20, 5149-5152). Nucleotide analogs include nucleotides having modification on the sugar moiety, such as dideoxy nucleotides and 2'-O-methyl nucleotides. Nucleotide analogs include modified forms of deoxyribonucleotides as well as ribonucleotides.

The term "polymorphic locus" is a locus present in a population that shows variation between members of the population (e.g., the most common allele has a frequency of less than 0.95). In contrast, a "monomorphic locus" is a genetic locus at little or no variations seen between members of the population (generally taken to be a locus at which the most common allele exceeds a frequency of 0.95 in the gene pool of the population).

The term "microorganism" as used herein means an organism too small to be observed with the unaided eye and includes, but is not limited to bacteria, virus, protozoans, fungi, and ciliates.

The term "microbial gene sequences" refers to gene sequences derived from a microorganism.

The term "bacteria" refers to any bacterial species including eubacterial and archaebacterial species.

The term "virus" refers to obligate, ultramicroscopic, intracellular parasites incapable of autonomous replication (i.e., replication requires the use of the host cell's machinery).

The term "sample" in the present specification and claims is used in its broadest sense. On the one hand it is meant to include a specimen or culture (e.g., microbiological cultures). On the other hand, it is meant to include both biological and environmental samples. A sample may include a specimen of synthetic origin.

Biological samples may be animal, including human, fluid, solid (e.g., stool) or tissue, as well as liquid and solid food and feed products and ingredients such as dairy items, vegetables, meat and meat by-products, and waste. Biological samples may be obtained from all of the various families of domestic animals, as well as feral or wild animals, including, but not limited to, such animals as ungulates, bear, fish, lagomorphs, rodents, etc.

Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The term "source of target nucleic acid" refers to any sample that contains nucleic acids (RNA (e.g., miRNA) or DNA). Particularly preferred sources of target nucleic acids are biological samples including, but not limited to blood, saliva, cerebral spinal fluid, pleural fluid, milk, lymph, sputum and semen.

An oligonucleotide is said to be present in "excess" relative to another oligonucleotide (or target nucleic acid sequence) if that oligonucleotide is present at a higher molar concentration that the other oligonucleotide (or target nucleic acid sequence). When an oligonucleotide such as a probe oligonucleotide is present in a cleavage reaction in excess relative to the concentration of the complementary target nucleic acid sequence, the reaction may be used to indicate the amount of the target nucleic acid present. Typically, when present in excess, the probe oligonucleotide will be present in at least a 100-fold molar excess; typically at least 1 pmole of each probe oligonucleotide would be used when the target nucleic acid sequence was present at about 10 fmoles or less.

A sample "suspected of containing" a first and a second target nucleic acid may contain either, both or neither target nucleic acid molecule.

The term "reactant" is used herein in its broadest sense. The reactant can comprise, for example, an enzymatic reactant, a chemical reactant or light (e.g., ultraviolet light, particularly short wavelength ultraviolet light is known to break oligonucleotide chains). Any agent capable of reacting with an oligonucleotide to either shorten (e.g., cleave) or elongate the oligonucleotide is encompassed within the term "reactant."

As used herein, the term "purified" or "to purify" refers to the removal of contaminants from a sample. For example, in some embodiments, recombinant CLEAVASE nucleases are expressed in bacterial host cells and the nucleases are purified by the removal of host cell proteins; the percent of these recombinant nucleases is thereby increased in the sample.

As used herein the term "portion" when in reference to a protein (as in "a portion of a given protein") refers to fragments of that protein. The fragments may range in size from four amino acid residues to the entire amino acid sequence minus one amino acid (e.g., 4, 5, 6, . . . , n–1).

The term "nucleic acid sequence" as used herein refers to an oligonucleotide, nucleotide or polynucleotide, and fragments or portions thereof, and to DNA or RNA of genomic or synthetic origin, which may be single or double stranded, and represent the sense or antisense strand. Similarly, "amino acid sequence" as used herein refers to peptide or protein sequence.

As used herein, the terms "purified" or "substantially purified" refer to molecules, either nucleic or amino acid sequences, that are removed from their natural environment, isolated or separated, and are at least 60% free, preferably 75% free, and most preferably 90% free from other components with which they are naturally associated. An "isolated polynucleotide" or "isolated oligonucleotide" is therefore a substantially purified polynucleotide.

The term "continuous strand of nucleic acid" as used herein is means a strand of nucleic acid that has a continuous, covalently linked, backbone structure, without nicks or other disruptions. The disposition of the base portion of each nucleotide, whether base-paired, single-stranded or mismatched, is not an element in the definition of a continuous strand. The backbone of the continuous strand is not limited to the ribose-phosphate or deoxyribose-phosphate compositions that are found in naturally occurring, unmodified nucleic acids. A nucleic acid of the present invention may comprise modifications in the structure of the backbone, including but not limited to phosphorothioate residues, phosphonate residues, 2' substituted ribose residues (e.g., 2'-O-methyl ribose) and alternative sugar (e.g., arabinose) containing residues.

The term "continuous duplex" as used herein refers to a region of double stranded nucleic acid in which there is no disruption in the progression of basepairs within the duplex (i.e., the base pairs along the duplex are not distorted to accommodate a gap, bulge or mismatch with the confines of the region of continuous duplex). As used herein the term refers only to the arrangement of the basepairs within the duplex, without implication of continuity in the backbone portion of the nucleic acid strand. Duplex nucleic acids with uninterrupted basepairing, but with nicks in one or both strands are within the definition of a continuous duplex.

The term "duplex" refers to the state of nucleic acids in which the base portions of the nucleotides on one strand are bound through hydrogen bonding the their complementary bases arrayed on a second strand. The condition of being in a duplex form reflects on the state of the bases of a nucleic acid. By virtue of base pairing, the strands of nucleic acid also generally assume the tertiary structure of a double helix, having a major and a minor groove. The assumption of the helical form is implicit in the act of becoming duplexed.

The term "template" refers to a strand of nucleic acid on which a complementary copy is built from nucleoside triphosphates through the activity of a template-dependent nucleic acid polymerase. Within a duplex the template strand is, by convention, depicted and described as the "bottom" strand. Similarly, the non-template strand is often depicted and described as the "top" strand.

DESCRIPTION OF THE INVENTION

The present invention relates to compositions and methods for the detection and characterization of micro RNAs (miRNAs) or other short nucleic acid molecules, e.g. siRNAs. The present invention provides improved methods of detecting, characterizing and quantitating miRNA expression. In some embodiments, the present invention provides methods of detecting miRNA expression comprising adding a nucleic acid to a miRNA to aid in detection. The resulting "miRNA detection structure" is then detected using any suitable method including, but not limited to, those disclosed herein. While the following description focuses on the detection and quantitation of miRNAs, it should be understood that the invention also finds use with other short nucleic acid molecules (e.g., DNA and RNA of less than, for example, 50, 40, 30, or 20 nucleotides in length).

I. Formation of a miRNA Detection Structure

In some embodiments, the present invention provides methods of generating miRNA detection structures to aid in the detection of miRNAs. miRNAs are small in size (approximately 21 nucleotides) and are thus difficult to detect using standardized hybridization methods. In some embodiments, the methods of the present invention comprise adding a nucleic acid molecule to an miRNA (e.g., via hybridization, extension, or ligation) to generate a detection structure. Such detection structures can then be detected using any suitable method.

Figure 2:
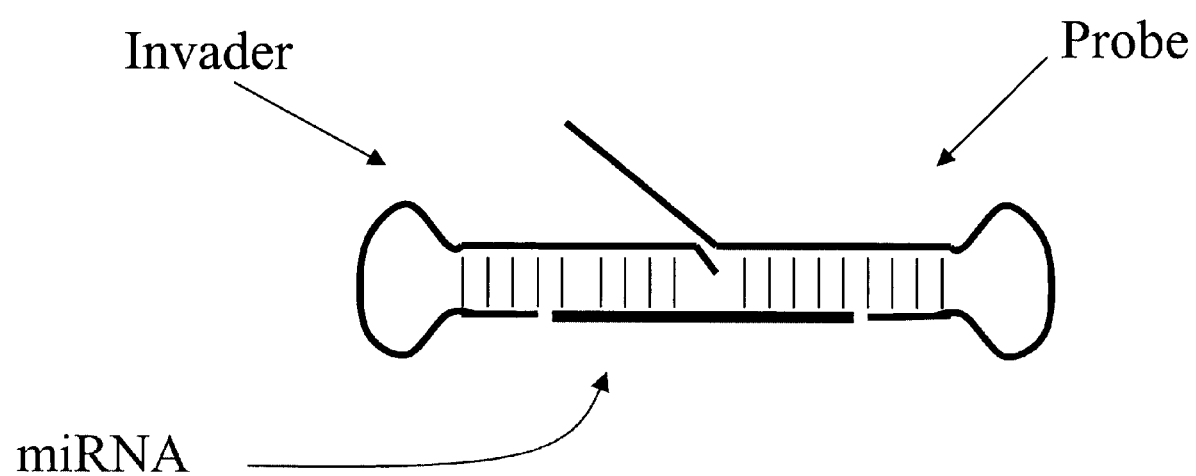
FIG. 2 shows an exemplary detection structure utilized in some embodiments of the present invention.

In one particular embodiment, the detection structure described in FIG. 2 is generated for detection of miRNAs. In this embodiment, two oligonucleotides are annealed to the miRNA to form a double loop or "dumbbell" like structure. The dumbbell structure creates a larger region of double-stranded nucleic acid by extending the ends of the miRNA with a double-stranded region of oligonucleotide. In some embodiments, each end of the miRNA is extended between 2 and 5 nucleotides. In some embodiments, the ends of the oligonucleotides comprise additional nucleic acid sequences that do not hybridize to the miRNA. In some embodiments, these additional sequences form invasive cleavage structures (e.g., INVADER assay invasive cleavage structures). In some embodiments, invasive cleavage structures are detected by the INVADER assay (See e.g., below description).

Figure 3:
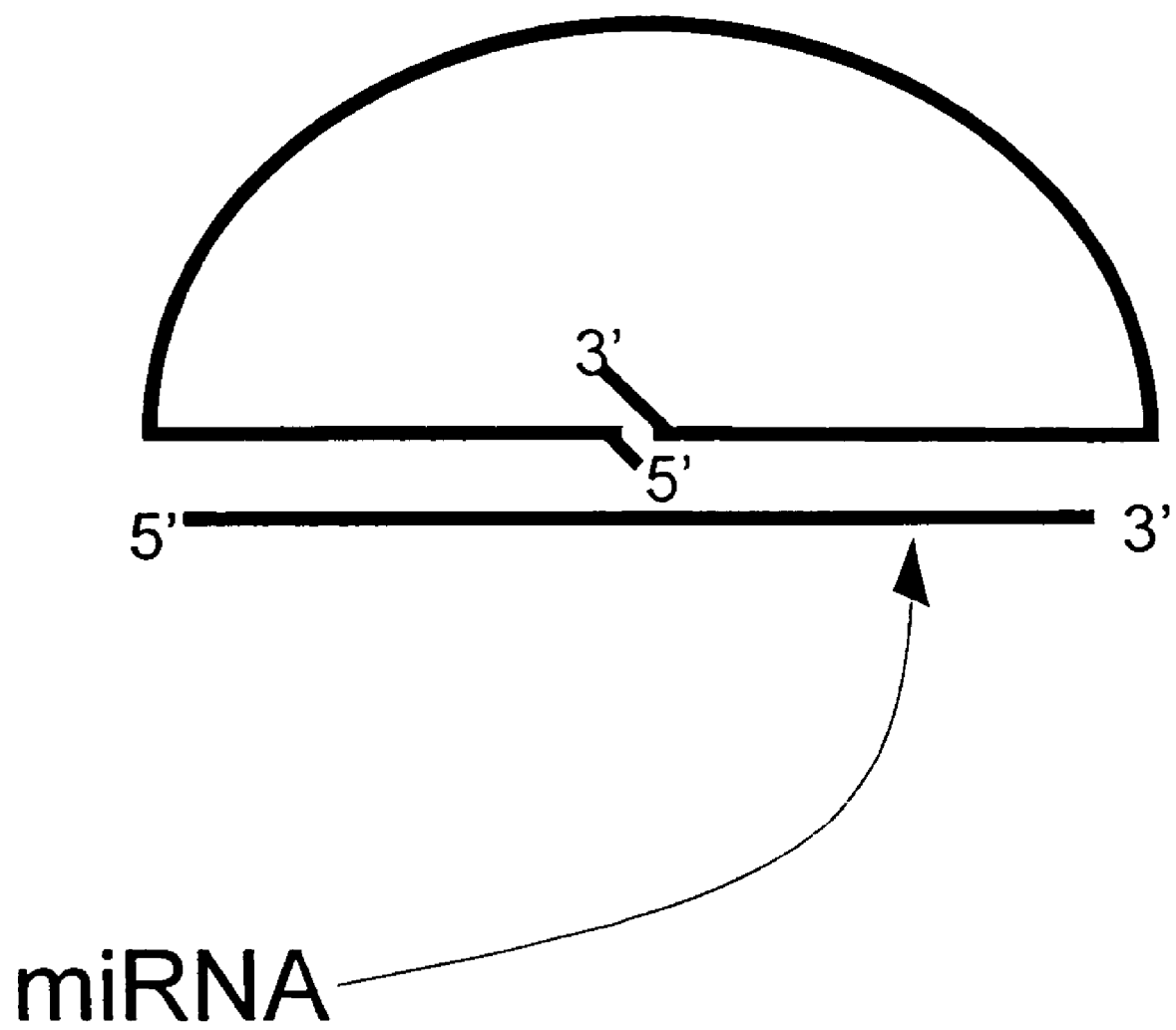
FIG. 3 shows a second exemplary detection structure utilized in some embodiments of the present invention.

In other embodiments, the detection structure described in FIG. 3 is generated for the detection of miRNAs. In this embodiment, one oligonucleotide is annealed to the miRNA to generate an arched structure. The miRNA brings the ends of the oligonucleotide together with greater efficiency than in the absence of the miRNA. In some embodiments, the ends of the oligonucleotide comprise additional sequences that extend beyond the miRNA and do not hybridize to the miRNA. In some embodiments, these additional sequences form invasive cleavage structures (e.g., INVADER assay invasive cleavage structures). In some embodiments, invasive cleavage structures are detected by the INVADER assay (See e.g., below description). In other embodiments, following cleavage of an INVADER assay invasive cleavage structure, the resulting ends are ligated to form a circular structure. In other embodiments, one oligonucleotide is hybridized to a miRNA such that the ends of the oligonucleotide are brought in close proximity (e.g., hybridized to adjacent nucleotides of the miRNA) and are then ligated.

Figure 16:
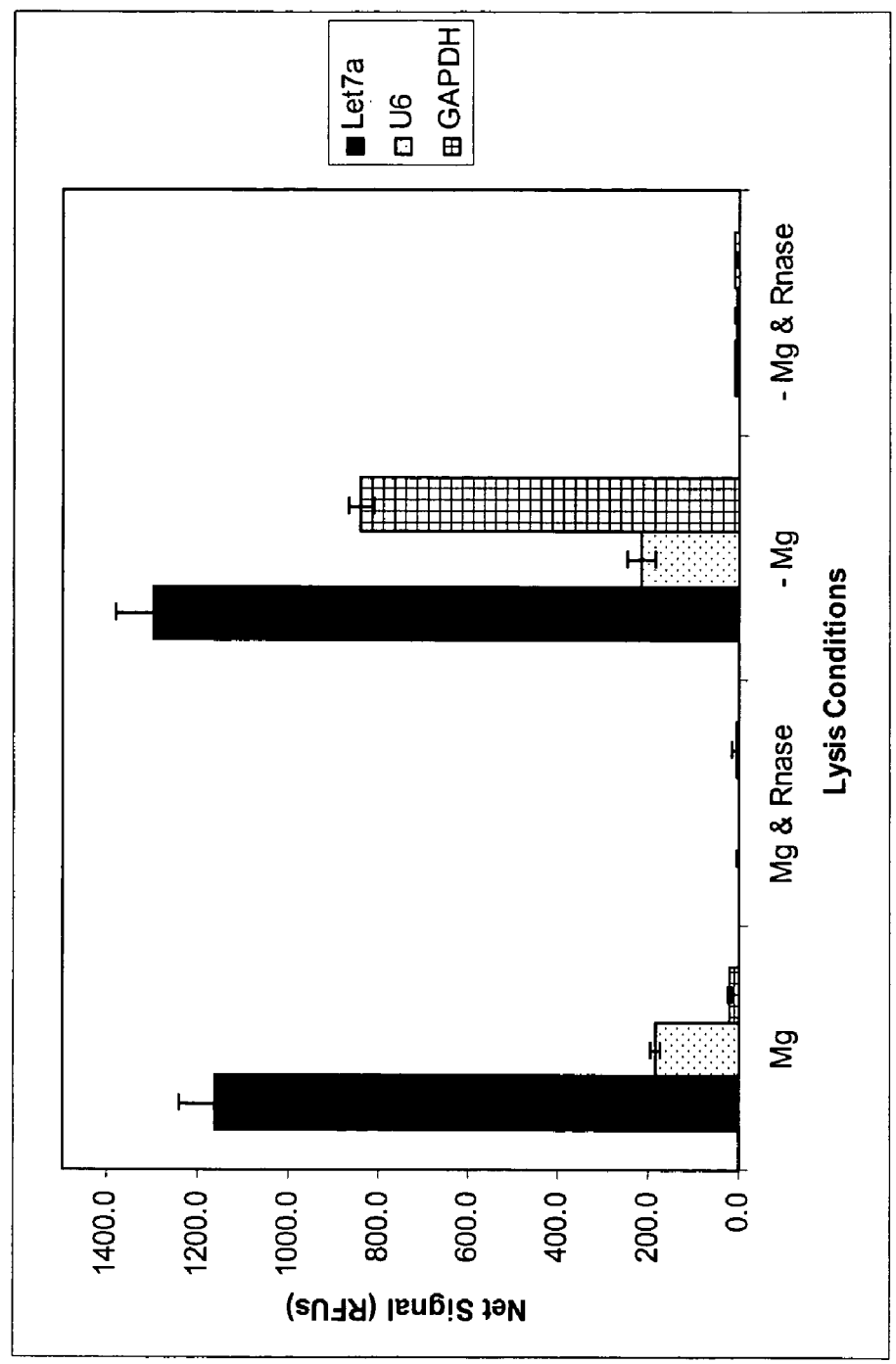
FIG. 16 shows the results of miRNA and miRNA in cell lysates with and without RNAse A treatment.
Figure 17:
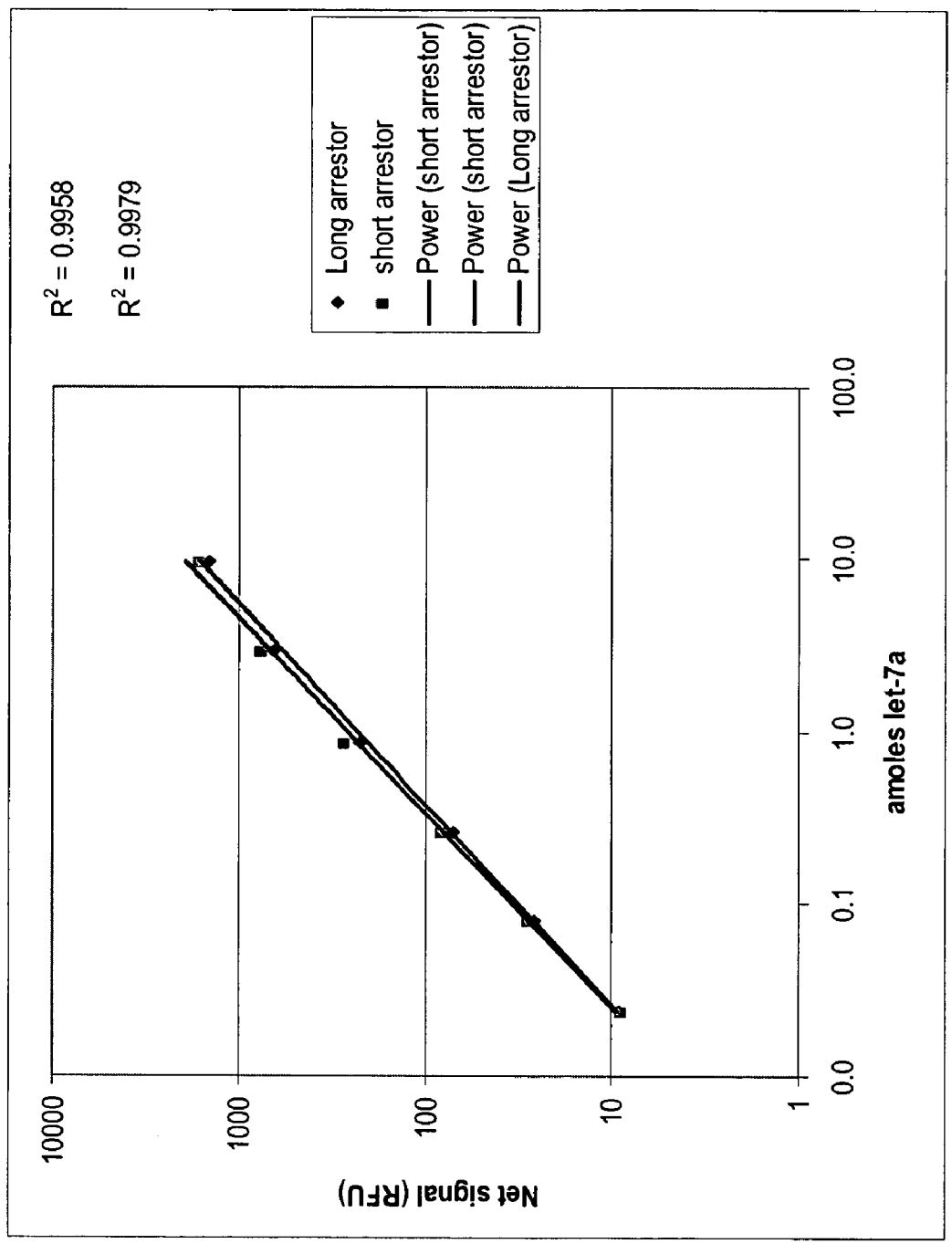
FIG. 17 shows results of invasive cleavage assays comparing the effects of including full-length vs. shortened ARRESTOR oligonucleotides.

In still further embodiments, the detection structures described in FIGS. 16 and 17 are generated. In this embodiment, either probe or INVADER oligonucleotides are extended to create a single hairpin loop or "half dumbbell" structure. In some embodiments, the ends of the oligonucleotides comprise additional nucleic acid sequences that do not hybridize to the miRNA. In some embodiments, these additional sequences form invasive cleavage structures (e.g., INVADER assay invasive cleavage structures). In some embodiments, invasive cleavage structures are detected by the INVADER assay (See e.g., below description).

In other embodiments, these additional sequences are complementary to additional oligonucleotides added to reaction mixtures to stabilize a cleavage structure, e.g. an INVADER assay invasive cleavage structure (FIG. 4).

In some embodiments, circular structures generated as described above are detected using a rolling circle replication assay (See e.g., below description of rolling circle replication).

In still further embodiments, detection structures are generated from long oligonucleotides (e.g., greater than 50, 100, 1000 or more nucleotides) with short region(s) of homology to miRNAs. One or more miRNAs are hybridized to the oligonucleotides to generate detection structures. In some embodiments, these detection structures are detected by extension of miRNAs (e.g., via ligation or polymerization reactions such as RT-PCR). In some embodiments, these detection structures are further detected by hybridization to oligonucleotides conjugated to solid supports, such as microspheres, or other surfaces or structures.

In some embodiments, oligonucleotides used to form detection structures comprise one or more nucleotide analogs. For example, in some embodiments, 2'-O-methyl nucleotides are utilized. The present invention is not limited to a particular mechanism. Indeed, an understanding of the mechanism is not necessary to practice the present invention. Nonetheless, it is contemplated that the presence of 2'-O-methyl bases increases the stability of the hybridized detection structure and aids in further detection methods.

II. Detection of Interfering RNAs

In some embodiments, the present invention provides methods of detecting miRNAs. The present invention is not limited to a particular detection assay. Any suitable method may be utilized including, but not limited to, those disclosed herein.

In some preferred embodiments of the present invention, miRNA detection methods are quantitative. The present invention is not limited to a particular mechanism. Indeed, an understanding of the mechanism is not necessary to practice the present invention. Nonetheless, it is contemplated that levels of a particular miRNA in the body are associated with a level of gene expression from their cognate genes. The present invention thus provides methods of correlated miRNAs with gene expression of particular genes (e.g., genes involved in disease states or metabolism). For example, in some embodiments, the methods of the present invention are utilized to determine the presence of abnormal (e.g., high or low) levels of a particular miRNA or to determine the effect of an intervention (e.g., drug) on miRNA expression. In other embodiments, heterologous miRNAs (e.g., from expression vectors, transgenic constructs, transfection, etc.) are detected to characterize the efficiency of miRNA expression systems.

In some embodiments, the present invention provides methods of detecting a particular miRNA (e.g., a miRNA such as mir-1 or mir-135). In other embodiments, the methods of the present invention are used to distinguish between variants (e.g., polymorphisms or mutations) in a particular miRNA. In still further embodiments, the present invention provides methods of lysing cells to be tested for the presence of miRNAs.

A. INVADER Assay

In some embodiments, the INVADER assay is used for the detection of miRNAs. In some embodiments, the INVADER assay comprises forming a nucleic acid cleavage structure that is dependent upon the presence of a target nucleic acid and cleaving the nucleic acid cleavage structure so as to release distinctive cleavage products. 5' nuclease activity, for example, is used to cleave the target-dependent cleavage structure and the resulting cleavage products or the cleavage of the cleavage structure is indicative of the presence of specific target nucleic acid sequences in the sample. When one or two (or more) strands of nucleic acid, or oligonucleotides, both hybridize to a target nucleic acid strand such that they form an overlapping invasive cleavage structure, as described below, invasive cleavage can occur. Through the interaction of a cleavage agent (e.g., a 5' nuclease) and the upstream oligonucleotide, the cleavage agent can be made to cleave the downstream oligonucleotide at an internal site in such a way that a distinctive fragment is produced. Such embodiments have been termed the INVADER assay (Third Wave Technologies) and are described in U.S. Pat. Nos. 5,846,717, 5,985,557, 5,994,069, 6,001,567, 6,090,543, 6,348,314, and 6,458,535, WO 97/27214 WO 98/42873, Lyamichev et al., Nat. Biotech., 17:292 (1999), Hall et al., PNAS, USA, 97:8272 (2000), each of which is herein incorporated by reference in its entirety for all purposes).

The INVADER assay detects hybridization of probes to a target by enzymatic cleavage of specific structures by structure specific enzymes (See, INVADER assays, Third Wave Technologies; See e.g., U.S. Pat. Nos. 5,846,717; 6,090,543; 6,001,567; 5,985,557; 5,994,069; 6,090,543; 6,348,314; 6,458,535; U.S. Patent App. Nos. 20030186238 (Ser. No. 10/084,839); 20030104378A1 (Ser. No. 09/864,636); Lyamichev et al., Nat. Biotech., 17:292 (1999), Hall et al., PNAS, USA, 97:8272 (2000), WO97/27214 and WO98/42873, each of which is herein incorporated by reference in its entirety for all purposes).

The INVADER assay detects specific DNA and RNA sequences by using structure-specific enzymes (e.g. FEN endonucleases) to cleave a complex formed by the hybridization of overlapping oligonucleotide probes (See, e.g. FIG. 1). Elevated temperature and an excess of one of the probes enable multiple probes to be cleaved for each target sequence present without temperature cycling. In some embodiments, these cleaved probes then direct cleavage of a second labeled probe. The secondary probe oligonucleotide can be 5'-end labeled with fluorescein that is quenched by an internal dye. Upon cleavage, the de-quenched fluorescein labeled product may be detected using a standard fluorescence plate reader.

The INVADER assay detects specific sequences, mutations, and SNPs in unamplified, as well as amplified, RNA and DNA, including genomic DNA. In the embodiments shown schematically in FIG. 1, the INVADER assay uses two cascading steps (a primary and a secondary reaction) both to generate and then to amplify the target-specific signal. For convenience, the alleles in the following discussion are described as wild-type (WT) and mutant (MT), even though this terminology does not apply to all genetic variations. In the primary reaction (FIG. 1, panel A), the WT primary probe and the INVADER oligonucleotide hybridize in tandem to the target nucleic acid to form an overlapping structure. An unpaired "flap" is included on the 5' end of the WT primary probe. A structure-specific enzyme (e.g. the CLEAVASE enzyme, Third Wave Technologies) recognizes the overlap and cleaves off the unpaired flap, releasing it as a target-specific product. In the secondary reaction, this cleaved product serves as an INVADER oligonucleotide on the WT fluorescence resonance energy transfer (WT-FRET) probe to again create the structure recognized by the structure specific enzyme (panel A). When the two dyes on a single FRET probe are separated by cleavage (indicated by the arrow in FIG. 1), a detectable fluorescent signal above background fluorescence is produced. Consequently, cleavage of this second structure results in an increase in fluorescence, indicating the presence of the WT allele (or mutant allele if the assay is configured for the mutant allele to generate the detectable signal). In some embodiments, FRET probes having different labels (e.g. resolvable by difference in emission or excitation wavelengths, or resolvable by time-resolved fluorescence detection) are provided for each allele or locus to be detected, such that the different alleles or loci can be detected in a single reaction. In such embodiments, the primary probe sets and the different FRET probes may be combined in a single assay, allowing comparison of the signals from each allele or locus in the same sample.

If the primary probe oligonucleotide and the target nucleotide sequence do not match perfectly at the cleavage site (e.g., as with the MT primary probe and the WT target, FIG. 1, panel B), the overlapped structure does not form and cleavage is suppressed. The structure specific enzyme (e.g., CLEAVASE VIII enzyme, Third Wave Technologies) used cleaves the overlapped structure more efficiently (e.g. at least 340-fold) than the non-overlapping structure, allowing excellent discrimination of the alleles.

The probes turn over without temperature cycling to produce many signals per target (i.e., linear signal amplification). Similarly, each target-specific product can enable the cleavage of many FRET probes.

The primary INVADER assay reaction is directed against the target DNA (or RNA) being detected. The target DNA is the limiting component in the first invasive cleavage, since the INVADER and primary probe are supplied in molar excess. In the second invasive cleavage, it is the released flap that is limiting. When these two cleavage reactions are performed sequentially, the fluorescence signal from the composite reaction accumulates linearly with respect to the target DNA amount.

In certain embodiments, the INVADER assay, or other nucleotide detection assays, are performed with accessible site-designed oligonucleotides and/or bridging oligonucleotides. Such methods, procedures and compositions are described in U.S. Pat. Nos. 6,194,149, 6,358,691, 6,355,437, U.S. patent application Ser. No. 09/882,945, and PCT Applications WO9850403, and WO0198537, all of which are specifically incorporated by reference in their entireties.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some embodiments, the target sequence comprises a first region and a second region, the second region downstream of and contiguous to the first region, and the oligonucleotides comprise first and second oligonucleotides, wherein at least a portion of the first oligonucleotide is completely complementary to the first portion of the target sequence and wherein the second oligonucleotide comprises a 3' portion and a 5' portion, wherein the 5' portion is completely complementary to the second portion of the target nucleic acid.

In some preferred embodiments, the exposing of the sample to the oligonucleotides and the agent comprises exposing the sample to the oligonucleotides and the agent under conditions wherein an invasive cleavage structure is formed between the target sequence and the oligonucleotides if the target sequence is present in the sample, wherein the invasive cleavage structure is cleaved by the cleavage agent to form a cleavage product.

In some preferred embodiments, the exposing of the sample to the oligonucleotides and the agent comprises exposing the sample to the oligonucleotides and the agent under conditions wherein an invasive cleavage structure is formed between said target sequence and said oligonucleotides if said target sequence is present in said sample, wherein said invasive cleavage structure is cleaved by said cleavage agent to form a cleavage product.

In some particularly preferred embodiments, the target sequence comprises a first region and a second region, said second region downstream of and contiguous to said first region, and said oligonucleotides comprise first and second oligonucleotides, wherein at least a portion of said first oligonucleotide is completely complementary to said first portion of said target sequence and wherein said second oligonucleotide comprises a 3' portion and a 5' portion, wherein said 5' portion is completely complementary to said second portion of said target nucleic acid.

In certain embodiments, the present invention provides kits for assaying a pooled sample (e.g., a pooled blood sample or pooled cell lysates) using INVADER detection reagents (e.g. primary probe, INVADER probe, and FRET cassette). In preferred embodiments, the kit further comprises instructions on how to perform the INVADER assay, and in some embodiments, how to apply the INVADER detection assay to pooled samples from many individuals, or to "pooled" samples from many cells (e.g., from a biopsy sample) from a single subject.

The present invention further provides assays in which the target nucleic acid is reused or recycled during multiple rounds of hybridization with oligonucleotide probes and cleavage of the probes without the need to use temperature cycling (i.e., for periodic denaturation of target nucleic acid strands) or nucleic acid synthesis (i.e., for the polymerization-based displacement of target or probe nucleic acid strands). When a cleavage reaction is run under conditions in which the probes are continuously replaced on the target strand (e.g. through probe-probe displacement or through an equilibrium between probe/target association and disassociation, or through a combination comprising these mechanisms, (Reynaldo et al., J. Mol. Biol. 97: 511-520 (2000)), multiple probes can hybridize to the same target, allowing multiple cleavages, and the generation of multiple cleavage products.

The INVADER Assay Reaction:

In preferred embodiments of the INVADER DNA assay, two oligonucleotides (a discriminatory Primary Probe and an INVADER Oligo) hybridize in tandem to the target DNA to form an overlapping structure. The 5'-end of the Primary Probe includes a 5'-flap that does not hybridize to the target DNA (FIG. 1). The 3'-nucleotide of the bound INVADER oligonucleotide overlaps the Primary Probe, but need not hybridize to the target DNA. The CLEAVASE enzyme recognizes this overlapping structure and cleaves off the unpaired 5'-flap of the Primary Probe, releasing it as a target-specific product. The Primary Probe is designed to have a melting temperature close to the reaction temperature. Thus, under the isothermal assay conditions, Primary Probes, which are provided in excess, cycle on the target DNA. This allows for multiple rounds of Primary Probe cleavage for each target DNA, and amplification of the number of released 5'-flaps.

In the secondary reaction, each released 5'-flap can serve as an INVADER oligonucleotide on a fluorescence resonance energy transfer (FRET) Cassette to create another overlapping structure that is recognized and cleaved by the CLEAVASE enzyme (FIG. 1). When the FRET Cassette is cleaved, the fluorophore (F) and quencher (Q) are separated, generating detectable fluorescence signal. Similar to the initial reaction, the released 5'-flap and the FRET Cassette cycle, resulting in amplified fluorescence signal. The initial and secondary reactions run concurrently in the same well.

The biplex format of the INVADER DNA Assay enables simultaneous detection of two DNA sequences in a single well. Most often, this involves detection of two variants of a particular polymorphism (e.g., in a miRNA). The biplex format uses two different discriminatory Primary Probes, each with a unique 5'-flap, and two different FRET Cassettes, each with a spectrally distinct fluorophore. By design, the released 5'-flaps will bind only to their respective FRET Cassettes to generate a target-specific signal.

In some embodiments, the present invention provides kits comprising one or more of the components necessary for practicing the present invention. For example, the present invention provides kits for storing or delivering the enzymes of the present invention and/or the reaction components necessary to practice a cleavage assay (e.g., the INVADER assay). By way of example, and not intending to limit the kits of the present invention to any particular configuration or combination of components, the following section describes one embodiment of a kit for practicing the present invention:

In some embodiments, the kits of the present invention provide the following reagents:

| | |
|---|---|
| CLEAVASE enzyme | Primary Probe Oligos |
| DNA Reaction Buffer 1 | INVADER Oligo |
| | FRET Cassette 1 (e.g., F) |
| | FRET Cassette 2 (e.g., R) |
| | Mutant DNA controls |
| | Wild type DNA controls |
| | "No Target" Blank control |

In other embodiments, the kits of the present invention are configured for direct detection of RNA. These kits may provide the following reagents:

| | |
|---|---|
| CLEAVASE enzyme | Primary Probe oligonucleotides |
| DNA Reaction Buffer 1 | INVADER Oligo |
| | FRET Probe 1 (e.g., F) |
| | FRET Probe 2 (e.g., R) |
| | Secondary Reaction Target 1 |
| | Secondary Reaction Target 2 |
| | ARRESTOR oligonucleotide 1 |
| | ARRESTOR oligonucleotide 2 |
| | Mutant DNA controls |
| | Wild type DNA controls |
| | "No Target" Blank control |

An additional consideration has to do with undesired effects resulting from particular combinations of oligonucleotides in a single reaction. One such effect is target-independent generation of background signal. Certain oligonucleotides in combination with others may generate signal in the INVADER assay in the absence of the particular target being detected. Separation of these oligonucleotide combinations into different pools can be used to alleviate this effect. Similarly, certain oligonucleotide combinations can artificially repress signal generation from a desired target. Again, separation of these combinations into different pools can alleviate this effect.

The designs of the probes sets (e.g., the oligonucleotides and/or their sequences) are adapted for use in miRNA detection assays using the guidelines for reaction design and optimization provided herein (See e.g., the Experimental Section). For example, in some embodiments, the reaction temperature is reduced (e.g., to 50-60° C.) to account for the smaller region of hybridization.

In some embodiments, a kit of the present invention provides a list of additional components (e.g., reagents, supplies, and/or equipment) to be supplied by a user in order to perform the methods of the invention. For example, and without intending to limit such additional components lists to any particular components, one embodiment of such a list comprises the following:

Clear CHILLOUT-14 liquid wax (MJ Research) or RNase-free, optical grade mineral oil (Sigma, Cat. No. M-5904)

96-well polypropylene microplate (MJ Research, Cat. No. MSP-9601)

Sterile 1.5-ml or 2.0-ml microcentrifuge tubes

Sterile, DNase/RNase free disposable aerosol barrier pipet tips

Multichannel pipets (0.5-10 µl, 2.5-20 µl)

Thermal cycler or other heat source (e.g., lab oven or heating block).

Miscellaneous laboratory equipment (tube racks, micropipetors, multichannel pipet, microcentrifuge, vortex mixer).

Fluorescence microplate reader (a preferred plate reader is top-reading and equipped with light filters have the following characteristics:

| Excitation (Wavelength/Bandwidth) | Emission (Wavelength/Bandwidth) |
|---|---|
| 485 nm/20 nm | 530 nm/25 nm |
| 560 nm/20 nm | 620 nm/40 nm |

In some embodiments, a kit of the present invention provides a list of optional components (e.g., reagents, supplies, and/or equipment) to be supplied by a user to facilitate performance of the methods of the invention. For example, and without intending to limit such optional components lists to any particular components, one embodiment of such a list comprises the following:

Sterile 8-tube strip or microplate (optional)

Disposable plastic trough (optional)

Plate sealing tape (optional)

In some embodiments, a kit of the present invention provides a list of required components to be supplied by a user to facilitate performance of the methods of the invention for which multiple alternatives are acceptable (e.g. sample preparation kits). For example, and without intending to limit such optional components lists to any particular components, one embodiment of such a list comprises the following:

QIAGEN QIAAMP Blood Kit

Gentra Systems PUREGENE Kit

Gentra Systems GENERATION Products

In some embodiments of a kit, detailed protocols are provided. In preferred embodiments, protocols for the assembly of INVADER assay reactions (e.g., formulations and preferred procedures for making reaction mixtures) are provided. In particularly preferred embodiments, protocols for assembly of reaction mixtures include computational or graphical aids to reduce risk of error in the performance of the methods of the present invention (e.g., tables to facilitate calculation of volumes of reagents needed for multiple reactions, and plate-layout guides to assist in configuring multi-well assay plates to contain numerous assay reactions).

In some embodiments, supplementary documentation, such as protocols for ancillary procedures, e.g., for the preparation of additional reagents, or for preparation of samples for use in the methods of the present invention, are provided. In preferred embodiments, supplementary documentation includes guidelines and lists of precautions provided to facilitate successful use of the methods and kits by unskilled or inexperienced users. In particularly preferred embodiments, supplementary documentation includes a troubleshooting guide, e.g., a guide describing possible problems that may be encountered by users, and providing suggested solutions or corrections to intended to aid the user in resolving or avoiding such problems.

In preferred embodiments, samples are diluted to concentrations that correspond to a 10-μl addition per reaction. The concentration of a 100-ng sample should be 15 ng/μl.

B. Rolling Circle Replication

In other embodiments, rolling circle replication methods (Amersham Biosciences, Piscataway, N.J.) are utilized for detection of miRNA detection structures (See e.g., U.S. Pat. Nos. 6,344,329; 6,143,495; 6,316,229; 6,210,884, 6,183,960 and 6,235,502; each of which is herein incorporated by reference). In some embodiments, rolling circle replication is used to detect circular miRNA detection structures generated from the annealing of the ends of a single oligonucleotide annealed to a miRNA. In some embodiments, the ends of the oligonucleotide hybridize to the miRNA with no overlap. This oligonucleotide can be ligated in the presence or absence of miRNA. However, the ligation reaction is more efficient in the presence of the miRNA. In such embodiments, the level of circular molecules detected over time is compared to a control reaction lacking miRNA.

In other embodiments, the ends of the oligonucleotide hybridize to the miRNA with overlapping ends to generate an invasive cleavage structure. Such structures are cleaved prior to ligation, thus improving the specificity of the generation of the circular detection structure.

Rolling circle amplification (RCA) involves replication of circular single-stranded DNA molecules. In RCA, a rolling circle replication primer hybridizes to circular nucleic acid molecules followed by rolling circle replication of the nucleic acid molecules using a strand-displacing DNA polymerase. Amplification takes place during rolling circle replication in a single reaction cycle. Rolling circle replication results in large DNA molecules containing tandem repeats of the nucleic acid sequence. This DNA molecule is referred to as a tandem sequence DNA (TS-DNA).

In some embodiments, ligation-mediated rolling circle amplification (LM-RCA), which involves a ligation operation prior to replication, is utilized. In the ligation operation, an probe hybridizes to its cognate target nucleic acid sequence, if present, followed by ligation of the ends of the hybridized probe to form a covalently closed, single-stranded nucleic acid. After ligation, a rolling circle replication primer hybridizes to probe molecules followed by rolling circle replication of the circular molecules using a strand-displacing DNA polymerase. Generally, LM-RCA comprises mixing an open circle probe with a target sample, resulting in an probe-target sample mixture, and incubating the probe-target sample mixture under conditions promoting hybridization between the open circle probe and a target sequence, mixing ligase with the probe-target sample mixture, resulting in a ligation mixture, and incubating the ligation mixture under conditions promoting ligation of the open circle probe to form an amplification target circle (ATC), mixing a rolling circle replication primer (RCRP) with the ligation mixture, resulting in a primer-ATC mixture, and incubating the primer-ATC mixture under conditions that promote hybridization between the amplification target circle and the rolling circle replication primer, mixing DNA polymerase with the primer-ATC mixture, resulting in a polymerase-ATC mixture, and incubating the polymerase-ATC mixture under conditions promoting replication of the amplification target circle, where replication of the amplification target circle results in formation of tandem sequence DNA (TS-DNA).

C. Additional Detection Methods

The present invention is not limited to INVADER assay or rolling circle assay detection. Any method that allows for the detection of miRNA detection structures may be utilized. Exemplary, non-limiting detection assay that find use in the methods of the present invention are described below.

1. Hybridization Assays

In some embodiments of the present invention, detection structures are detected using a hybridization assay. In a hybridization assay, the presence of absence of a given nucleic acid sequence is determined based on the ability of the DNA from the sample to hybridize to a complementary DNA molecule (e.g., a oligonucleotide probe). A variety of hybridization assays using a variety of technologies for hybridization and detection are available. A description of a selection of assays is provided below.

a. Direct Detection of Hybridization

In some embodiments, hybridization of a probe to the sequence of interest (e.g., a SNP or mutation) is detected directly by visualizing a bound probe (e.g., a Northern or Southern assay; See e.g., Ausabel et al. (eds.), Current Protocols in Molecular Biology, John Wiley & Sons, NY [1991]). In a these assays, genomic DNA (Southern) or RNA (Northern) is isolated from a subject. The DNA or RNA is then cleaved with a series of restriction enzymes that cleave infrequently in the genome and not near any of the markers being assayed. The DNA or RNA is then separated (e.g., on an agarose gel) and transferred to a membrane. A labeled (e.g., by incorporating a radionucleotide) probe or probes specific for the SNP or mutation being detected is allowed to contact the membrane under a condition of low, medium, or high stringency conditions. Unbound probe is removed and the presence of binding is detected by visualizing the labeled probe.

b. Detection of Hybridization Using "DNA Chip" Assays

In some embodiments of the present invention, variant sequences are detected using a DNA chip hybridization assay. In this assay, a series of oligonucleotide probes are affixed to a solid support. The oligonucleotide probes are designed to be unique to a given target sequence (e.g., miRNA target sequence). The DNA sample of interest is contacted with the DNA "chip" and hybridization is detected.

In some embodiments, the DNA chip assay is a GeneChip (Affymetrix, Santa Clara, Calif.; See e.g., U.S. Pat. Nos. 6,045,996; 5,925,525; and 5,858,659; each of which is herein incorporated by reference) assay. The GeneChip technology uses miniaturized, high-density arrays of oligonucleotide probes affixed to a "chip." Probe arrays are manufactured by Affymetrix's light-directed chemical synthesis process, which combines solid-phase chemical synthesis with photolithographic fabrication techniques employed in the semiconductor industry. Using a series of photolithographic masks to define chip exposure sites, followed by specific chemical synthesis steps, the process constructs high-density arrays of oligonucleotides, with each probe in a predefined position in the array. Multiple probe arrays are synthesized simultaneously on a large glass wafer. The wafers are then diced, and individual probe arrays are packaged in injection-molded plastic cartridges, which protect them from the environment and serve as chambers for hybridization.

The nucleic acid to be analyzed is isolated, amplified by PCR, and labeled with a fluorescent reporter group. The labeled DNA is then incubated with the array using a fluidics station. The array is then inserted into the scanner, where patterns of hybridization are detected. The hybridization data are collected as light emitted from the fluorescent reporter groups already incorporated into the target, which is bound to the probe array. Probes that perfectly match the target generally produce stronger signals than those that have mismatches. Since the sequence and position of each probe on the array are known, by complementarity, the identity of the target nucleic acid applied to the probe array can be determined.

In other embodiments, a DNA microchip containing electronically captured probes (Nanogen, San Diego, Calif.) is utilized (See e.g., U.S. Pat. Nos. 6,017,696; 6,068,818; and 6,051,380; each of which are herein incorporated by reference). Through the use of microelectronics, Nanogen's technology enables the active movement and concentration of charged molecules to and from designated test sites on its semiconductor microchip. DNA capture probes unique to a given target sequence are electronically placed at, or "addressed" to, specific sites on the microchip. Since DNA has a strong negative charge, it can be electronically moved to an area of positive charge.

First, a test site or a row of test sites on the microchip is electronically activated with a positive charge. Next, a solution containing the DNA probes is introduced onto the microchip. The negatively charged probes rapidly move to the positively charged sites, where they concentrate and are chemically bound to a site on the microchip. The microchip is then washed and another solution of distinct DNA probes is added until the array of specifically bound DNA probes is complete.

A test sample is then analyzed for the presence of target sequences by determining which of the DNA capture probes hybridize, with target sequences. An electronic charge is also used to move and concentrate target molecules to one or more test sites on the microchip. The electronic concentration of sample DNA at each test site promotes rapid hybridization of sample DNA with complementary capture probes (hybridization may occur in minutes). To remove any unbound or nonspecifically bound DNA from each site, the polarity or charge of the site is reversed to negative, thereby forcing any unbound or nonspecifically bound DNA back into solution away from the capture probes. A laser-based fluorescence scanner is used to detect binding.

In still further embodiments, an array technology based upon the segregation of fluids on a flat surface (chip) by differences in surface tension (ProtoGene, Palo Alto, Calif.) is utilized (See e.g., U.S. Pat. Nos. 6,001,311; 5,985,551; and 5,474,796; each of which is herein incorporated by reference). Protogene's technology is based on the fact that fluids can be segregated on a flat surface by differences in surface tension that have been imparted by chemical coatings. Once so segregated, oligonucleotide probes are synthesized directly on the chip by ink-jet printing of reagents. The array with its reaction sites defined by surface tension is mounted on a x/Y translation stage under a set of four piezoelectric nozzles, one for each of the four standard DNA bases. The translation stage moves along each of the rows of the array and the appropriate reagent is delivered to each of the reaction sites. For example, the A amidite is delivered only to the sites where amidite A is to be coupled during that synthesis step and so on. Common reagents and washes are delivered by flooding the entire surface and then removing them by spinning.

DNA probes unique for the target sequence (e.g., miRNA target sequence) of interest are affixed to the chip using Protogene's technology. The chip is then contacted with the PCR-amplified genes of interest. Following hybridization, unbound DNA is removed and hybridization is detected using any suitable method (e.g., by fluorescence de-quenching of an incorporated fluorescent group).

In yet other embodiments, a "bead array" is used for the detection of polymorphisms (Illumina, San Diego, Calif.; See e.g., PCT Publications WO 99/67641 and WO 00/39587, each of which is herein incorporated by reference). Illumina uses a BEAD ARRAY technology that combines fiber optic bundles and beads that self-assemble into an array. Each fiber optic bundle contains thousands to millions of individual fibers depending on the diameter of the bundle. The beads are coated with an oligonucleotide specific for the detection of a given SNP or mutation. Batches of beads are combined to form a pool specific to the array. To perform an assay, the BEAD ARRAY is contacted with a prepared subject sample (e.g., nucleic acid sample). Hybridization is detected using any suitable method.

c. Enzymatic Detection of Hybridization

In some embodiments of the present invention, hybridization is detected by enzymatic cleavage of specific structures.

In some embodiments, hybridization of a bound probe is detected using a TaqMan assay (PE Biosystems, Foster City, Calif.; See e.g., U.S. Pat. Nos. 5,962,233 and 5,538,848, each of which is herein incorporated by reference). The assay is performed during a PCR reaction. The TaqMan assay exploits the 5'-3' exonuclease activity of the AMPLITAQ GOLD DNA polymerase. A probe, specific for a given allele or mutation, is included in the PCR reaction. The probe consists of an oligonucleotide with a 5'-reporter dye (e.g., a fluorescent dye) and a 3'-quencher dye. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In still further embodiments, polymorphisms are detected using the SNP-IT primer extension assay (Orchid Biosciences, Princeton, N.J.; See e.g., U.S. Pat. Nos. 5,952,174 and 5,919,626, each of which is herein incorporated by reference). In this assay, SNPs are identified by using a specially synthesized DNA primer and a DNA polymerase to selectively extend the DNA chain by one base at the suspected SNP location. DNA in the region of interest is amplified and denatured. Polymerase reactions are then performed using miniaturized systems called microfluidics. Detection is accomplished by adding a label to the nucleotide suspected of being at the target sequence location. Incorporation of the label into the DNA can be detected by any suitable method (e.g., if the nucleotide contains a biotin label, detection is via a fluorescently labeled antibody specific for biotin).

2. Other Detection Assays

Additional detection assays useful in the detection of miRNA detection structures include, but are not limited to, enzyme mismatch cleavage methods (e.g., Variagenics, U.S. Pat. Nos. 6,110,684, 5,958,692, 5,851,770, herein incorporated by reference in their entireties); polymerase chain reaction; branched hybridization methods (e.g., Chiron, U.S. Pat. Nos. 5,849,481, 5,710,264, 5,124,246, and 5,624,802, herein incorporated by reference in their entireties); NASBA (e.g., U.S. Pat. No. 5,409,818, herein incorporated by reference in its entirety); molecular beacon technology (e.g., U.S. Pat. No. 6,150,097, herein incorporated by reference in its entirety); E-sensor technology (Motorola, U.S. Pat. Nos. 6,248,229, 6,221,583, 6,013,170, and 6,063,573, herein incorporated by reference in their entireties); cycling probe technology (e.g., U.S. Pat. Nos. 5,403,711, 5,011,769, and 5,660,988, herein incorporated by reference in their entireties); Dade Behring signal amplification methods (e.g., U.S. Pat. Nos. 6,121,001, 6,110,677, 5,914,230, 5,882,867, and 5,792,614, herein incorporated by reference in their entireties); ligase chain reaction (Barnay Proc. Natl. Acad. Sci USA 88, 189-93 (1991)); and sandwich hybridization methods (e.g., U.S. Pat. No. 5,288,609, herein incorporated by reference in its entirety).

EXPERIMENTAL

The following examples are provided in order to demonstrate and further illustrate certain preferred embodiments and aspects of the present invention and are not to be construed as limiting the scope thereof.

Example 1

Materials and Methods

The following final concentrations (unless noted) were used for all reactions:
Probe=1 µM
INVADER=1 µM
ARRESTOR=2.67 µM
CLEAVASE XII enzyme=30 ng All synthetic miRNA oligonucleotides were purchased from Dharmacon and gel purified on 20% denaturing acrylamide. Synthetic miRNAs were used to determine temperature optima (see below) and LOD.

INVADER, probe, and ARRESTOR oligonucleotides were synthesized either by Integrated DNA Technologies (IDT) or Third Wave Technologies and purified on 20% denaturing acrylamide, unless otherwise indicated.

The following 2.5 X primary reaction buffer was used (unless otherwise noted) for all reactions:
25 mM MOPS pH 7.5
62.5 mM KCl
0.125% Tween 20
0.125% Nonidet NP40
62.5 mM MgSO$_4$
5% PEG Unless otherwise noted, all reactions were overlaid with 10 µl mineral oil prior to the first thermal incubation.

Unless otherwise noted, synthetic miRNAs contained a 5'OH. Experiments comparing detection of 5' phosphorylated vs. unphosphorylated synthetic miRNA targets indicated that there was no significant difference in the ability of the INVADER assay to detect these two different types of synthetic molecules.

Example 2

Temperature Optimization Experiments for let-7 and mir-1

The oligonucleotide design for let-7 is shown in FIG. 5. The oligonucleotide design for mir-1 is shown in FIG. 5. The following primary mixes were made and incubated at 50° C.±10° C. in a 96 well plate for 30 minutes. In addition, a no target master mix was prepared (addition of H$_2$O in place of RNA). All reactions were covered with mineral oil to prevent evaporation.

| Primary Reaction Components | Stock Concentration | Amount Added |
|---|---|---|
| Primary Reaction Buffer | 2.5× | 4 µl |
| Probe oligonucleotide (SEQ ID NOs: 2, 6, or 9 for let 7; SEQ ID NOs: 12, 16, or 19 for miR-1) | 10 µM | 1 µl |
| INVADER oligonucleotide (SEQ ID NOs: 1, 5, or 8 for let 7; SEQ ID NOs: 11, 15, or 18 for miR-1) | 10 µM | 1 µl |
| CLEAVASE IX or XII enzyme | 40 ng/µl CLEAVASE IX enzyme or 60 ng/µl CLEAVASE XII enzyme | 0.5 µl |
| tRNA | 20 ng/µl | 1.5 µl |
| Synthetic miRNA (SEQ ID NO: 4 for let-7a; SEQ ID NO: 14 for miR-1) | 100 pM | 2 µl |
| Total | | 10 µl |

After completion of the primary reaction, 5 µl of the following secondary reaction mix were added and the reaction was then reaction incubated at 60° C. for 10-15 minutes.

| Secondary Reaction Components | Stock Concentration | Amount Added |
|---|---|---|
| H$_2$O (or buffer for CLEAVASE IX enzyme assays) | | 2 µl |
| FAM FRET probe (SEQ ID NO: 21) | 10 µM | 1 µl |
| Secondary Reaction Target (SEQ ID NO: 22 for let-7; SEQ ID NO: 40 for miR-1) | 1.5 µM | 1 µl |
| ARRESTOR Oligonucletide (SEQ ID NOs: 3, 7, or 10 for let-7; SEQ ID NOs: 13, 17, or 20 for miR-1) | 40 µM | 1 µl |
| Total | | 5 µl |

Figure 7:
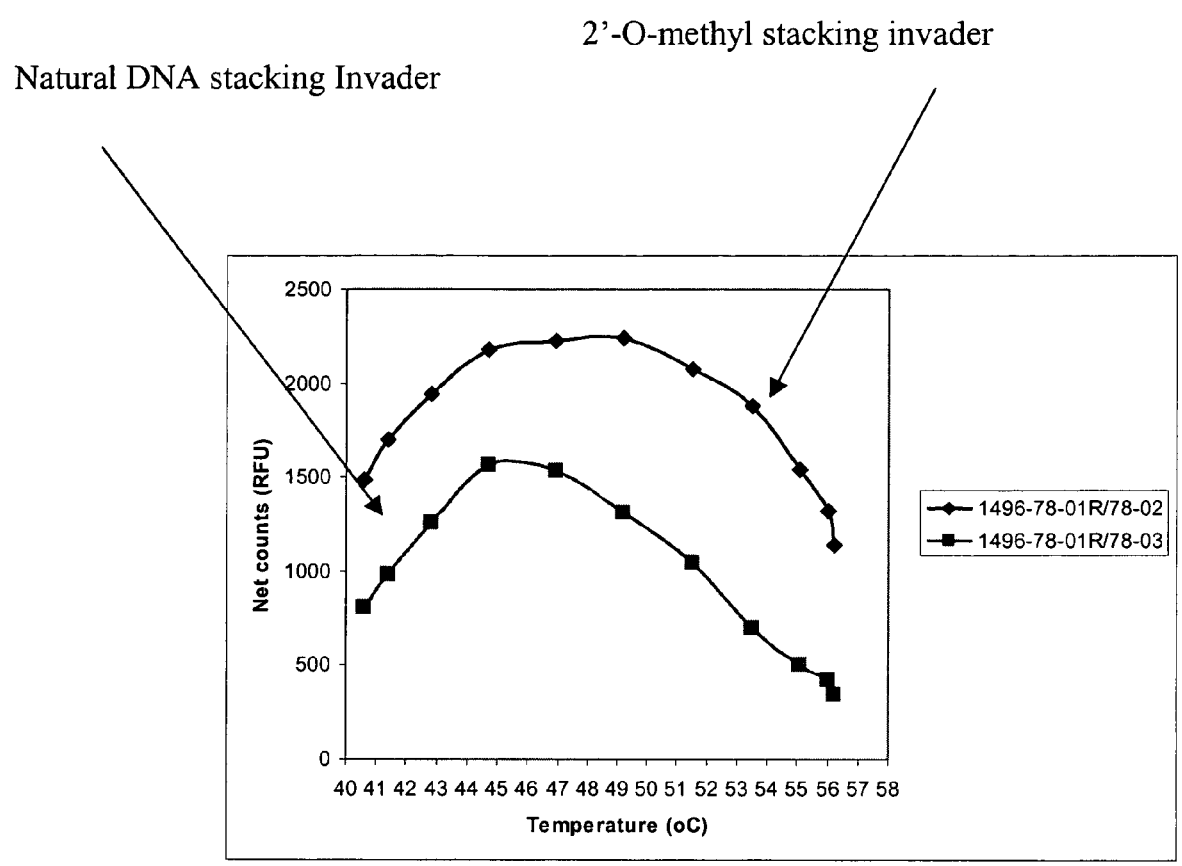
FIG. 7 shows the results of temperature optimization experiments for let-7.

After completion of the reaction, the plate was read in a CYTOFLUOR 4000 fluorescence microplate reader using an excitation wavelength of 485 nm and emission wavelength of 530 nm. Results are shown in FIGS. 6 and 7. Stacking of the 5'-end of the INVADER oligonucleotide to the 3'-end of the miRNA is enhanced when the 3'-end of the INVADER oligonucleotide is 2'-O-methylated. In addition, 2'-O-methylation of the 5'-end of the INVADER oligonucleotide increases the reaction temperature. Extending the 2'-O-methylated bases of the INVADER oligonucleotide so that they base pair with the first two bases of the miRNA (SEQ ID NO: 8 (1496-96-O$_2$) vs. SEQ ID NO: 23 (1496-96-03) in design SEQ ID NO: 9 (1496-96-01R) of let-7a) increases the temperature optimum of the described reaction but does not enhance the detection.

Example 3

LOD Experiments for let-7 and miR-1

After determining the optimal reaction temperature for each set of probe and INVADER oligonucleotides and determining the best working design (from the temperature optimization net signal), the following experiment was set up to determine the LOD of the design using synthetic RNA. The following reaction mix was aliquoted into a 96-well plate (see plate setup below) with each well containing:

| Component | Stock conc. | Amount Added |
|---|---|---|
| Primary reaction buffer | 2.5× | 4 µl |
| Probe SEQ ID NO: 6 for let 7 SEQ ID NO: 16 or 19 for miR-1 | 10 µM | 1 µl |
| INVADER oligo SEQ ID NO: 5 for let 7 SEQ ID NO: 15 or 18 for miR-1 | 10 µM | 1 µl |
| CLEAVASE XII enzyme | 60 ng/µl | 0.5 µl |
| TRNA | 20 ng/µl | 1 µl |
| TOTAL | | 7.5 µl |

2.5 µl of the following miRNA concentrations were added in triplicates or quadruplicates using the following setup:

| | <------[miRNA]----> | | | | | |
|---|---|---|---|---|---|---|
| | 1 nM | 100 pM | 10 pM | 1 pM | 100 fM | 10 fM | H2O |
| A | | | | | | | |
| B | | | | | | | |
| C | | | | | | | |
| D | | | | | | | |

The plate was overlayed with mineral oil (10 µl) and incubated at 50° C. for 2 hrs. After completion of the primary reaction, 5 µl of the following was added to each well and the plates were incubated at 60° C. for 1.5 hrs. The plate was read using the settings described above (see Example 2).

| Secondary Reaction Components | Stock Conc. | Amount Added |
|---|---|---|
| H$_2$O (or buffer for CLEAVASE IX enzyme assays) | | 2 µl |
| FAM FRET Probe (SEQ ID NO: 21) | 10 µM | 1 µl |
| Secondary Target (SEQ ID NO: 22 for let-7; SEQ ID NO: 40 for miR-1) | 1.5 µM | 1 µl |
| ARRESTOR oligonucleotide (SEQ ID NO: 7 for let 7; SEQ ID NOs: 17 or 20 for miR-1) | 40 µM | 1 µl |
| Total | | 5 µl |

Figure 10:
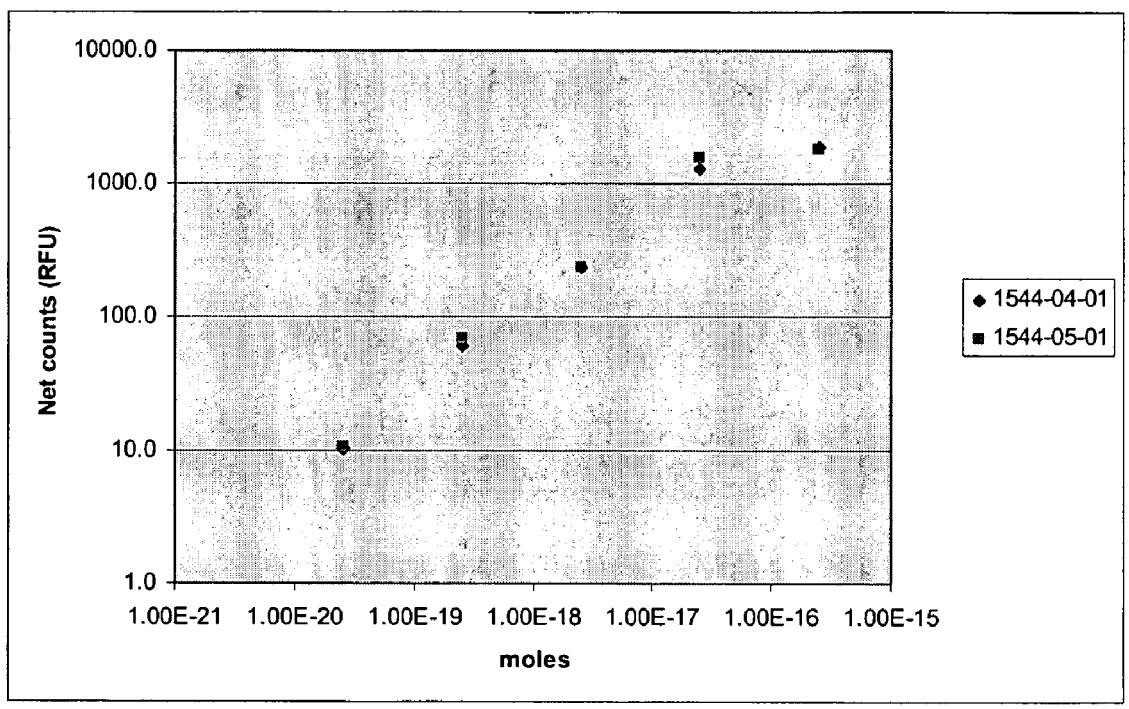
FIG. 10 shows the results of LOD experiments for miR-1.

The LOD for let-7 and mir-1 was next tested on human RNA samples. The protocol described above was utilized. 50-100 ng of tissue specific total human RNA samples (Clonetech, Palo Alto, Calif.) was used. Results are shown in FIGS. 8 and 10. Using total RNA the let-7a INVADER assay detects the same tissue expression profile as seen before for let-7a expression levels depending on the source of tissue (Pasquinelli et al., 408:86 [2000]).

Example 4

Cross Reactivity Experiments for let-7 a,c,e, and f

This Example describes an analysis of the cross reactivity of probe and/or INVADER oligonucleotides directed against one sub-type of let-7 for another sub-type. The protocol for synthetic let-7a miRNA setup described in Example 3 was utilized. FIG. 5 shows the oligonucleotide designs. The following plate setup was used:

| | | 10 nM 1 | 1 nM 2 | 100 pM 3 | 10 pM 4 | 1 pM 5 | 100 fM 6 | 10 fM 7 | H2O 8 |
|---|---|---|---|---|---|---|---|---|---|
| Let 7 A | A | | | | | | | | |
| Let 7 A | B | | | | | | | | |
| Let 7 C | C | | | | | | | | |
| Let 7 C | D | | | | | | | | |
| Let 7 E | E | | | | | | | | |
| Let 7 E | F | | | | | | | | |
| Let 7 F | G | | | | | | | | |
| Let 7 F | H | | | | | | | | |

Figure 9:
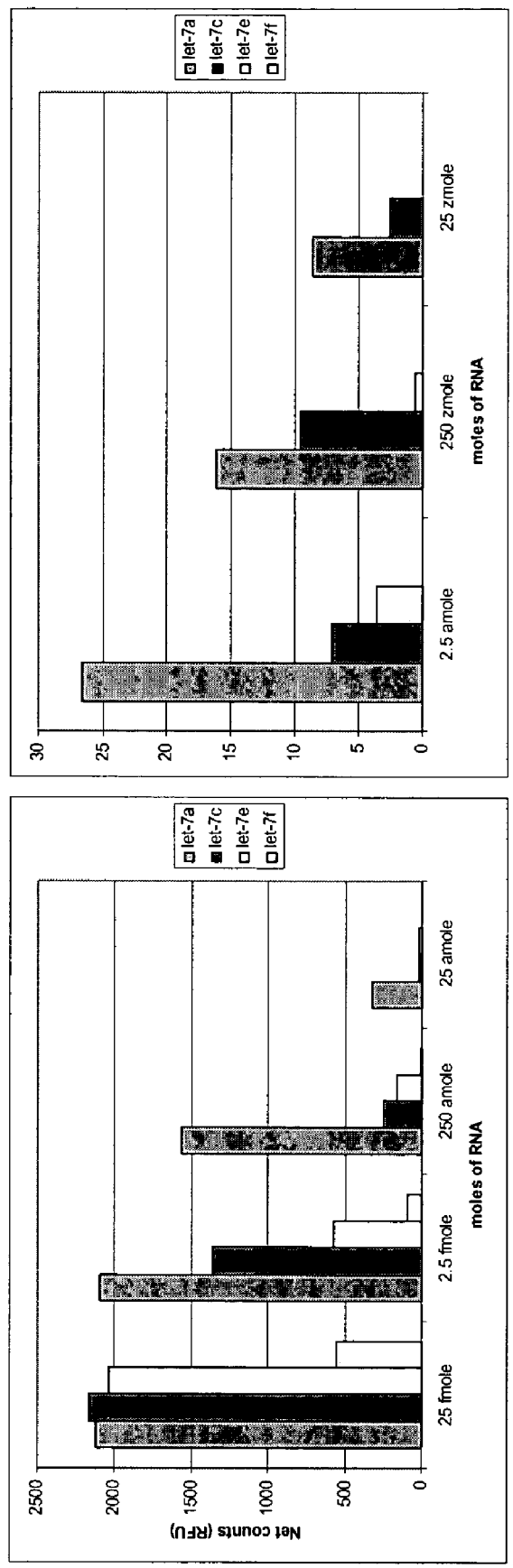
FIG. 9 shows the results of cross reactivity experiments using let-7 miRNA.

The results are shown in FIG. 9. For let-7a design, cross reactivity is maximum when the miRNA is of the same length with a one base change away from the cleavage site. In other words, mismatches at the INVADER oligonucleotide/miRNA hybridizing regions result in high cross reactivity when the mismatch is furthest from the cleavage site (let-7c). Cross reactivity is the lowest when base changes are opposite (or close to) the cleavage site. For let-7a, the worst cross reactivity is with let-7c, which results in 25% of the signal. This Example demonstrates that the INVADER assay is able to differentiate between very similar miRNAs.

Example 5

CLEAVASE IX Enzyme vs CLEAVASE XII Enzyme

This Example describes the optimization of CLEAVASE enzymes for use in miRNA assays. The protocol for temperature optimization described above was utilized. Either 20 ng of the CLEAVASE IX enzyme (Third Wave Technologies, Madison, Wis.) or 30 ng of the CLEAVASE XII enzyme (Third Wave Technologies, Madison, Wis.) was used. The following buffer was used for the CLEAVASE IX enzyme:
2.5 X primary reaction buffer: 25 mM MOPS pH 7.5, 250 mM KCl, 0.125% Tween 20, 0.125% Nonidet NP40, 31.25 mM MgSO$_4$, 10% PEG.
7.5 X secondary reaction buffer: 87.5 mM MgSO$_4$ The following buffer was used for the CLEAVASE XII enzyme:
2.5 X primary reaction buffer: 25 mM MOPS pH 7.5, 62.5 mM KCl, 0.125% Tween 20, 0.125% Nonidet NP40, 62.5 mM MgSO$_4$, 5% PEG.
7.5 X secondary reaction buffer: H$_2$O The LOD experimental protocol was used with either the CLEAVASE 1× or XII enzymes. The LOD was determined for both enzymes. The results are shown in FIG. 11.

Signal increased linearly with increasing amounts of the let-7 miRNA when assayed with either the CLEAVASE IX enzyme or the CLEAVASE XII enzyme. However, R$^2$ values were greater in the CLEAVASE XII enzyme, indicating greater linearity. Moreover, the LOD was lower with the CLEAVASE XII enzyme. The net signal for the detection of 2.5 amoles was 20 counts with the CLEAVASE IX enzyme and 66.75 with the CLEAVASE XII enzyme.

Example 6 miR-135, GAPDH and U6 RNA

A. Design of Oligonucleotides to Detect miR135

Figure 13:
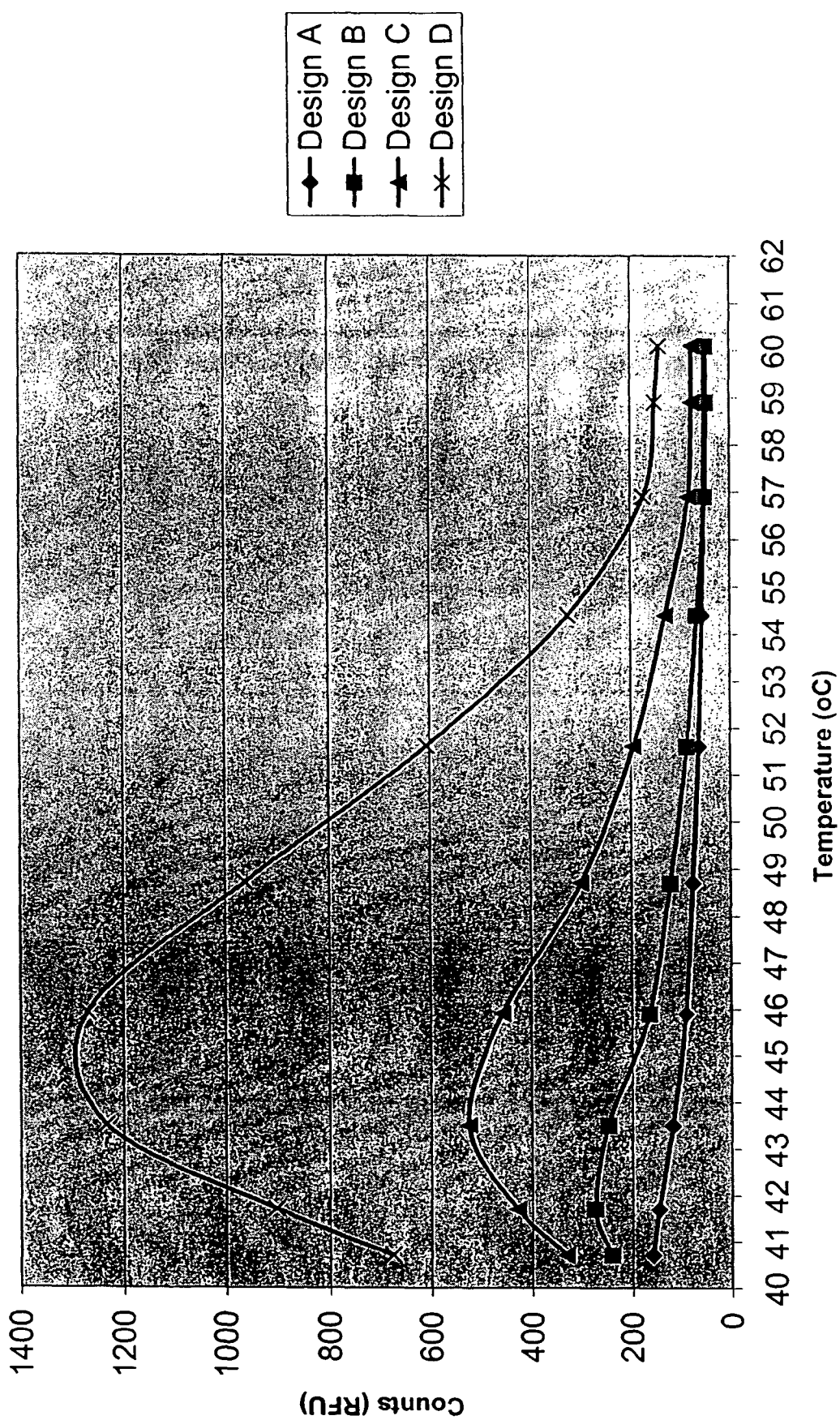
FIG. 13 shows the results of temperature optimization experiments for mir-135.
Figure 14:
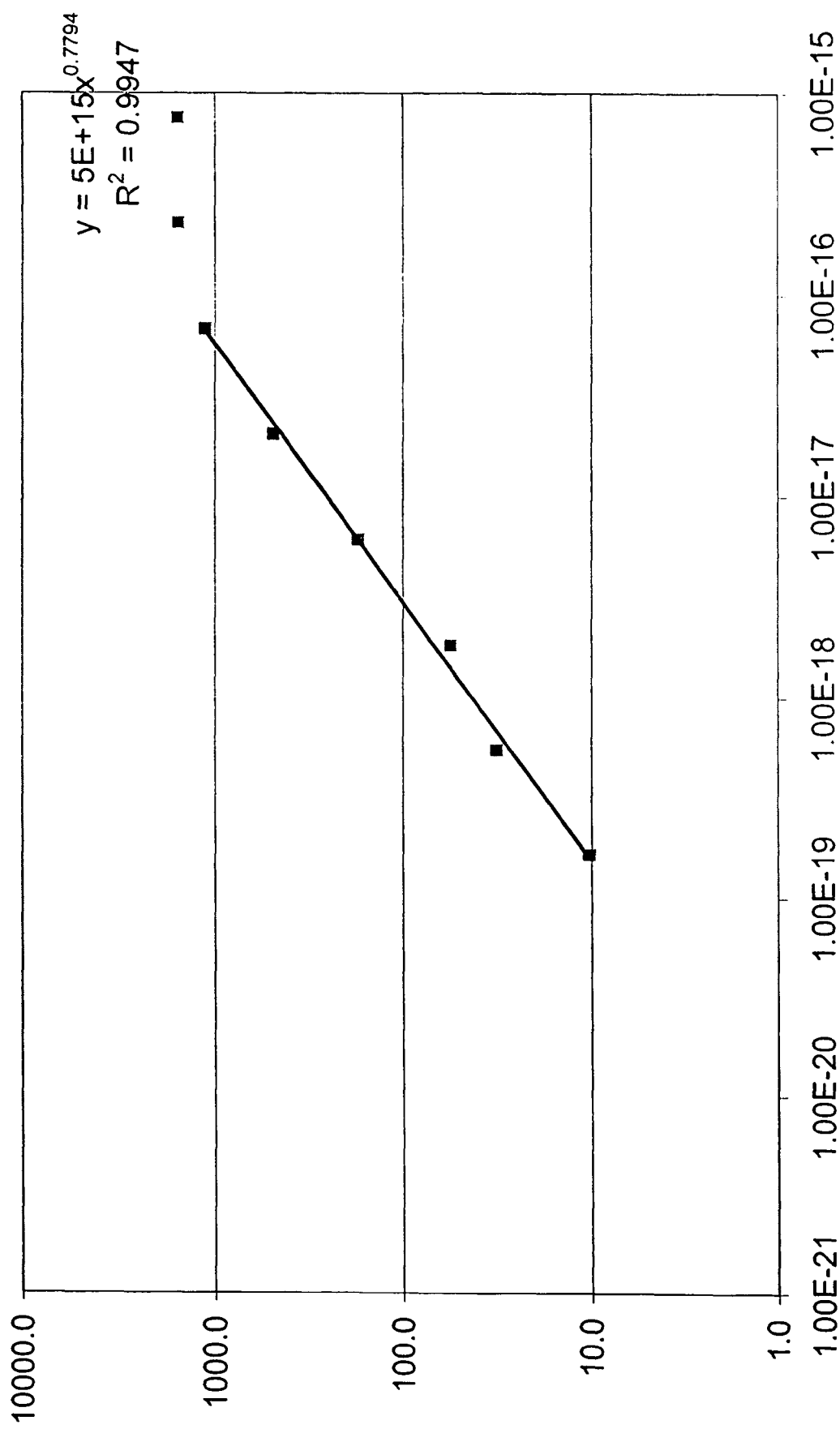
FIG. 14 shows the results of LOD experiments for mir-135.

This example describes assay design and LOD determination for miRNA miR135. Experiments were performed as described in Examples 2 and 3 for miR-1. The oligonucleotide designs are described in FIG. 5. Each of the designs (A-D) utilizes different INVADER and probe oligonucleotides for the detection of mir-135 miRNA. Results of the temperature optimization experiments comparing performance of all of the designs are shown in FIG. 13. Design D gave the highest signal. Results of LOD experiments using assay design D are shown in FIG. 14.

FIG. 14A presents the raw counts generated from four replicate assays at each of the indicated target concentrations. The average counts obtained with each target concentration are indicated as are the net signal and fold-over-zero (FOZ). The limit of detection of the miR-135 target in this experiment was 164 zmoles, equivalent to 98,743 molecules. FIG. 14B contains a graphical representation of the average counts obtained at each concentration and indicates that the INVADER assay is linear throughout much of the concentration range tested.

B. Design of Oligonucleotides to Detect GAPDH and U6 RNA

In some circumstances, it may be desirable to co-detect, e.g. in a biplex assay, an RNA generally present in all cells at constant levels along with one or more miRNA species, which may be expressed in a tissue-specific manner. INVADER assays were therefore designed to two distinct RNAs generally found in all cell types: human glyceraldehydes-3-phosphate dehydrogenase (hGAPDH) and U6 RNA.

In the case of hGAPDH, the following oligonucleotides have been used in biplex miRNA detection assays: INVADER oligonucleotide (SEQ ID NO: 41); probe (SEQ ID NO: 42); ARRESTOR oligonucleotide (SEQ ID NO: 43); SRT oligonucleotide (SEQ ID NO:49), FRET oligonucleotide (red dye) (SEQ ID NO: 48).

In the case of U6, sequence alignments of the U6 RNAs of 8 diverse species from *C. elegans* to mouse to *arabidopsis* to humans to identify a region suitable for the design of a "universal" INVADER assay. The alignment is shown in FIG. 12; the oligonucleotide sequences created to detect this sequence are SEQ ID NOs: 93-95.

Initial experiments carried out with these oligonucleotides on cell lysates using SEQ ID NOs: 45-47 demonstrated that signal from U6 reactions reached saturation well before miRNA signal, possibly owing to large quantities of U6 RNA in cells. Therefore, titration reactions were carried out to determine whether diluting the probe and INVADER oligonucleotide concentrations would render this probe set suitable for use in biplex miRNA detection assays with INVADER and probe final concentrations ranging from 1 µM to 12.5 nM. Final concentrations of the INVADER and probe oligonucleotides between 12.5-50 nM were suitable for biplex miRNA detection for miR-1d and let-7a. ARRESTOR, SRT, and FRET probe concentrations were as described in the previous examples. Further experiments demonstrate that detection of U6 RNA with the "universal" U6 RNA oligonucleotides (SEQ ID NOs: 93-95) is comparable to detection with SEQ ID NOs: 45-47.

Example 7

Detection of let-7, GAPDH, and U6 RNA in Cell Lysates

A. Detection of let 7a in Cell Lysates

This example describes detection of the let-7 miRNA directly in total cell RNA as well as in uninduced fibroblast cells from a human osteosarcoma cell line, MG63 (Third Wave Technologies, Madison, Wis.; catalog number CRL-1427). Total cell RNA was extracted using TRIZOL (Gibco-BRL), as previously described (Chomczynski et al., Anal. Biochem. 162: 156-156 (1987)), and cell lysates were prepared as described by Eis et al., Nature Biotechnology, 19: 673-6 (2001); both publications are herein incorporated by reference.

Reactions were set up as follows. Aliquots of 5 µl of either cell lysate, synthetic miRNA target in lysis buffer (Eis et al., Nature Biotechnology, 19: 673-6 (2001)) at the indicated concentrations, or 5 µl of 20 ng/µl of tRNA (for the no target controls) were pipetted into the appropriate wells of a microtiter plate. A primary reaction master mix was made for 96 reactions containing the following reagents.

| Reagent | Stock concentration | Amount per reaction (µl) | Total added to Master Mix (µl) |
|---|---|---|---|
| Mixture of Probe oligonucleotide 1496-78-01 R (SEQ ID NO: 6) and INVADER oligonucleotide 1496-78-02 (SEQ ID NO: 5) | Probe 20 µM/ INVADER oligonucleotide 200 µM | 0.5 | 45 |
| CLEAVASE XII enzyme | 60 ng/µl | 0.5 | 45 |
| Primary Buffer | 2.5× | 4 | 360 |
| TOTAL | | 5 | 450 |

Aliquots of 5 µl of the primary reaction master mix were added to the wells containing the appropriate target or control. The plate was overlayed with mineral oil (10 µl) and incubated at 53° C. for 2 hrs. After completion of the primary reaction, 5 µl of the following was added to each well, and the plates were incubated at 60° C. for 1.5 hrs. The plate was read using the settings described above (see Example 2).

| Secondary Reaction Components | Stock Conc. | Amount Added |
|---|---|---|
| H2O (or buffer for CLEAVASE IX enzyme assays) | | 2 µl |
| FAM FRET probe (SEQ ID NO: 21) | 10 µM | 1 µl |
| Secondary Reaction Target (SRT) SEQ ID NO: 22 | 1.5 µM | 1 µl |
| ARRESTOR oligonucleotide SEQ ID NO: 7 | 40 µM | 1 µl |
| Total | | 5 µl |

Figure 15:
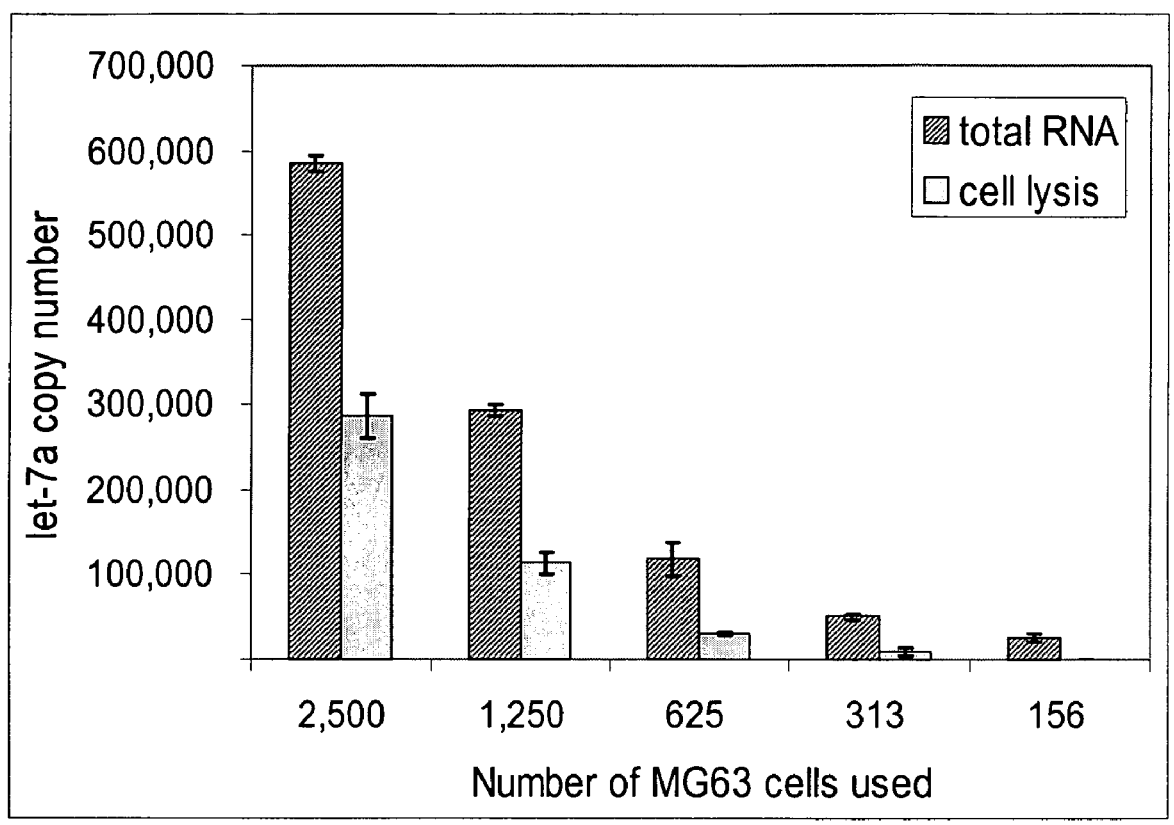
FIG. 15 contains a graphical representation of average counts obtained for the detection of let-7 in cell lysates.

All targets were assayed in quadruplicate. The average counts obtained for the different numbers of cells assayed for both total RNA and cell lysates were plotted in FIG. 15. A standard curve obtained from INVADER assays on known quantities of synthetic let-7a miRNA was used to extrapolate the let-7a copy number per cell. The number of cells from which cell lysates were generated was determined during the seeding procedure prior to cell lysis as described in Eis et al., Nature Biotechnology, 19: 673-6 (2001), herein incorporated by reference. In this experiment, the limit of detection in cell lysates was reached in the total RNA extracts obtained from 156 cells.

B. Lysis in Absence of $Mg^{++}$

An alternative lysis procedure was developed as follows. It had been noted that when the above lysis procedure was used, long mRNAs, i.e. from GAPDH, were not being detected in the quantities expected. Experiments were carried out to examine the effect of $Mg^{++}$ on extraction of RNA in lysates. Extracts lysed in the presence or absence of $MgCl_2$ were compared to total cell RNA extracts prepared using TRIZOL as described above in this example.

Hela cells ($7.5 \times 10^6$ cells) were suspended in 100 µl of a solution of 10 mM MOPS buffer, pH 7.5, with 100 mM KCl. Aliquots of 10 µl were added to separate tubes and lysed with 100 µl of two different lysis buffers prepared as follows:

| MOPS lysis w/Mg$^{++}$ | MOPS lysis w/out Mg$^{++}$ |
|---|---|
| 180 µl 11 µg/ml tRNA | 180 µl 11 µg/ml tRNA |
| 0.5 ml NP40 | 0.5 ml NP40 |
| 4 ml 0.5M MOPS | 4 ml 0.5 MOPS |
| 0.5 ml 1M MgCl$_2$ | N/A |
| 4.82 ml H$_2$O | 5.32 mls H$_2$O |
| 10 mls | 10 mls |

All tubes were then incubated at 80° C. for 15 minutes to lyse the cells, and then centrifuged to pellet debris. Aliquots of 5 µl of the various lysates were added to INVADER reactions as follows.

Primary INVADER reactions were as described above for let-7a; PI oligonucleotide mixes were also made for GAPDH (SEQ ID NOs: 41-43) and for U6 (SEQ ID NOs: 45-47 at 50 nM final concentration).

| Component | Amount added per reaction | Final concentration |
|---|---|---|
| PI oligonucleotide mix* | 0.25 µl | 1 µM each* |
| H$_2$O | 0.25 µl | 0.25 µl |
| CLEAVASE XII enzyme 60 ng/µl | 0.5 µl | 0.5 µl |
|  | 4 µl | 4 µl |
| Total | 5 µl | 5 µl |

*Primary INVADER reactions were as described above for let-7a; PI oligonucleotide mixes were also made for GAPDH (SEQ ID NOs: 41-43) and for U6 (SEQ ID NOs: 45-47 at 50 nM final concentration).

Primary reaction mixtures were incubated at 49° C. for 1 hour. Aliquots of the following secondary reaction mixture were then added:

| Component | Amount added per reaction |
|---|---|
| Secondary reaction mixture* | 1.5 µl |
| H$_2$O | 3.5 µl |
| Total | 5 µl |

Secondary reaction mixture included SRTs (SEQ ID NO: 22 for let-7; SEQ ID NO: 49 for GAPDH and U6) target, FRET oligonucleotides (SEQ ID NO: 21 for let-7; SEQ ID NO: 48 for GAPDH and U6), arrestors (SEQ ID NO:7 for let-7, SEQ ID NO:43 for GAPDH, and SEQ ID NO: 47 for U6) at the concentrations indicated in Example 7A.

Secondary reactions were run at 60° C. for 1 hour. Reactions were read on a CYTOFLUOR microplate reader as described in Example 2. The results are presented in FIG. 16 and indicate that presence of the GAPDH signal is dependent on the absence of Mg++ from the lysis buffer, whereas U6 RNA signal remains relatively constant regardless of the presence of Mg++. Additional experiments confirmed that all RNAs were detectable in total cell RNA at levels comparable to those obtained from lysis in the absence of Mg++.

Example 8

Alternative INVADER Assay Designs for Detection of Various miRNAs

A. Alternative Designs for Detection of let-7A

This example describes the creation and testing of alternative oligonucleotide designs for detection of the let-7a miRNA. In one series of experiments, a set of alternative designs was created in which the target specific regions of both the INVADER oligonucleotide and the probe oligonucleotide were eleven nucleotides long. A second set of designs was created in which the target specific regions of the probe oligonucleotides were 10 nucleotides long and the target specific regions of the INVADER oligonucleotides were 12 nucleotides long.

1. Oligonucleotide Designs a. 11-mer Probe and INVADER Oligonucleotide Designs

FIG. 5 shows sets of alternative oligonucleotide designs for detection of the let-7a miRNA in which the target specific regions of both the probe and INVADER oligonucleotides are 11 nucleotides long. SEQ ID NOs: 50-51 provide a design in which both the INVADER and probe oligonucleotides are linear. SEQ ID NO: 6 contains a probe oligonucleotide that forms a stem-loop structure); SEQ ID NO: 5, an INVADER oligonucleotide that forms a stem-loop structure); SEQ ID NOs: 5-6, both probe and INVADER oligonucleotides with stem-loops.

b. 10-mer Probe and 12-mer INVADER Oligonucleotide Designs

FIG. 5 shows a set of alternative oligonucleotide designs for detection of the let-7a miRNA in which the target specific regions of the probe comprise 10 nucleotides, and those of the INVADER oligonucleotides, 12 nucleotides. SEQ ID NOs: 52-53 provide a design in which both the INVADER and probe oligonucleotides are linear. SEQ ID NO: 2 contains a probe oligonucleotide that forms a stem-loop structure); SEQ ID NO: 1, an INVADER oligonucleotide that forms a stem-loop structure).

2. Temperature Optimization Profiles of Alternative Oligonucleotide Designs for Detection of the let-7a miRNA Temperature optimization experiments were carried out as follows. A master mix was made for 24 reactions. Each reaction contained the following:

| Stock concentration | Volume per reaction | Final concentration |
|---|---|---|
| 2.5× Primary reaction buffer for the CLEAVASE XII enzyme (as described in Example 5) | 4 µl | 1× |
| 10 µM probe* | 1 µl | 1 µM |
| 100 µM INVADER oligonucleotide* | 1 µl | 10 µM |
| 60 ng/µl CLEAVASE 12 | 0.5 µl | 30 ng |
| H$_2$O | 2.5 µl | N/A |
| 30 pM miRNA (for the 11-mer temperature optimizations) OR 10 nM miRNA (for the10-mer probe/12-mer INVADER oligonucleotide temperature optimizations) | 1 µl | 3 pM OR 1 nM |
| 20 ng/µl tRNA (for no target controls only) | 1 µl | 2 ng |
| TOTAL | 10 µl | |

*Various combinations of probe and INVADER oligonucleotides were used in this experiment as indicated in FIGS. 16-17.

Secondary reaction mixes were as described in Example 3 for let-7. Where appropriate, ARRESTOR sequences were made to compliment the entire loop and target specific regions of the probe and extending 6 bases toward the 5' end of the probe.

In the case of the 11-mer temperature optimization experiment, the primary reactions were run at 50±9° C. for 1 hour followed by a 15 minute secondary reaction at 60° C. as described in Example 2. As for the 10-mer probe, with the 12-mer INVADER oligo, the primary reactions were run at 50±9° C. for 15 minutes followed by a 15 minute secondary reaction at 60° C.

Results for the designs in which the target specific portions of the INVADER and probe oligonucleotides were 11 nucleotides long are presented in FIG. 18. FIG. 18A shows the temperature optimization profiles of each design. FIG. 18B shows the normalized maximum performance of each design, including the optimum temperature for each. Results for the designs in which the target specific portion of the probe oligonucleotide was 10 bases and that of the IVADER oligonucleotide was 12 are presented in FIG. 19. FIG. 19A shows the temperature optimization profiles, and FIG. 19B, the normalized maximum performance of each design.

Examination of these results suggests that which design results in maximum performance varies depending on both reaction conditions and the relative stability of the miRNA-oligonucleotide hybrid formed. For example, when the target specific regions of both oligonucleotides are 11 bases long, the probe target specific region has a predicted Tm of 49° C. and that of the INVADER, of 37° C. In this case, stabilization of the INVADER oligonucleotide-miRNA interaction confers improved assay performance on this design. However, for the let-7a designs in which probes were 10-mers and INVADER oligonucleotides, 12-mers, the target specific regions of the two oligonucleotides have approximately equivalent Tms. In this case, the design in which both oligonucleotides are looped works best.

3. LOD of let-7a Using Two Alternative Designs

Experiments were set up as described in Example 3 to compare the LOD of the double loop design and the single loop design, in which the INVADER oligonucleotide forms a stem-loop structure.

Figure 20:
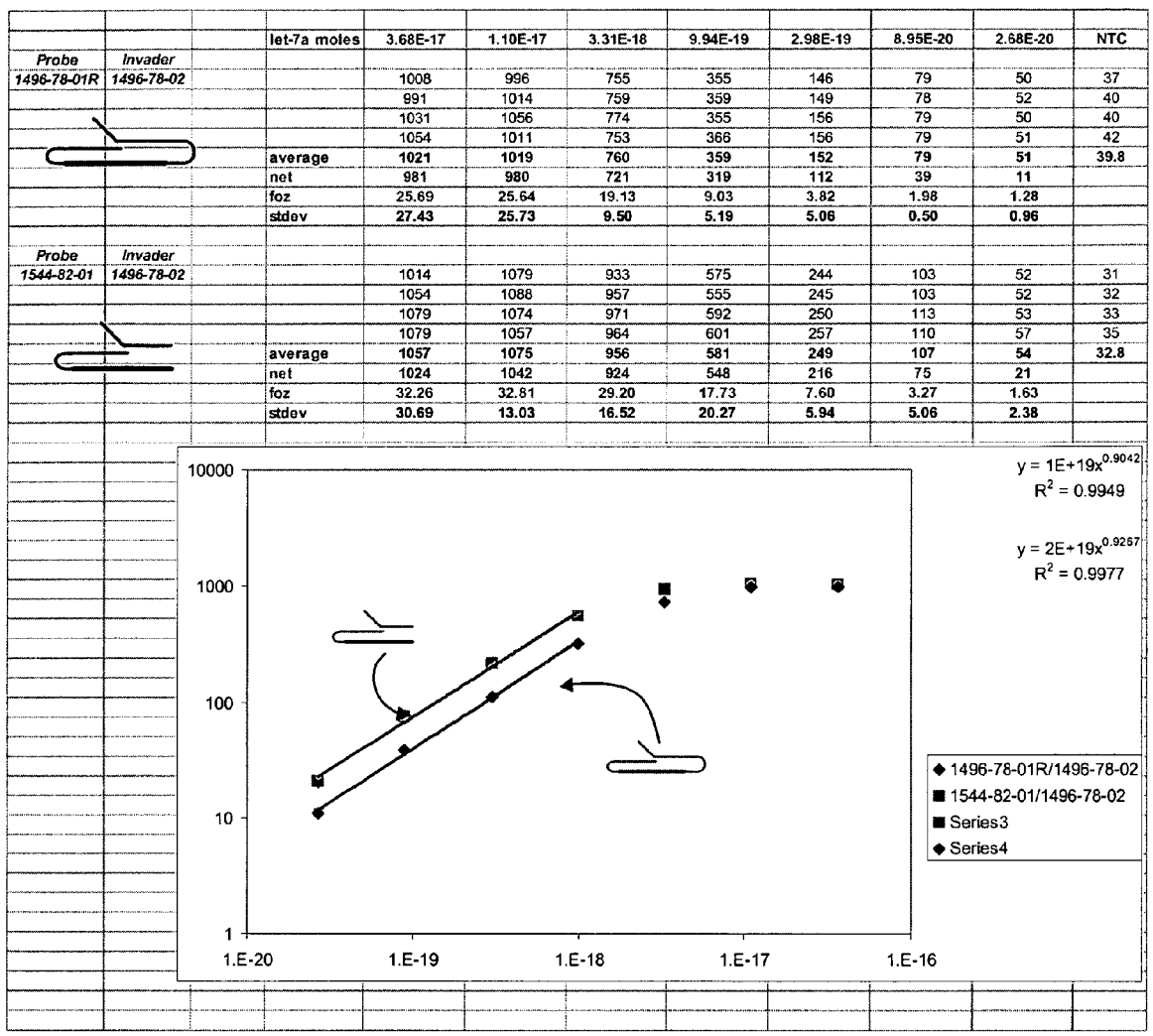
FIG. 20 shows the results of experiments to compare the LODs of two alternative oligonucleotide designs.

Reactions to determine LOD were run in quadruplicate. Reaction mixtures contained the following reagents (final concentrations):

| Stock concentration | Volume per reaction | Final concentration |
|---|---|---|
| 2.5× Primary reaction buffer for CLEAVASE XII enzyme | 4 µl | 1× |
| 10 µM probe/200 µM INVADER oligonucleotide mix (sequences as indicated in FIG. 20) | 0.5 µl | 1 µM probe/20 µM INVADER oligonucleotide |
| 60 ng/µl CLEAVASE XII enzyme | 0.5 µl | 30 ng |
| Total | 5 µl | |

Aliquots of 5 µl of miRNA were added to the wells containing the reaction mixtures at the final concentrations indicated in FIG. 20. Primary reactions were run for 1.5 hours at the optimal temperatures for each designed as determined in Example 8B (50° C. for the looped INVADER oligonucleotide design and 53° C. for the double loop design). The secondary reactions were set up as described in Examples 2 and 3 and run for 1 hour at 60° C.

The results in FIG. 20 show net signal produced as a function of moles of miRNA. The linear ranges of the plots indicated that more signal was produced from a given amount of miRNA using the INVADER loop design than from the double loop design. Similarly, an examination of the table in FIG. 20 indicates that the fold-over-zero values at each miRNA level are greater for the single loop design. Both designs resulted in sufficient FOZ at the lowest concentrations tested, $2.68 \times 10^{-20}$ moles, or 26.8 zeptomoles, equivalent to approximately 16,000 molecules.

4. Full Length vs. Shortened ARRESTOR Oligonucleotides

Experiments were conducted to evaluate the relative performance of full-length ARRESTOR molecules, e.g. as shown in FIGS. 4 and 12, in which the ARRESTOR molecules extend at their 5' ends around the loop, throughout the length of the miRNA-specific region of the probe and into the 5' flap region vs. shortened ARRESTOR molecules that are complementary only to the miRNA-specific region of the probe and part of the 5' flap but do not extend into the loop region or beyond. Reactions were set up as follows to detect synthetic let-7a miRNA:

| Component | Stock concentration | Amount added per reaction |
|---|---|---|
| PI mix (probe SEQ ID NO: 6; INVADER oligonucleotide SEQ ID NO: 5) | 10 µM probe 50 µM INVADER oligo | 1 µl |
| CLEAVASE XII enzyme | (60 ng/µl) | 0.5 µl |
| H₂O | | 0.5 µl |
| Primary Reaction Buffer | 2.5× | 4 µl |
| Total | | 6 µl |

Aliquots of 6 µl of the primary reaction mix were added to the appropriate wells of a microtiter plate followed by aliquots of 4 µl of syntheticlet-7a miRNA or 4 µl of 10 ng/µl tRNA in dH₂O at the final concentrations indicated in the table below. Primary INVADER reactions were incubated at 53° C. for 1.5 hours.

Aliquots of secondary reaction mixtures were added as follows:

| Full-length ARRESTOR | | |
|---|---|---|
| Component | Stock concentration | Amount added |
| ARRESTOR SEQ ID NO: 7 for full length ARRESTOR, SEQ ID NO: 54 for shortened ARRESTOR | 40 µM | 1 µl |
| MO5 SRT (SEQ ID NO: 22) | 1.5 µM | 1 µl |
| FRET FAM (SEQ ID NO: 21) | 10 µM | 1 µl |
| H₂O | | 2 µl |

Secondary reactions were incubated at 60° C. for 1.5 hours. Microtiter plates were read as described in Example 2. The results were as shown in FIG. 17.

These results indicate that there is no significant different in signal generation or limit of detection when full-length or shortened ARRESTOR oligonucleotides complementary to the miRNA-specific portion of the probe are used in the secondary INVADER reaction.

B. Alternative Designs Using Linear Probe and INVADER Oligonucleotides

Alternative designs were tested in which both the probe and INVADER oligonucleotides contain a universal sequence, and neither oligonucleotide forms a hairpin. A schematic of the design is presented in FIG. 4. The universal sequence is present on the 5' end of the INVADER oligonucleotide and on the 3' end of the probe oligo. A short, complementary "capture" oligonucleotide is added and is comprised of 2'-O-methyl residues, allowing it to promote co-axial stacking in the presence of the miRNA (e.g. SEQ ID NO: 60). Designs were created for both miR-15 (SEQ ID NOs: 58-59 and 61) and mir-135 (SEQ ID NOs: 63-65). Initial designs, while leading to high non-specific background signal in the absence of miRNA target, nonetheless indicate that it is feasible to detect miRNAs with such universal capture oligonucleotides.

Example 9

Effect of 2'-O-Methylation of Nucleotide Residues in the Loops

This example describes experiments aimed at assessing the effect of substituting 2'-deoxy residues for some or all of the 2'-O-methyl residues incorporated in the probe and INVADER oligonucleotides used for detecting miRNAs. All of the designs presented in the preceding examples include 2'-O-methyl residues in the loop regions as described in Example 2. Experiments were conducted to test the effect of substituting 2' deoxy residues for some or all of the 2'-O-methyl residues in the INVADER and probe oligonucleotides designed to detect the let-7a miRNA.

FIG. 5 shows the modified let-7a designs. SEQ ID NOs: 5-6 contain 2'-O-methyl residues as described in Example 2. The design in SEQ ID NOs: 73-74 contain 2'deoxy residues at all positions; and those in SEQ ID NOs: 75-76, 2'-O-methyl residues in the portions of the stems adjacent to the target.

INVADER reactions were set up to compare the signal generation and temperature optima of the three different designs. Reactions were as described in the LOD experiments in Example 8 and included 100 pM synthetic miRNA, 1 µM probe, and 10 µM INVADER oligonucleotide. Primary reactions were run for 15 minutes at the temperatures indicated; secondary reactions were run for 5 minutes at 60° C.

Figure 21:
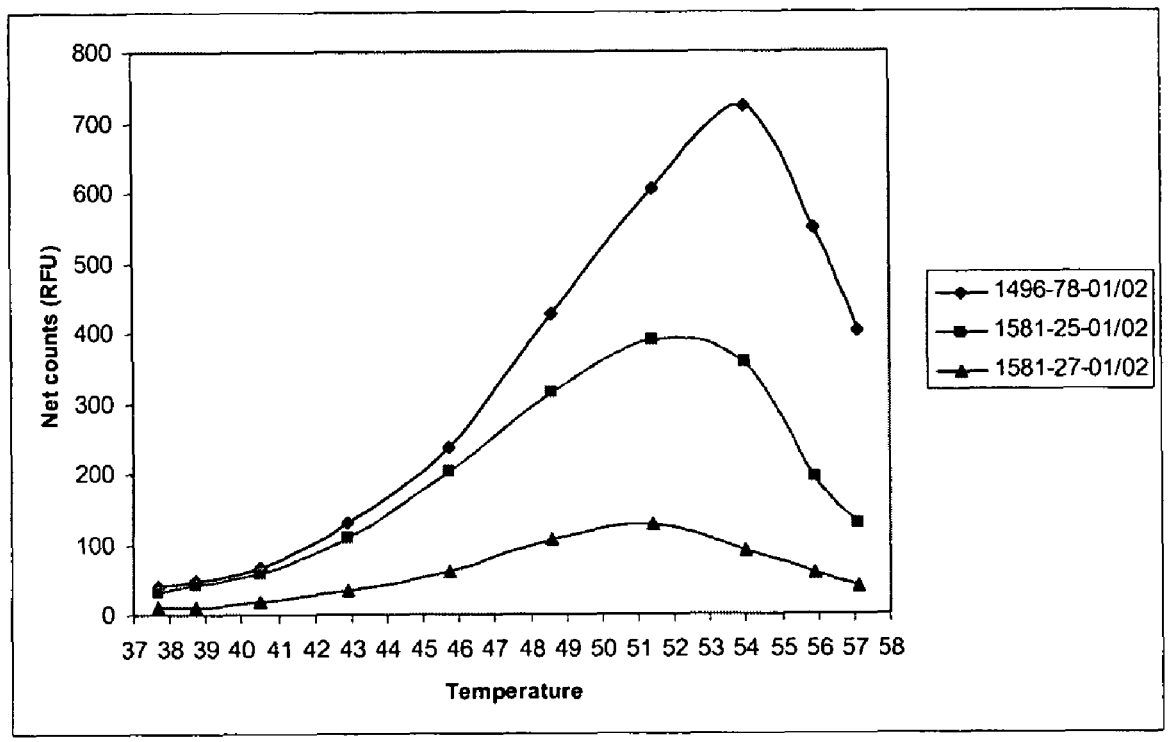
FIG. 21 shows results comparing the effects of substituting 2'-deoxy residues for some or all of the 2'-O-methyl residues in the probe and INVADER oligonucleotides.

The results of the INVADER assays are shown in FIG. 21 and indicate that the design in which the stem loop structures are comprised of 2'-O-methyl residues yields the most signal, followed by the design in which the bases adjacent to the target are comprised of 2'-O-methyl residues. The oligonucleotides comprised entirely of 2'-deoxy residues generated the lowest levels of signal.

A further set of experiments was designed to test additional design variations as follows: probe and INVADER oligonucleotides with shorter hairpins, probe and INVADER oligonucleotides with more stable loops or, alternatively with shorter loops, probe and INVADER oligonucleotides with only three 2'-O-methyl residues. Primary reactions were set up to test detection of miR-15 as follows.

The following probe/INVADER oligonucleotide combinations were tested.

| Probe | | INVADER oligo | |
|---|---|---|---|
| 1544-71-01 | SEQ ID NO: 55 | 1544-71-02 | SEQ ID NO: 56 |
| 1544-71-01 | SEQ ID NO: 55 | 1796-43-02 | SEQ ID NO: 68 |
| 1544-71-01 | SEQ ID NO: 55 | 1796-43-04 | SEQ ID NO: 70 |
| 1544-71-01 | SEQ ID NO: 55 | 1796-43-06 | SEQ ID NO: 72 |
| 1796-43-01 | SEQ ID NO: 67 | 1544-71-02 | SEQ ID NO: 56 |
| 1796-43-03 | SEQ ID NO: 69 | 1544-71-02 | SEQ ID NO: 56 |
| 1796-43-05 | SEQ ID NO: 71 | 1544-71-02 | SEQ ID NO: 56 |
| 1796-43-03 | SEQ ID NO: 69 | 1796-43-04 | SEQ ID NO: 70 |

Primary reaction mixes were made as follows.

| Primary Reaction Component | Stock Concentration | Amount Added |
|---|---|---|
| Probe oligonucleotide (as indicated in above table) | 40 µM | 0.25 µl |
| INVADER oligo | 40 µM | 0.25 µl |
| CLEAVASE XII enzyme | 60 ng/µl | 0.5 µl |
| Primary Reaction Buffer | 2.5× | 4 µl |
| Total | | 5 µl |

Aliquots of 5 µl of Primary reaction mix were added to 5 µl of synthetic miR-15 RNA at the following final amounts: 0, 0.1 amole, 0.33 amole, 1.09 amole. Primary reactions were incubated at 52.5° C. for 2 hours.

Secondary reaction mixes were made as follows.

| Secondary reaction component | Concentration | Amount Added |
|---|---|---|
| FAM FRET oligonucleotide (SEQ ID NO: 21) and Secondary Reaction Target (SRT) (SEQ ID NO: 40) | 13.4 µl FAM FRET 2 µM SRT | 0.75 µl |
| ARRESTOR oligonucleotide (SEQ ID NO: 66) | 54 µM | 0.75 µl |
| H₂O | | 3.5 µl |
| Total | | 5 µl |

Aliquots of 5 µl were added and the reactions incubated at 60° C. for 45 minutes. The results, in relative fluorescent units (RFUs) are presented below.

| Probe Invader | | | | NET | FOZ |
|---|---|---|---|---|---|
| 1544-71-01 1544-71-02 | | | | | |
| 1.09 amole | 655 | 658 | 662 | 566 | 7.13 |
| 0.33 amole | 314 | 262 | 256 | 185 | 3.00 |
| 0.10 amole | 122 | 138 | 134 | 39 | 1.42 |
| 0 amole | 88 | 93 | 96 | | |
| 1796-43-01 1544-71-02 | | | | | |
| 1.09 amole | 1689 | 1744 | 1895 | 146 | 1.09 |
| 0.33 amole | 1655 | 1717 | 1817 | 99 | 1.06 |

-continued

| Probe Invader | | | | NET | FOZ |
|---|---|---|---|---|---|
| 0.10 amole | 1692 | 1693 | 1695 | 63 | 1.04 |
| 0 amole | 1636 | 1601 | 1654 | | |
| 1544-71-01 1796-43-04 | | | | | |
| 1.09 amole | 676 | 688 | 693 | 579 | 6.43 |
| 0.33 amole | 274 | 275 | 264 | 164 | 2.54 |
| 0.10 amole | 153 | 137 | 143 | 38 | 1.35 |
| 0 amole | 111 | 107 | 102 | | |
| 1796-43-05 1544-71-02 | | | | | |
| 1.09 amole | 806 | 824 | 773 | 708 | 8.64 |
| 0.33 amole | 280 | 280 | 262 | 181 | 2.96 |
| 0.10 amole | 144 | 145 | 139 | 50 | 1.54 |
| 0 amole | 91 | 95 | 92 | | |
| 1544-71-01 1796-43-02 | | | | | |
| 1.09 amole | 706 | 738 | 777 | 636 | 7.12 |
| 0.33 amole | 281 | 287 | 290 | 182 | 2.75 |
| 0.10 amole | 149 | 150 | 153 | 47 | 1.45 |
| 0 amole | 104 | 101 | 107 | | |
| 1796-43-03 1544-71-02 | | | | | |
| 1.09 amole | 882 | 869 | 847 | 702 | 5.27 |
| 0.33 amole | 335 | 341 | 341 | 175 | 2.06 |
| 0.10 amole | 196 | 209 | 196 | 36 | 1.22 |
| 0 amole | 169 | 165 | 159 | | |
| 1544-71-01 1796-43-06 | | | | | |
| 1.09 amole | 625 | 562 | 579 | 501 | 6.69 |
| 0.33 amole | 229 | 215 | 204 | 128 | 2.45 |
| 0.10 amole | 126 | 121 | 112 | 32 | 1.36 |
| 0 amole | 94 | 87 | 83 | | |
| 1796-43-05 1796-43-06 | | | | | |
| 1.09 amole | 772 | 752 | 704 | 631 | 6.65 |
| 0.33 amole | 260 | 252 | 251 | 143 | 2.28 |
| 0.10 amole | 140 | 142 | 139 | 29 | 1.26 |
| 0 amole | 115 | 109 | 111 | | |

These results suggest that the designs in which the probe oligonucleotide contained a shortened hairpin and a highly stable tetra-loop comprised of 2'-O-methyl residues in combination with the original INVADER oligonucleotide design (2'-O-methyl residues, TTTT loop, long hairpin) may generate a somewhat higher FOZ value. Otherwise, none of the alternative design oligonucleotide sets offered any improvement over the original designs. It is noteworthy that the combination of an all-DNA INVADER oligonucleotide with the original chimeric probe oligonucleotide gave FOZ values approximately equivalent to those obtained with both chimeric probe and INVADER oligonucleotides. In some applications, substitution of an all DNA INVADER oligonucleotide may be desirable to reduce oligonucleotide synthesis costs and may be made without sacrificing limit of detection.

Further experiments demonstrated that it is possible to compensate for sub-optimal signal generation with particular oligonucleotide sets by adding more RNA (e.g. lysate, purified total RNA, synthetic miRNA) to the reaction. Similarly, additional experiments in which various oligonucleotides (i.e. probe, INVADER, ARRESTOR, or various combinations thereof) were gel purified as described in Example 1 indicated that standard gel purification of all three types of oligonucleotides gives maximal signal. It is possible to achieve signal levels approximately equal to the maximal levels with gel purified probes if the other oligonucleotides, i.e. the INVADER and ARRESTOR oligonucleotides, are desalted following synthesis.

Example 10

Detection of miRNA Expression in Total RNA From Multiple Tissue Types

This example describes experiments carried out to test the suitability of the INVADER assay to detect different miRNA species in total RNA extracted from diverse tissue types. In order to evaluate tissue specific gene expression, temperature optima and LODs were first determined for each design.

1. INVADER and Probe Oligonucleotide Designs

INVADER assay oligonucleotides were designed to detect the miR-15, miR-16, and miR-125b miRNA species. The designs for these assays are presented in FIG. 5. The designs for let-7a and miR-135 are described in Examples 2 and 6, respectively.

2. Determination of Temperature Optima and LODs

Temperature optimization experiments were conducted for each of these oligonucleotide sets as described in Example 8. Each primary reaction included 1 nM of the targeted miRNA and was carried out for 15 minutes at temperatures ranging from 50±9° C. Secondary reactions were as described in Example 2 and were run for 1 to 1.5 hours at 60° C. Optimum temperatures were as follows:

| let-7a | 53° C. |
| miR-15 | 53° C. |
| miR-16 | 56° C. |
| MiR-125b | 52° C. |
| MiR-135 | 45° C. |

Once the temperature optima were obtained, LODs were determined for each miRNA species as described in Example 8. All LODs were 30 zeptomoles.

3. Gene Expression Profiling

Figure 23:
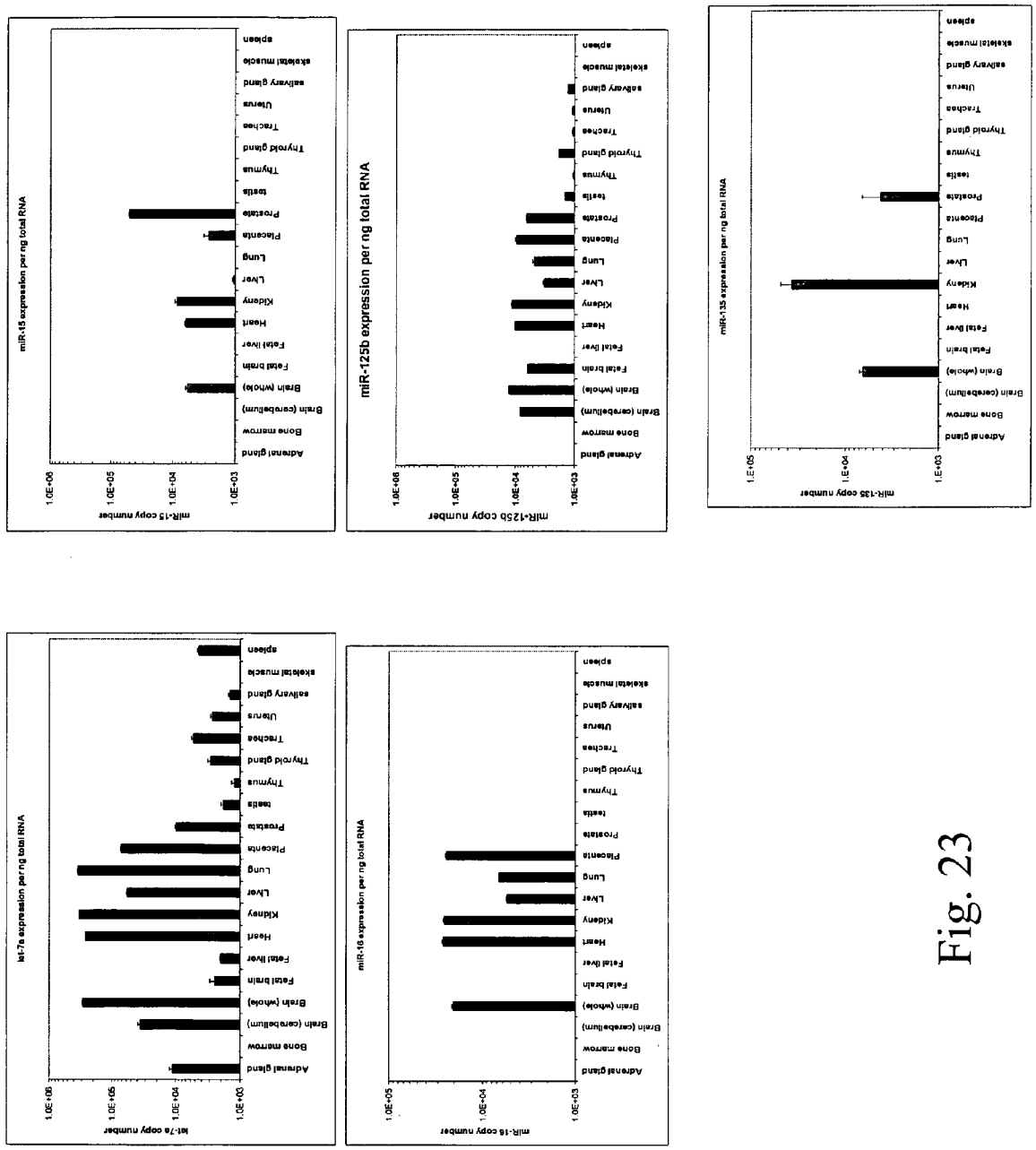
FIG. 23 shows the results of experiments to detect five different miRNA species in total RNA isolated from 20 different tissue types.

Gene expression profiling was carried out on total RNA extracted from 20 different tissue types. Total RNA was purchased from Clontech (Palo Alto, Calif., catalog number K4008-1, Human Total RNA Master Panel 11). For let-7a, 50 ng of total RNA was tested in each reaction; for the other miRNA species, 100 ng of total RNA was tested. All reactions were set up as described in Example 8; primary reactions were run at the temperature optima for 1.5 hours; secondary reactions were as described above. The gene expression profiles for each miRNA species are presented in FIG. 23. These results indicate that the INVADER assay can be used to examine miRNA expression in different tissue types. These data further suggest that let-7a and miR-125b are expressed in a wide variety of tissues; the other miRNA species appear to be more specific to a limited number of tissue types.

Example 11

Effects of Variable Oligonucleotide Length on INVADER Assay Detection of miRNA

This example describes the impact of alterations in probe and INVADER oligonucleotide length on detection of the let-7a 22-nt miRNA. In particular, these experiments compare detection of an miRNA that forms perfect stacking interactions between the ends of the probe and INVADER oligonucleotides to detection of an miRNA that forms both 5' and 3' overlaps as well as to one that results in a single nucleotide gap at both the 5' and 3' ends.

FIG. 24 shows the results of analyzing three different types of designs. SEQ ID NOs: 5-6 shows a perfect stack between the 22-nt target and the flanking ends of the looped probe and INVADER oligonucleotides. In SEQ ID NOs: 83-84, both the probe and INVADER oligonucleotides are extended by a single base, resulting in both 5' and 3' overlaps. In SEQ ID NOs: 85-86, both the probe and INVADER oligonucleotides are shortened by a single base, relative to the designs in SEQ ID NOs: 5-6, resulting in a single nucleotide gap at both ends.

INVADER assays were set up to test the performance of these oligonucleotide sets for detection of synthetic let-7a miRNAs. Reactions were carried out as described in Example 8 and included 100 pM synthetic let-7a miRNA, 1 µM probe and 10 µM INVADER oligonucleotide. Primary reactions were run for 15 minutes at 53° C.; secondary reactions, for 5 minutes at 60° C., as described in Example 2. The results are presented in FIG. 24.

These data indicate that in this experiment, a single nucleotide overlap at both ends of the miRNA target resulted in an approximately 30% decrease in signal generation as well as a reduction of 2° C. in optimal temperature. A one nucleotide gap at both ends of the target, however, did not reduce signal generation, though it did reduce the optimal reaction temperature by 5° C.

Example 12

Discrimination of miRNA From Precursor RNA and From Encoding DNA

Experiments were carried out to determine whether the INVADER miRNA assay discriminated the miRNA target itself from both its precursor RNA and from the DNA encoding the miRNA.

A. Precursor Cross-Reactivity Test

Precursor let-7 RNA (SEQ ID NO: 87) was transcribed in vitro and analyzed by capillary electrophoresis to determine whether it contained any fragments that might mimic the let-7a miRNA. The shortest contaminating fragment was estimated to be approximately 45 nt. LOD reactions were run essentially as described in Example 3 at precursor or synthetic 5' P let-7a mi-RNA concentrations as indicated in the table below. PI mixes contained 10 µM probe SEQ ID NO: 6 and 100 µM INVADER oligonucleotide SEQ ID NO: 5. Primary reactions were run at 53° C. for 1 hour; secondary reactions were run at 58° C. for 1 hour with secondary reaction mixes essentially as described in Example 3 (FRET probe SEQ ID NO: 21, SRT SEQ ID NO: 22, and ARRESTOR SEQ ID NO: 7). The results of this experiment indicated that this miRNA assay is approximately 4% cross reactive vs. the precursor RNA.

B. Discrimination of RNA vs. DNA Signal

Reactions were run to detect let-7a miRNA in cell lysates as described in Example 7. Prior to detection with the INVADER assay, aliquots 1 µl of 8 µg/µl RNAse A (Qiagen, Inc.) were added to 80 µl of cell lysate and incubated at 37° C. for 2.25 hours. The RNAse A treated samples failed to generate any signal above background, indicating that signal generated in assays lacking RNAse A arises from detection of the miRNA target and not the encoding DNA (FIG. 16). Further experiments were carried out in which RNAse A was added either prior to the primary reaction or prior to the secondary reaction. When RNAse A was added prior to the primary reaction, no signal was generated, consistent with the previous results. When RNAse A was added subsequent to the primary reaction, no loss of signal was observed, further indicating that the signal being detected is due to RNA and that there is no adverse effect of RNAse on other reaction components, e.g. the CLEAVASE enzyme.

Example 13

Detection of a Dual Form miRNA

Oligonucleotide designs were created for miR-124a. These oligonucleotides can be used to detect two naturally occurring miRNAs—one 21 nt in length and the other, 22 nt.

Figure 22:
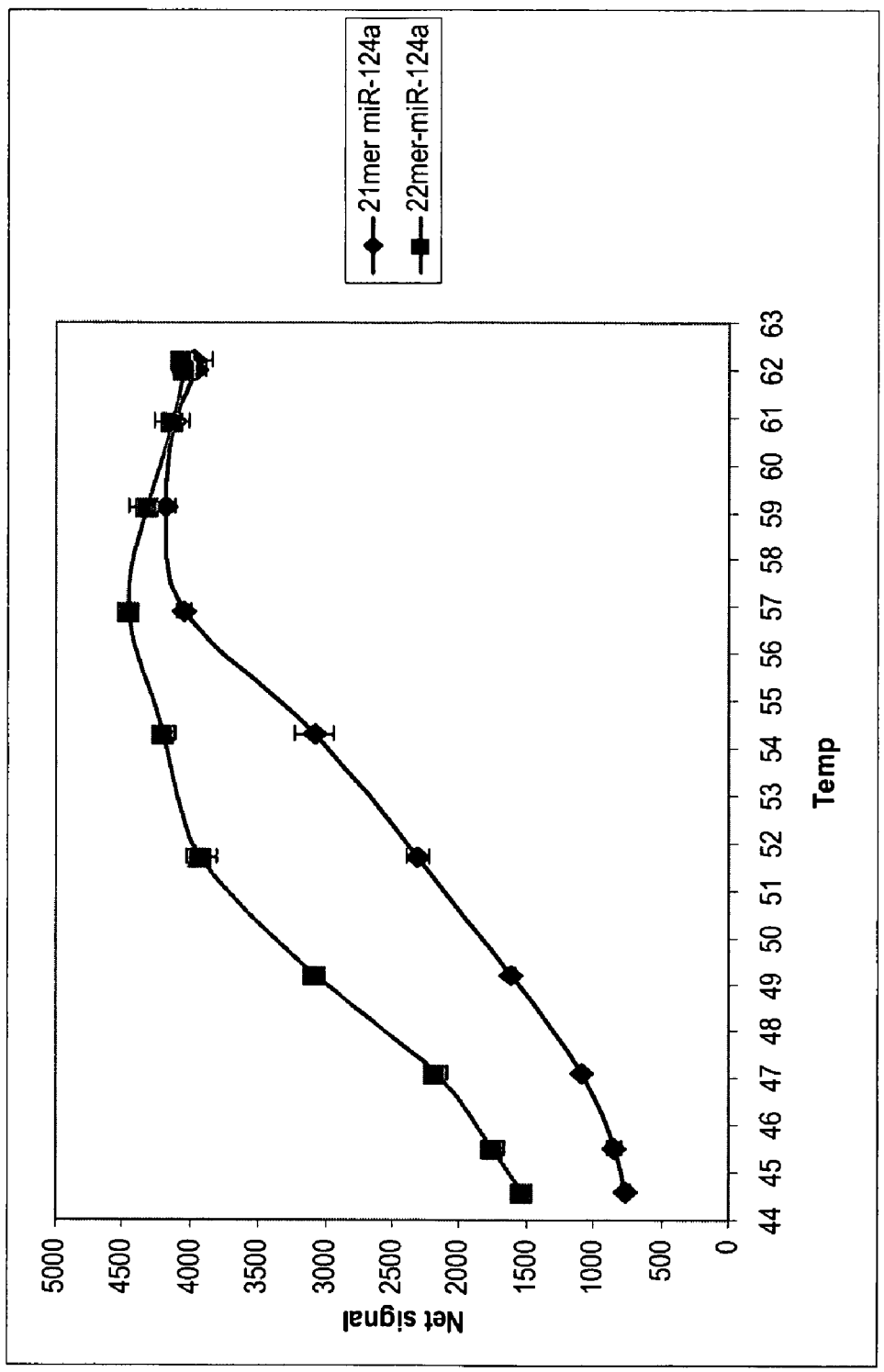

Temperature optimization reactions were set up, essentially as described in Example 3, using 1 nM of synthetic miRNA target, 25 primary reaction and a 15 minute secondary reaction. The oligonucleotides used in these reactions are listed in FIG. 5 (SEQ ID NOs: 90-92). Temperature profiles for the two different length miRNA targets are shown in FIG. 22 and indicate that the same oligonucleotide designs can be used to detect both targets.

Example 14

Oligonucleotide Designs for Detection of an siRNA

Figure 25:
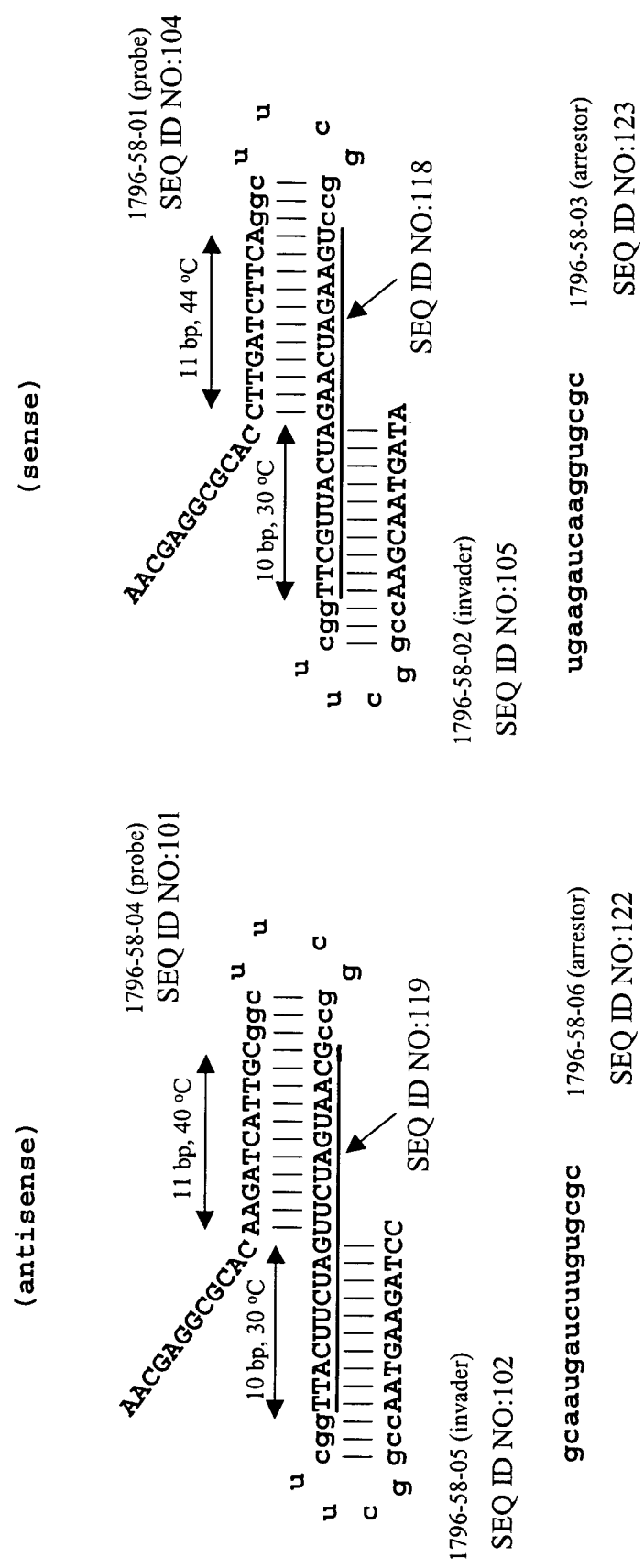
FIG. 25 (SEQ ID NOS:118-119, SEQ ID NOS:101-102, SEQ ID NOS:104-105, and SEQ ID NOS:122-123) shows exemplary invasive cleavage oligonucleotide designs for detection of an siRNA. Lower case residues indicate 2'-O-methyl.

Approaches similar to those described in the preceding examples may similarly be used to detect siRNAs. FIG. 25 illustrates two alternative INVADER assay designs for detection of a β-actin siRNA. This siRNA is described in Harborth, J. et al., Journal of Cell Science, 114: 4557-4565 (2001). One design is presented for each the sense and antisense strands; exemplary oligonucleotides for detecting this siRNA are listed in FIG. 26, SEQ ID Nos: 101-106.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, genetics, or related fields are intended to be within the scope of the following claims.

We claim:

1. A method for analyzing microRNA, comprising:
   a) contacting microRNA comprising a 3' portion comprising a 3' terminal end and a 5' portion comprising a 5' terminal end with a first hairpin probe and a second hairpin probe to form an RNA detection structure, wherein
      i) said first hairpin probe comprises a 3' region that is complementary said 3' portion of said microRNA, and a 5' region that is not complementary to said microRNA, wherein a first portion of said 5' region is complementary to a second portion of said 5' region, wherein said first portion and said second portion of said 5' region hybridize to each other to form a first duplex when said first hairpin probe is hybridized to said microRNA, and wherein said first duplex and said 3' region of said probe are within one nucleotide of each other; and
      ii) said second hairpin probe comprises a 5' region that is complementary to said 5' portion of said microRNA and a 3' region that is not complementary to said microRNA, wherein a first portion of said 3' region is complementary to a second portion of said 3' region, wherein said first portion and said second portion of said 3' region hybridize to each other to form a second duplex when said hairpin probe is hybridized to said microRNA, and wherein said second duplex and said 5' region of said probe are within one nucleotide of each other;

wherein, in said RNA detection structure, said microRNA and said first and second hairpin probes form a dumbbell structure,
   b) detecting formation of said RNA detection structure, wherein formation of said RNA detection structure is indicative of the presence of said microRNA.

2. The method of claim 1, wherein said detecting comprises quantitating said microRNA.

3. The method of claim 1, wherein said detecting comprises forming an invasive cleavage structure, cleaving said invasive cleavage structure, and detecting the cleavage of said invasive cleavage structure.

4. The method of claim 1, wherein said detecting comprises use of a detection assay that employs sequence analysis.

5. The method of claim 1, wherein said detecting comprises use of a detection assay that employs polymerase chain reaction.

6. The method of claim 1, wherein said detecting comprises use of a detection assay that employs microarray hybridization.

7. The method of claim 1, wherein said detecting comprises use of a detection assay that employs ligation.

8. The method of claim 1, wherein said detecting comprises use of a labeled probe.

9. The method of claim 8, wherein said labeled probe is fluorescently labeled.

10. The method of claim 8, wherein said labeled probe is configured for FRET detection.

11. The method of claim 10, wherein said labeled probe has a first conformation when not hybridized in a duplex and a second conformation when hybridized in a duplex.

12. The method of claim 10, wherein said labeled probe exhibits increased fluorescence when hybridized in a duplex.

13. The method of claim 1, wherein said detecting comprises use of a detection assay that employs polymerase chain reaction coupled with 5' nuclease cleavage of a labeled probe.

14. The method of claim 13, wherein said labeled probe is fluorescently labeled.

15. The method of claim 13, wherein said labeled probe is configured for FRET detection upon cleavage.

16. The method of claim 1, wherein said detecting comprises exposing said RNA detection structure to a polymerase under conditions that permit primer extension.

17. The method of claim 1, wherein said detecting comprises determining the presence of said microRNA in a sample.

18. The method of claim 17, wherein said detecting comprises distinguishing said microRNA from another nucleic acid in said sample.

19. The method of claim 18, wherein said sample comprises a cell lysate.

20. The method of claim 1, wherein said microRNA is approximately 21-22 nucleotides in length.

21. The method of claim 1, wherein a plurality of different microRNAs are detected.

22. The method of claim 21, wherein said plurality of microRNAs comprise a first microRNA and a second microRNA that is said first microRNA having a polymorphism.

23. The method of claim 1, wherein said microRNA is selected from the group consisting of Let-7, miR-1, miR-135, miR-15, miR-16, miR125b, miR-1d, and miR124a.

24. The method of claim 1, wherein at least a portion of said RNA detection structure comprises a nucleotide analog.

25. The method of claim 1, wherein at least a portion of said RNA detection structure comprises a peptide nucleic acid.

26. A method for analyzing microRNA in a sample, comprising:
a) contacting microRNA comprising a 3' portion comprising a 3' terminal end and a 5' portion comprising a 5' terminal end with a first hairpin probe and a second hairpin probe to form an RNA detection structure wherein
i) said first hairpin probe comprises a 3' region that is complementary said 3' portion of said microRNA, and a 5' region that is not complementary to said microRNA, wherein a first portion of said 5' region is complementary to a second portion of said 5' region, wherein said first portion and said second portion of said 5' region hybridize to each other to form a first duplex when said hairpin probe is hybridized to said microRNA, and wherein said first duplex and said 3' region of said probe are within one nucleotide of each other; and
ii) said second hairpin probe comprises a 5' region that is complementary to said 5' portion of said microRNA and a 3' region that is not complementary to said microRNA, wherein a first portion of said 3' region is complementary to a second portion of said 3' region, wherein said first portion and said second portion of said 3' region hybridize to each other to form a second duplex when said hairpin probe is hybridized to said microRNA, and wherein said second duplex and said 5' region of said probe are within one nucleotide of each other;

wherein, in said RNA detection structure, said microRNA and said first and second hairpin probes form a dumbbell structure,
b) reacting said RNA detection structure with a nucleic acid modifying enzyme to form an modified RNA detection structure;
c) detecting formation of said modified RNA detection structure, wherein formation of said modified RNA detection structure is indicative of the presence of said microRNA, and wherein said detecting formation of said modified RNA detection structure comprises use of an amplification reaction.

27. The method of claim 26, wherein said amplification reaction comprises a target amplification reaction.

28. The method of claim 27, wherein said target amplification reaction comprises a polymerase chain reaction.

29. The method of claim 26, wherein said amplification reaction comprises a signal amplification reaction.

30. The method of claim 29, wherein said signal amplification reaction comprises forming an invasive cleavage structure, cleaving said invasive cleavage structure, and detecting the cleavage of said invasive cleavage structure.

31. The method of claim 26, wherein said detecting comprises quantitating said microRNA.

32. The method of claim 26, wherein said detecting comprises use of a labeled probe.

33. The method of claim 32, wherein said labeled probe is fluorescently labeled.

34. The method of claim 33, wherein said labeled probe is configured for FRET detection.

35. The method of claim 32, wherein said labeled probe has a first conformation when not hybridized in a duplex and a second conformation when hybridized in a duplex.

36. The method of claim 32, wherein said labeled probe exhibits increased fluorescence when hybridized in a duplex.

37. The method of claim 28, wherein said polymerase chain reaction is coupled with 5' nuclease cleavage of a labeled probe.

38. The method of claim 37, wherein said labeled probe is fluorescently labeled.

39. The method of claim 37, wherein said labeled probe is configured for FRET detection upon cleavage.

40. The method of claim 26, wherein said detecting comprises exposing said RNA detection structure to a polymerase under conditions that permit primer extension.

41. The method of claim 26, wherein said detecting comprises distinguishing said microRNA from another nucleic acid in said sample.

42. The method of claim 26, wherein said sample comprises a cell lysate.

43. The method of claim 26, wherein said microRNA is approximately 21-22 nucleotides in length.

44. The method of claim 26, wherein a plurality of different microRNAs are detected.

45. The method of claim 42, wherein said plurality of microRNAs comprise a first microRNA and a second microRNA that is said first microRNA having a polymorphism.

46. The method of claim 26, wherein said microRNA is selected from the group consisting of Let-7, miR-1, miR-135, miR-15, miR-16, miR125b, miR-1d, and miR124a.

47. The method of claim 26, wherein at least a portion of said unlabeled RNA detection structure comprises a nucleotide analog.

48. The method of claim 26, wherein at least a portion of said unlabeled RNA detection structure comprises a peptide nucleic acid.

* * * * *